US011467098B2

(12) United States Patent
Kester et al.

(10) Patent No.: US 11,467,098 B2
(45) Date of Patent: Oct. 11, 2022

(54) SYSTEMS AND METHODS FOR MONITORING REMOTE INSTALLATIONS

(71) Applicant: REBELLION PHOTONICS, INC., Houston, TX (US)

(72) Inventors: Robert Timothy Kester, Friendswood, TX (US); Margarita Sergeyevna Odintsova, Houston, TX (US)

(73) Assignee: REBELLION PHOTONICS, INC., Houston, TX (US)

(*) Notice: Subject to any disclaimer, the term of this patent is extended or adjusted under 35 U.S.C. 154(b) by 0 days.

(21) Appl. No.: 17/249,125

(22) Filed: Feb. 22, 2021

(65) Prior Publication Data
US 2021/0255113 A1 Aug. 19, 2021

Related U.S. Application Data

(63) Continuation of application No. 15/902,336, filed on Feb. 22, 2018, now Pat. No. 10,955,355.

(Continued)

(51) Int. Cl.
*G01N 21/88* (2006.01)
*G01M 3/20* (2006.01)
(Continued)

(52) U.S. Cl.
CPC ........ *G01N 21/8851* (2013.01); *G01J 3/0232* (2013.01); *G01J 3/28* (2013.01); *G01J 3/2823* (2013.01); *G01J 5/0066* (2013.01); *G01J 5/0804* (2022.01); *G01M 3/20* (2013.01); *G01N 21/3504* (2013.01); *G01N 33/0044* (2013.01);
(Continued)

(58) Field of Classification Search
None
See application file for complete search history.

(56) References Cited

U.S. PATENT DOCUMENTS 3,841,763 A 10/1974 Lewis
3,849,005 A 11/1974 Girard et al.
(Continued)

FOREIGN PATENT DOCUMENTS

CA 2365866 A1 9/2000
CA 2787303 A1 7/2011
(Continued)

OTHER PUBLICATIONS

US 10,113,914 B2, 10/2018, Kester et al. (withdrawn)
(Continued)

*Primary Examiner* — James M Anderson, II
(74) *Attorney, Agent, or Firm* — Alston & Bird LLP

(57) ABSTRACT

A system for monitoring a petrochemical installation is disclosed. The system can include an optical imaging system comprising an array of optical detectors. The system can comprise processing electronics configured to process image data detected by the optical imaging system. The processing electronics can be configured to detect a target species based at least in part on the processed image data. The processing electronics can further be configured to, based on a detected amount of the target species, transmit an alarm notification to an external computing device over a communications network indicating that the target species has been detected at the petrochemical installation.

20 Claims, 33 Drawing Sheets

Related U.S. Application Data

(60) Provisional application No. 62/462,851, filed on Feb. 23, 2017, provisional application No. 62/462,345, filed on Feb. 22, 2017.

(51) Int. Cl.

| | | |
|---|---|---|
| *G01J 3/02* | (2006.01) | |
| *G01J 5/00* | (2022.01) | |
| *G01J 3/28* | (2006.01) | |
| *G08B 21/18* | (2006.01) | |
| *G08B 13/189* | (2006.01) | |
| *G08B 21/14* | (2006.01) | |
| *G01N 21/3504* | (2014.01) | |
| *G01J 5/0804* | (2022.01) | |
| *G06V 20/52* | (2022.01) | |
| *G01N 33/00* | (2006.01) | |
| *G08B 21/12* | (2006.01) | |
| *H04N 5/33* | (2006.01) | |
| *H04N 7/18* | (2006.01) | |
| *G01N 21/27* | (2006.01) | |
| *G01J 5/80* | (2022.01) | |
| *G06T 3/40* | (2006.01) | |

(52) U.S. Cl.
CPC ......... *G01N 33/0047* (2013.01); *G06V 20/52* (2022.01); *G08B 13/1895* (2013.01); *G08B 21/12* (2013.01); *G08B 21/14* (2013.01); *G08B 21/182* (2013.01); *H04N 5/33* (2013.01); *H04N 7/181* (2013.01); *G01J 5/80* (2022.01); *G01J 2003/2826* (2013.01); *G01J 2005/0077* (2013.01); *G01N 21/274* (2013.01); *G01N 2021/3531* (2013.01); *G06T 3/4038* (2013.01)

(56) References Cited

U.S. PATENT DOCUMENTS

| | | | |
|---|---|---|---|
| 4,134,683 A | 1/1979 | Goetz et al. | |
| 4,390,785 A | 6/1983 | Faulhaber et al. | |
| 4,464,789 A | 8/1984 | Sternberg | |
| 4,933,555 A | 6/1990 | Smith | |
| 4,963,963 A | 10/1990 | Dorman | |
| 4,965,448 A | 10/1990 | Morse et al. | |
| 5,127,742 A | 7/1992 | Fraden | |
| 5,136,421 A | 8/1992 | Sagan | |
| 5,157,258 A | 10/1992 | Gunning et al. | |
| 5,354,987 A | 10/1994 | MacPherson | |
| 5,430,293 A * | 7/1995 | Sato | G01M 3/38 250/330 |
| 5,550,373 A | 8/1996 | Cole et al. | |
| 5,559,336 A | 9/1996 | Kosai et al. | |
| 5,604,346 A | 2/1997 | Hamrelius et al. | |
| 5,822,222 A | 10/1998 | Kaplinsky et al. | |
| 5,877,500 A | 3/1999 | Braig et al. | |
| 5,890,095 A | 3/1999 | Barbour et al. | |
| 5,920,066 A | 7/1999 | Direnzo et al. | |
| 5,926,283 A | 7/1999 | Hopkins | |
| 5,973,844 A | 10/1999 | Burger | |
| 5,994,701 A | 11/1999 | Tsuchimoto et al. | |
| 6,023,061 A | 2/2000 | Bodkin | |
| 6,097,034 A | 8/2000 | Weckstroem et al. | |
| 6,184,529 B1 | 2/2001 | Contini | |
| 6,268,883 B1 | 7/2001 | Zehnder et al. | |
| 6,456,261 B1 | 9/2002 | Zhang | |
| 6,465,785 B1 | 10/2002 | McManus | |
| 6,556,853 B1 | 4/2003 | Cabib et al. | |
| 6,680,778 B2 | 1/2004 | Hinnrichs et al. | |
| 6,695,886 B1 | 2/2004 | Brown et al. | |
| 6,700,527 B1 | 3/2004 | Martin et al. | |
| 7,109,488 B2 | 9/2006 | Milton | |
| 7,119,337 B1 | 10/2006 | Johnson et al. | |
| 7,242,478 B1 | 7/2007 | Dombrowski et al. | |
| 7,315,377 B2 | 1/2008 | Holland et al. | |
| 7,321,119 B2 | 1/2008 | King | |
| 7,364,697 B2 | 4/2008 | McFarland et al. | |
| 7,433,042 B1 | 10/2008 | Cavanaugh et al. | |
| 7,606,484 B1 | 10/2009 | Richards et al. | |
| 7,634,157 B1 | 12/2009 | Richards et al. | |
| 7,750,802 B1 | 7/2010 | Parish et al. | |
| 7,835,002 B2 | 11/2010 | Muhammed et al. | |
| 7,888,624 B1 | 2/2011 | Murguia et al. | |
| 8,027,041 B1 | 9/2011 | Mitchell et al. | |
| 8,153,980 B1 | 4/2012 | Brady et al. | |
| 8,159,568 B2 | 4/2012 | Ahdoot | |
| 8,212,213 B2 | 7/2012 | Myrick et al. | |
| 8,373,757 B1 | 2/2013 | Nguyen | |
| 8,629,930 B2 | 1/2014 | Brueckner et al. | |
| 8,653,461 B1 | 2/2014 | Benson et al. | |
| 8,654,328 B2 | 2/2014 | Tkaczyk et al. | |
| 8,686,364 B1 | 4/2014 | Little et al. | |
| 9,225,913 B2 | 12/2015 | Ekdahl | |
| 9,395,516 B2 | 7/2016 | Katsunuma et al. | |
| 9,404,804 B1 | 8/2016 | Liu et al. | |
| 9,562,849 B2 | 2/2017 | Kester et al. | |
| 9,599,508 B2 | 3/2017 | Kester et al. | |
| 9,612,195 B1 * | 4/2017 | Friedman | G01N 33/004 |
| 9,625,318 B2 | 4/2017 | Kester et al. | |
| 9,641,772 B2 | 5/2017 | Yujiri | |
| 9,644,562 B2 | 5/2017 | Fujita | |
| 9,756,263 B2 | 9/2017 | Kester et al. | |
| 9,823,231 B1 | 11/2017 | Steele et al. | |
| 10,084,975 B2 | 9/2018 | Kester et al. | |
| 10,254,166 B2 | 4/2019 | Kester et al. | |
| 10,267,686 B2 | 4/2019 | Kester et al. | |
| 10,375,327 B2 | 8/2019 | Kester | |
| 10,444,070 B2 | 10/2019 | Kester et al. | |
| 10,458,905 B2 | 10/2019 | Kester et al. | |
| 10,605,725 B2 | 3/2020 | Mallery et al. | |
| 10,648,960 B2 | 5/2020 | Kester et al. | |
| 10,955,355 B2 | 3/2021 | Kester et al. | |
| 2001/0040216 A1 | 11/2001 | Knauth et al. | |
| 2002/0015151 A1 | 2/2002 | Gorin | |
| 2002/0121370 A1 | 9/2002 | Kurkjian et al. | |
| 2002/0159101 A1 | 10/2002 | Alderson et al. | |
| 2003/0102435 A1 | 6/2003 | Myers et al. | |
| 2003/0134426 A1 | 7/2003 | Jiang et al. | |
| 2003/0183756 A1 | 10/2003 | Huniu | |
| 2004/0093167 A1 | 5/2004 | Braig et al. | |
| 2004/0111232 A1 | 6/2004 | Butler et al. | |
| 2004/0252300 A1 | 12/2004 | Slater | |
| 2005/0029453 A1 | 2/2005 | Allen et al. | |
| 2005/0057366 A1 | 3/2005 | Kadwell et al. | |
| 2005/0103989 A1 | 5/2005 | Watson et al. | |
| 2005/0156111 A1 | 7/2005 | Racca et al. | |
| 2006/0044562 A1 | 3/2006 | Hagene et al. | |
| 2006/0091310 A1 * | 5/2006 | Furry | G01N 21/3518 250/330 |
| 2006/0183241 A1 | 8/2006 | Lehmann et al. | |
| 2006/0203248 A1 | 9/2006 | Reichardt et al. | |
| 2006/0232675 A1 | 10/2006 | Chamberlain et al. | |
| 2006/0279632 A1 | 12/2006 | Anderson | |
| 2007/0018105 A1 | 1/2007 | Grimberg | |
| 2007/0075888 A1 | 4/2007 | Kelly et al. | |
| 2007/0108385 A1 | 5/2007 | Mantese et al. | |
| 2007/0170357 A1 | 7/2007 | Arseneau | |
| 2007/0170359 A1 | 7/2007 | Syllaios et al. | |
| 2007/0170363 A1 | 7/2007 | Schimert et al. | |
| 2007/0216136 A1 * | 9/2007 | Dietz | B60D 1/62 280/477 |
| 2007/0268121 A1 | 11/2007 | Vasefi et al. | |
| 2008/0170140 A1 | 7/2008 | Silver et al. | |
| 2008/0204744 A1 | 8/2008 | Mir et al. | |
| 2008/0231719 A1 | 9/2008 | Benson et al. | |
| 2008/0251724 A1 | 10/2008 | Baliga et al. | |
| 2009/0015824 A1 | 1/2009 | Shubinsky et al. | |
| 2009/0252650 A1 | 10/2009 | Lakshmanan | |
| 2010/0013979 A1 | 1/2010 | Golub et al. | |
| 2010/0162206 A1 | 6/2010 | Roth et al. | |
| 2010/0171866 A1 | 7/2010 | Brady et al. | |
| 2010/0211333 A1 | 8/2010 | Pruet et al. | |

(56) References Cited

U.S. PATENT DOCUMENTS

| | | |
|---|---|---|
| 2010/0309467 A1 | 12/2010 | Fox et al. |
| 2011/0176577 A1 | 7/2011 | Bandara et al. |
| 2011/0185048 A1 | 7/2011 | Yew et al. |
| 2011/0261321 A1 | 10/2011 | Ramella-Roman et al. |
| 2011/0271738 A1 | 11/2011 | McGill et al. |
| 2011/0285995 A1 | 11/2011 | Tkaczyk et al. |
| 2012/0154792 A1 | 6/2012 | Treado et al. |
| 2012/0273680 A1 | 11/2012 | Furry |
| 2012/0314080 A1 | 12/2012 | Lee et al. |
| 2013/0181836 A1 | 7/2013 | Cardoso et al. |
| 2013/0206990 A1 | 8/2013 | Hsu et al. |
| 2013/0228887 A1 | 9/2013 | Wehner et al. |
| 2013/0235256 A1 | 9/2013 | Kodama |
| 2013/0250124 A1 | 9/2013 | Furry |
| 2013/0286213 A1 | 10/2013 | Cetin et al. |
| 2013/0307991 A1 | 11/2013 | Olsen et al. |
| 2013/0321806 A1 | 12/2013 | Kester et al. |
| 2013/0341509 A1 | 12/2013 | Nelson et al. |
| 2013/0342680 A1 | 12/2013 | Zeng et al. |
| 2014/0002639 A1 | 1/2014 | Cheben et al. |
| 2014/0139643 A1 | 5/2014 | Hogasten et al. |
| 2014/0320843 A1 | 10/2014 | Streuber et al. |
| 2014/0375752 A1* | 12/2014 | Shoemake .............. H04N 7/141 348/14.07 |
| 2015/0069239 A1 | 3/2015 | Kester et al. |
| 2015/0136981 A1 | 5/2015 | Kester et al. |
| 2015/0136982 A1 | 5/2015 | Kester et al. |
| 2015/0138534 A1 | 5/2015 | Tidhar |
| 2015/0144770 A1 | 5/2015 | Choi |
| 2015/0226613 A1 | 8/2015 | Bauer et al. |
| 2015/0234387 A1* | 8/2015 | Mullan .................. G05D 1/104 701/3 |
| 2015/0288894 A1 | 10/2015 | Geelen et al. |
| 2015/0292948 A1 | 10/2015 | Goldring et al. |
| 2015/0316473 A1* | 11/2015 | Kester .................. G01J 3/2803 250/339.02 |
| 2016/0037089 A1 | 2/2016 | Silny et al. |
| 2016/0041095 A1 | 2/2016 | Rothberg et al. |
| 2016/0097713 A1 | 4/2016 | Kester et al. |
| 2016/0097714 A1 | 4/2016 | Zeng et al. |
| 2016/0238449 A1 | 8/2016 | Goldring et al. |
| 2016/0238454 A1 | 8/2016 | Pillans |
| 2016/0245698 A1 | 8/2016 | Pau et al. |
| 2016/0249228 A1 | 8/2016 | Zhao |
| 2016/0313181 A1 | 10/2016 | Golub et al. |
| 2016/0349228 A1 | 12/2016 | Kester et al. |
| 2016/0356702 A1 | 12/2016 | Hinnrichs |
| 2016/0379059 A1* | 12/2016 | Gottschlich ........ H04N 5/23229 348/143 |
| 2016/0380014 A1 | 12/2016 | Ganapathi et al. |
| 2017/0026588 A1 | 1/2017 | Kester et al. |
| 2017/0059807 A1 | 3/2017 | Feng |
| 2017/0089761 A1 | 3/2017 | McQuilkin et al. |
| 2017/0138846 A1 | 5/2017 | Alizadeh et al. |
| 2017/0138918 A1 | 5/2017 | Bardoni |
| 2017/0205290 A1 | 7/2017 | Kester et al. |
| 2017/0234761 A1 | 8/2017 | Augusto |
| 2017/0248517 A1 | 8/2017 | Scherer et al. |
| 2017/0347037 A1 | 11/2017 | Hall et al. |
| 2017/0350758 A1 | 12/2017 | Kester et al. |
| 2017/0356802 A1 | 12/2017 | Kester et al. |
| 2018/0003641 A1* | 1/2018 | Gamache ................ G01M 3/20 |
| 2018/0039885 A1 | 2/2018 | Albrecht et al. |
| 2018/0077363 A1 | 3/2018 | Kester et al. |
| 2018/0188163 A1 | 7/2018 | Kester et al. |
| 2018/0191967 A1 | 7/2018 | Kester |
| 2019/0003984 A1 | 1/2019 | Kester et al. |
| 2019/0137388 A1 | 5/2019 | Mallery et al. |
| 2019/0273875 A1 | 9/2019 | Kester et al. |
| 2019/0373185 A1 | 12/2019 | Kester et al. |
| 2020/0072671 A1 | 3/2020 | Kester et al. |
| 2020/0088586 A1 | 3/2020 | Kester et al. |
| 2020/0124470 A1 | 4/2020 | Kester et al. |
| 2020/0124525 A1 | 4/2020 | Kester et al. |
| 2020/0128196 A1 | 4/2020 | Kester |
| 2020/0132596 A1 | 4/2020 | Mallery et al. |

FOREIGN PATENT DOCUMENTS

| | | |
|---|---|---|
| CA | 2870419 A1 | 5/2015 |
| EP | 0837600 A2 | 4/1998 |
| EP | 2870419 A1 | 5/2015 |
| EP | 2871452 A1 | 5/2015 |
| EP | 2942615 A1 | 11/2015 |
| EP | 2955496 A2 | 12/2015 |
| EP | 3040706 A1 | 7/2016 |
| GB | 1014769 A | 12/1965 |
| GB | 2518224 A | 3/2015 |
| JP | 2013-128185 A | 6/2013 |
| WO | 2004/097389 A2 | 11/2004 |
| WO | 2007/008826 A2 | 1/2007 |
| WO | 2008/109183 A1 | 9/2008 |
| WO | 2009/094782 A1 | 8/2009 |
| WO | 2010/053979 A2 | 5/2010 |
| WO | 2012/078417 A1 | 6/2012 |
| WO | 2012/082366 A1 | 6/2012 |
| WO | 2013/173541 A1 | 11/2013 |
| WO | 2014/008137 A1 | 1/2014 |
| WO | 2015/108236 A1 | 7/2015 |
| WO | 2016/196224 A1 | 12/2016 |
| WO | 2017/201194 A1 | 11/2017 |
| WO | 2018/075957 A1 | 4/2018 |
| WO | 2018/075964 A1 | 4/2018 |
| WO | 2018/156795 A1 | 8/2018 |
| WO | 2019/094639 A1 | 5/2019 |

OTHER PUBLICATIONS

Official Communication received in U.S. Appl. No. 14/792,477 dated Jul. 19, 2017 in 20 pages.
Official Communication received in U.S. Appl. No. 14/543,692 (REBPH.OOICI) dated Nov. 3, 2015 in 7 pages.
Official Communication received in U.S. Appl. No. 14/700,567 (REBPH.004A) dated Jun. 14, 2017 in 29 pages.
Official Communication received in U.S. Appl. No. 14/700,567 (REBPH.004A) dated Mar. 5, 2018 in 38 pages.
Official Communication received in U.S. Appl. No. 15/166,092 (REBPH.008A) dated Dec. 20, 2018 in 28 pages.
Official Communication received in U.S. Appl. No. 15/166,092 (REBPH.008A) dated May 15, 2018 in 30 pages.
Official Communication received in U.S. Appl. No. 15/418,532 (REBPH.001A2C1) dated Dec. 11, 2017 in 21 pages.
Official Communication received in U.S. Appl. No. 15/418,532 (REBPH.001A2CI) dated Jun. 23, 2017 in 7 pages.
Official Communication received in U.S. Appl. No. 15/462,352 (REBPH.001P1CI) dated Sep. 28, 2017 in 6 pages.
Official Communication received in U.S. Appl. No. 15/789,811 (REBPH.OIOA) dated Jul. 27, 2018 in 22 pages.
Official Communication received in U.S. Appl. No. 15/789,829 (REBPH.012A) dated Jun. 5, 2018 in 16 pages.
Official Communication received in U.S. Appl. No. 15/789,829 (REBPH.012A) dated Nov. 6, 2019 in 23 pages.
Official Communication received in U.S. Appl. No. 16/185,399 (REBPH.014A) dated Apr. 2, 2019 in 24 pages.
Official Communication received in U.S. Appl. No. 16/256,967 (REBPH.004C1) dated Oct. 2, 2019 in 12 pages.
Official Communication received in U.S. Appl. No. 16/549,297 (REBPH.001P1C2) dated May 1, 2020 in 8 pages.
Official Communication received in U.S. Appl. No. 16/664,615 (REBPH.014CI) dated Apr. 9, 2020 in 9 pages.
Oil and Natural Gas Sector Leaks, U.S. EPA Office of Air Quality Planning and Standards (OAQPS), Review Panel, Apr. 2014, pp. 63.
Petron et al., "Hydrocarbon Emissions Characterization in the Colorado Front Range: A Pilot Study", Journal of Geophysical Research, 2012, vol. 117, No. D04304, pp. 1-19.
Petron et al., "Reply to Comment on 'Hydrocarbon Emissions Characterization in the Colorado Front Range—A Pilot Study' by Michael A. Levi", Journal of Geophysical Research: Atmospheres, 2013, vol. 118, pp. 236-242.

(56) References Cited

OTHER PUBLICATIONS

Pisano et al., "Thermal Illuminators for Far-Infrared and Submillimeter Astronomical Instruments," Applied Optics, Jun. 1, 2005, vol. 44, No. 16, pp. 3208-3217.
Polak et al., "Passive Fourier-Transform Infrared Spectroscopy of Chemical Plumes: An Algorithm for Quantitative Interpretation and Real-Time Background Removal", Applied Optics, Aug. 20, 1995, vol. 34, No. 24, pp. 5406-5412.
Preliminary Amendment as filed in U.S. Appl. No. 16/138,823 (REBPH.003C2) dated May 23, 2019 in 5 pages.
Preliminary Amendment as filed in U.S. Appl. No. 14/792,477 dated Dec. 21, 2015 in 7 pages.
Preliminary Amendment as filed in U.S. Appl. No. 14/538,827 (REBPH.001A2) dated Jan. 28, 2015 in 6 pages.
Preliminary Amendment as filed in U.S. Appl. No. 14/700,567 (REBPH.004A) dated Jul. 10, 2015 in 6 pages.
Preliminary Amendment as filed in U.S. Appl. No. 14/700,791 (REBPH.003A) dated Jul. 13, 2015 in 8 pages.
Preliminary Amendment as filed in U.S. Appl. No. 15/166,092 (REBPH.008A) dated Aug. 15, 2016 in 7 pages.
Preliminary Amendment as filed in U.S. Appl. No. 15/471,398 (REBPH.001O2) dated Oct. 6, 2017 in 6 pages.
Preliminary Amendment as filed in U.S. Appl. No. 15/623,942 (REBPH.003C1) dated Dec. 7, 2017 in 6 pages.
Preliminary Amendment as filed in U.S. Appl. No. 15/789,811 (REBPH.001A) dated Mar. 20, 2018 in 6 pages.
Preliminary Amendment as filed in U.S. Appl. No. 15/789,829 (REBPH.012A) dated Mar. 20, 2018 in 8 pages.
Preliminary Amendment as filed in U.S. Appl. No. 16/256,967 (REBPH.004C1) dated Aug. 27, 2019 in 6 pages.
Preliminary Amendment as filed in U.S. Appl. No. 16/377,678 (REBPH.001C3) dated Nov. 21, 2015 in 4 pages.
Publication Request as filed in U.S. Appl. No. 14/700,567 (REBPH.004A) dated Aug. 24, 2016 in 237 pages.
Rebellion Photonics, "Gas Cloud Imaging Camera: A Breakthrough in Leak Monitoring for the Rig & Refinery Safety Market", Presentation at SPIE Defense Security and Sensing, 28 pages, Apr. 29-May 3, 2013.
Request for Continued Examination and Response to Correct Application Papers as filed in U.S. Appl. No. 14/538,827 (REBPH.001A2) dated Apr. 29, 2016 in 14 pages.
Response to 312 Amendment received in U.S. Appl. No. 16/185,399 (REBPH.014A) dated Feb. 18, 2020 in 4 pages.
Response to Final Action as filed in U.S. Appl. No. 14/543,692 (REBPH.001CI) dated Nov. 30, 2016 in 12 pages.
Response to Notice to File Corrected Application Papers filed in U.S. Appl. No. 15/462,352 (REBPH.001P1C1) dated Oct. 8, 2018 in 3 pages.
Response to Office Action as filed in U.S. Appl. No. 14/543,692 (REBPH.001CI) dated May 2, 2016 in 9 pages.
Response to Restriction Requirement submitted in U.S. Appl. No. 14/792,477 dated May 8, 2017 in 6 pages.
Result of Consultation dated Feb. 27, 2018 for EP Application No. 15165877.0.
Sandsten et al, "Development of Infrared Spectroscopy Techniques for Environmental Monitoring", Doctoral Thesis, Aug. 2000, pp. 123.
Sandsten et al., "Real-Time Gas-Correlation Imaging Employing Thermal Background Radiation", Optics Express, Feb. 14, 2000, vol. 5, No. 4, pp. 92-103.
Sandsten et al., "Volume Flow Calculations on Gas Leaks Imaged with Infrared Gas-Correlation," Optics Express, 2012, vol. 20, No. 18, pp. 20318-20329.
Shogenji et al., "Multispectral Imaging Using Compact Compound Optics," Optics Express, Apr. 19, 2004, vol. 12, No. 8, pp. 1643-1655.
Summons to Attend Oral Hearing dated Oct. 10, 2017 for EP Application No. 15165877.0.
TELOPS, "Hyper-Cam", http://web.archive.org/web/20160608180941/http://www.teloos.com/en/hyperspectral-cameras/hyper-cam as archived Jun. 8, 2016 in 2 pages.
TELOPS, "Innovative Infrared Imaging", http://web.archive.org.web/20160603212729/http://www.telops.com/en/as archived Jun. 3, 2016 in 2 pages.
Walter Jr., et al., "Detection of Atmospheric Pollutants: a Correlation Technique", Applied Optics, Jun. 1975, vol. 14, No. 6, pp. 1423-1428.
Directed Inspection and Maintenance at Gas Processing Plants and Booster Stations, United States Environmental Protection Agency Air and Radiation (6202J), EPA430-B-03-018, Oct. 2003 available at https://www3.epa.gov/gasstar/documents/II.sub.--dimgasproc.pdf.
EP Office Action dated Jan. 3, 2017 for EP Application No. 15165877.0, 9 pages.
EP Office Action dated Jul. 5, 2019 for EP Application 15165880.
Eriksson et al., "Radiative Cooling Computed for Model Atmospheres", Applied Optics, Dec. 1, 1982, vol. 21, No. 23, pp. 4381-4388.
European Search Report and Search Opinion Received for EP Application No. 17863243.6, dated Apr. 20, 2020, 8 Pages.
European search report dated May 13, 2020 for EP Application No. 17862635.4, 14 pages.
Extended European Search Report received in European Application No. 14192862.2 (REBPH.001EP2) dated Mar. 30, 2015 in 10 pages.
Extended European Search Report received in European Application No. 15165877.0 dated Oct. 8, 2015 in 12 pages.
Extended European Search Report received in European Application No. 19170836.1 (REBPH.001 EP2D1) dated Aug. 16, 2019 in 12 pages.
Extended European Search Report received in European Application No. EP 15165880.4 (REBPH.004EP) dated Nov. 24, 2015 in 8 pages.
Extended European Search Report received in European Application No. EP 16804077.2 (REBPH.008EP) dated Jan. 8, 2019 in 8 pages.
Final Office Action received in U.S. Appl. No. 14/539,899 (REBPH.001P1) dated Dec. 11, 2015 in 9 pages.
Flanigan, "Detection of Organic Vapors with Active and Passive Sensors: A Comparison," Applied Optics, 1986, vol. 25, No. 23, pp. 4253-4260.
Galfalk et al., "Making Methane Visible", Nature Climate Change, Apr. 2016, vol. 6, pp. 426-430.
Galfalk et al., "Making Methane Visible", Supplementary Information, Nature Climate Change, 2015, pp. 1-14.
Gallagher et al., "Error Analysis for Estimation of Trace Vapor Concentration Pathlength in Stack Plumes", Applied Spectroscopy, 2003, vol. 57, No. 6, pp. 614-621.
Gallagher et al., "Estimation of Trace Vapor Concentration-Pathlength in Plumes for Remote Sensing Applications from Hyperspectral Images", Analytica Chimica Acta, 2003, vol. 490, pp. 139-152.
Gao et al., "Compact Image Slicing Spectrometer (ISS) for Hyperspectral Fluorescence Microscopy", Optics Express, Jul. 20, 2009, vol. 17, No. 15, pp. 12293-12308.
Gao et al., "Depth-Resolved Image Mapping Spectrometer (IMS) with Structured Illumination", Optics Express, Aug. 29, 2011, vol. 19, No. 18, pp. 17439-17452.
Gao et al., "Optical Design of a Snapshot High-Sampling Image Mapping Spectrometer (IMS) for Hyperspectral Microscopy", Three-Dimensional and Multidimensional Microscopy: Image Acquisition and Processing XVII, Proceedings of SPIE vol. 7570, 2010, pp. 1-7.
Gao et al., "Quantitative Comparison Between Full-Spectrum and Filter-Based Imaging in Hyperspectral Fluorescence Microscopy", Journal of Microscopy, 2012, vol. 246, No. 2, pp. 113-123.
Gao et al., "Snapshot Image Mapping Spectrometer (IMS) with High Sampling Density for Hyperspectral Microscopy", Optics Express, Jul. 5, 2010, vol. 18, No. 4, pp. 14330-14344.
Gao et al., "Snapshot Image-Mapping Spectrometer for Hyperspectral Fluorescence Microscopy", Optics and Photonics News, Nov. 2010, vol. 21, No. 12, p. 50.

(56) References Cited

OTHER PUBLICATIONS

Gerhart et al, "Detection and Tracking of Gas Plumes in LWIR Hyperspectral Video Sequence Data," Algorithms and Technologies for Multispectral, Hyperspectral, and Ultraspectral Imagery XIX, 2013, SPIE Proceedings vol. 8743, pp. 1-14.

Gittins, Christopher M., "Detection and Characterization of Chemical Vapor Fugitive Emissions by Nonlinear Optimal Estimation: Theory and Simulation", Applied Optics, Aug. 10, 2009, vol. 48, No. 23, pp. 4545-4561.

Goldberg et al., "Dual Band MWIR/LWIR Focal Plane Array Test Results," Army Research Lab, Adelphi, MD, Aug. 1999, pp. 18.

Golwich et al., "Performance Limits of LWIR Gaseous Plume Quantification", Algorithms and Technologies for Multispectral, Hyperspectrai, and Ultraspectrai Imagery XVII, 2011, Proceedings of SPIE vol. 8048, pp. 1-12.

Griffin et al., "The Herschel-• SPIRE 1-15 Instrument and its In-•Flight Performance," Astronomy and Astrophysics, Jul. 1, 2010, vol. 518, pp. 7.

Gross et al., "Remote Identification and Quantification of Industrial Smokestack Effluents via Imaging Fourier-Transform Spectroscopy", Environmental Science & Technology, 2010, vol. 44, No. 24, pp. 9390-9397.

Gupta et al., "Miniature Snapshot Multispectral Imager," Optical Engineering, 2011, vol. 50, pp. 033203-1-033203-9.

Hadlington, Simon, "New Camera Makes Methane Visible", Chemistry World, http://web.archive.org/web/20160305234907/http://www.rsc.org/chemistrywor-ld/2015/12/methane-camera-infared-greenhouse-gas, Dec. 14, 2015, pp. 2.

Hagen et al., "Analysis of Computed Tomographic Imaging Spectrometers. I. Spatial and Spectral Resolution", Applied Optics, Oct. 1, 2008, vol. 47, No. 28, pp. F85-F95.

Hagen et al., "Coded Aperture DUV Spectrometer for Standoff Raman Spectoscopy", Next-Generation Spectroscopic Technologies II, Proceedings of SPIE vol. 7319, 2009, pp. 1-10.

Hagen et al., "Compound Prism Design Principles, I", Applied Optics, Sep. 1, 2011, vol. 50, No. 25, pp. 4998-5011.

Hagen et al., "Compound Prism Design Principles, II: Triplet and Janssen Prisms", Applied Optics, Sep. 1, 2011, vol. 50, No. 25, pp. 5012-5022.

Hagen et al., "Compound Prism Design Principles, III: Linear-in-Wavenumber and Optical Coherence Tomography Prisms", Applied Optics, Sep. 1, 2011, vol. 50, No. 25, pp. 5023-5030.

Hagen et al., "Fourier Methods of Improving Reconstruction Speed for CTIS Imaging Spectrometers", Imaging Spectrometry XII, Proceedings of SPIE vol. 6661, 2007, pp. 11.

Hagen et al., "Foveated Endoscopic Lens", Journal of Biomedical Optics, Feb. 2012, vol. 17, No. 2, pp. 021104-1-021104-6.

Hagen et al., "Gaussian Profile Estimation in One Dimension", Applied Optics, Aug. 1, 2007, vol. 46, No. 22, pp. 5374-5383.

Hagen et al., "Gaussian Profile Estimation in Two Dimension", Applied Optics, Dec. 20, 2008, vol. 47, No. 36, pp. 6842-6851.

Hagen et al., "Quantitative Sectioning and Noise Analysis for Structured Illuminatio Microscopy", Optics Express, Jan. 2, 2012, vol. 20, No. 1, pp. 403-413.

Hagen et al., "Quantitative Sectioning and Noise Analysis for Structured Illumination Microscopy: Errata", Optics Express, Feb. 27, 2012, vol. 20, No. 5, pp. 5343.

Hagen et al., "Real-Time Quantiatative Hydrocarbon Gas Imaging with the Gas Cloud Imager (GCI)", Proceedings of SPIE, Vo.. 8358, Chemical, Biological, Radiologica, Nuclear, and Explosives (CBRNE) Sensing XIII, May 1, 2012, pp. 7.

Hagen et al., "Review of Snapshot Spectral Imaging Technologies", Optical Engineering, Sep. 2013, vol. 52, No. 9, pp. 090901-1-090901-23.

Hagen et al., "Snapshot Advantage: A Review of the Light Collection Improvement for Parallel High-Dimensional Measurement Systems," Optical Engineering, Jun. 13, 2012, vol. 51, No. 11, p. 111702-1-111702-7.

Hagen et al., "Snapshot Mueller Matrix Spectropolarimeter" Optics Letters, Aug. 1, 2007, vol. 32, No. 15, pp. 2100-2102.

Hagen et al., "Spectrally-Resolved Imaging of Dynamic Turbid Media", Multimodal Biomedical Imaging VI, Proceedings of SPIE vol. 7892, 2011, pp. 1-7.

Hagen et al., "Video-Rate Spectral Imaging of Gas Leaks in the Longwave Infrared," Chemical, Biological, Radiological, Nuclear, and Explosives (CBRNE) Sensing XIV, May 29, 2013, SPIE Proceedings vol. 8710, pp. 7.

Harley et al., "Remote Quantification of Smokestack Effluent Mass Flow Rates Using Imaging Fourier Transform Spectrometry," Chemical, Biological, Radiological, Nuclear, and Explosives (CBRNE) Sensing XII, Apr. 25-29, 2011, SPIE Proceedings vol. 8018, pp. 1-13.

Hayden et al., "Determination of Trace-Gas Amounts in Plumes by the Use of Orthogonal Digital Filtering of Thermal•-Emission Spectra", Applied Optics, Jun. 1, 1996, vol. 35, No. 16, pp. 2802-2809.

Hirsch et al., "Detection of Gaseous Plumes in IR Hyperspectral Images Using Hierarchical Clustering", Applied Optics, Sep. 1, 2007, vol. 46, No. 25, pp. 6368-6374.

International Preliminary Reporton Patentability in PCT Application No. PCT/US2013/041278 (REBPH.001WO) dated Nov. 27, 2014 in 10 pages.

International Preliminary Reporton Patentability in PCT Application No. PCT/US2016/034455 (REBPH.008WO) dated Dec. 5, 2017 in 8 pages.

International Preliminary Reporton Patentability in PCT Application No. PCT/US2017/057712 (REBPH.012WO) dated May 2, 2019 in 9 pages.

International Preliminary Reporton Patentability in PCT Application No. PCT/US2017/057725 (REBPH.010WO) dated May 2, 2019 in 10 pages.

International Preliminary Reporton Patentability in PCT Application No. PCT/US2018/019271 (REBPH.013WO) dated Sep. 6, 2019 in 11 pages.

International Preliminary Reporton Patentability received for PCT Patent Application No. PCT/US2018/059890, dated May 22, 2020, 8 pages.

International Search Report and Written Opinion received for PCT Patent Application No. PCT/US2017/057712, dated Mar. 6, 2018, 11 pages.

International Search Report and Written Opinion received for PCT Patent Application No. PCT/US2017/057725, dated Feb. 14, 2018, 13 pages.

International Search Report and Written Opinion received for PCT Patent Application No. PCT/US2018/019271, dated Jun. 27, 2018, 14 pages.

International Search Report and Written Opinion received for PCT Patent Application No. PCT/US2018/059890, dated Jan. 23, 2019, 9 pages.

International Search Report in PCT Application No. PCT/US2013/041278 (REBPH.001WO) dated Aug. 27, 2013 in 4 pages.

International Search Report in PCT Application No. PCT/US2016/034455 (REBPH.008WO) dated Oct. 24, 2016 in 12 pages.

Interview Summary received in U.S. Appl. No. 14/543,692 (REBPH.001CI) dated Feb. 17, 2016 in 5 pages.

Interview Summary received in U.S. Appl. No. 15/789,811 (REBPH.010A) dated Nov. 20, 2018 in 3 pages.

Interview Summary received in U.S. Appl. No. 15/789,829 (REBPH.012A) dated Feb. 26, 2020 in 3 pages.

Invitation to Pay Additional Fees in PCT Application No. PCT/US2017/057712 (REBPH.012WO) dated Jan. 10, 2018 in 2 pages.

Invitation to Pay Additional Fees in PCT Application No. PCT/US2017/057725 (REBPH.010WO) dated Dec. 14, 2017 in 3 pages.

Johnston et al., "A Real-Time FPGA Impiementation of a Barrel Distortion Correction Algorithm", Projects, 2003, vol. 10, pp. 91-96.

Karion et al., "Methane Emissions Estimate from Airborne Measurements Over a Western United States Natural Gas Field", Geophysical Research Letters, 2013, vol. 40, pp. 4393-4397.

Keshava et al., "A Survey of Spectral Unmixing Algorithms", Lincoln Laboratory Journal, 2003, vol. 14, No. 1, pp. 55-78.

(56) References Cited

OTHER PUBLICATIONS

Kester et al., "A Real-Time Gas Cloud Imaging Camera for Fugitive Emission Detection and Monitoring", Imaging and Applied Optics Technical Digest, 2012, pp. 3.
Kester et al., "Development of Image Mappers for Hyperspectral Biomedical Imaging Applications", Applied Optics, Apr. 1, 2010, vol. 49, No. 10, pp. 1886-1899.
Kester et al., "High Numerical Aperture Microendoscope Objective for a Fiber Confocal Reflectance Microscope", Optics Express, Mar. 5, 2007, vol. 15. No. 5, pp. 2409-2420.
Kester et al., "Low Cost, High Performance, Self-Aligning Miniature Optical Systems", Applied Optics, Jun. 20, 2009, vol. 48, No. 18, pp. 3375-3384.
Kester et al., "Real-Time Snapshot Hyperspectral Imaging Endoscope", Journal of Biomedical Optics, May 2011, vol. 16, No. 5, pp. 056005-1-056005-12.
King et al., "Airborne Scanning Spectrometer for Remote Sensing of Cloud, Aerosol, Water Vapor, and Surface Properties", Journal of Atmospheric and Oceanic Technology, Aug. 1996, vol. 13, No. 4, pp. 777-794.
Kudenov et al., "Fourier Transform Channeled Spectropoiarimetly in the MWIR", Optics Express, Oct. 1, 2007, vol. 15, No. 20, pp. 12792-12805.
Kudenov et al., "Snapshot Imaging Mueller Matrix Polarimeter Using Polarization Gratings", Optics Letters, Apr. 15, 2012, vol. 37, No. 8, pp. 1367-1369.
Landau et al., "Design and Evaluation of an Ultra-Slim Objective for in-vivo Deep Optical Biopsy", Optics Express, Mar. 1, 2010, vol. 18, No. 5, pp. 4758-4775.
Levi, Michael A., "Comment on 'Hydrocarbon Emissions Characterization in the Colorado Front Range: A Pilot Study' by Gabrielle Petron et al.", Journal of Geophysical Research, 2012, vol. 117, No. D21203, pp. 1-5.
Levi, Michael A., "Reply to "'Reply to 'Comment on 'Hydrocarbon Emissions Characterization in the Colorado Front Range—A Pilot Study' by Michael A. Levi" by Gabrielle Petron et al.", Journal of Geophysical Research: Atmospheres, 2013, vol. 118, pp. 3044-3046.
Low et al., "Remote Sensing and Characterization of Stack Gases by Infrared Spectroscopy. An Approach by Using Multiple-Scan Interferometry", Environmental Science & Technology, Jan. 1967, vol. 1, No. 1, pp. 73-74.
Luo et al., "Fast Processing of Imaging Spectrometer Data Cube Based on FPGA Design", MIPPR 2007: Multispectral Image Processing, Proceedings of SPIE vol. 6787, pp. 7.
Manolakis et al., "Long-Wave Infrared Hyperspectral Remote Sensing of Chemical Clouds", IEEE Signal Processing Magazine, Jul. 2014, vol. 31, No. 4, pp. 120-141.
Mathews, "Design and Fabrication of a Low-Cost, Multispectral Imaging System," Applied Optics, 2008, pp. F71-F76, vol. 47.
Naranjo et al., "IR Gas Imaging in an Industrial Setting," Thermosense XXXII, Published in SPIE Proceedings vol. 7661, May 4, 2010, pp. 1-8.
Nguyen et al., "Snapshot 3D Optical Coherence Tomography System using Image Mapping Spectrometer", Biomedical Optics and 3D Imaging OSA, 2012, pp. 3.
Niu et al., "New Approach to Remote Gas-Phase Chemical Quantification: Selected-Band Algorithm", Optical Engineering, Feb. 2014, vol. 53, No. 2, pp. 021111-1-021111-10.
Non-Final Office Action Response as filed in U.S. Appl. No. 14/538,827 (REBPH.001A2) dated Dec. 28, 2015 in 11 pages.
Non-Final Office Action Response as filed in U.S. Appl. No. 14/539,899 (REBPH.001PI) dated Aug. 26, 2015 in 8 pages.
Non-Final Rejection dated Aug. 4, 2020 for U.S. Appl. No. 15/902,336.
Non-Final Rejection dated Feb. 6, 2020 for U.S. Appl. No. 15/902,336.
Non-Final Rejection dated Jun. 1, 2020 for U.S. Appl. No. 16/530,232.
Notice of Allowance and Fees Due (PTOL-85) dated Jul. 6, 2020 for U.S. Appl. No. 16/138,823.
Notice of Allowance and Fees Due (PTOL-85) dated Jul. 22, 2020 for U.S. Appl. No. 16/664,615.
Notice of Allowance and Fees Due (PTOL-85) dated May 29, 2020 for U.S. Appl. No. 16/256,967.
Notice of Allowance and Fees Due (PTOL-85) dated Nov. 12, 2020 for U.S. Appl. No. 15/902,336.
Notice of Allowance received in U.S. Appl. No. 14/543,692 dated Dec. 9, 2016 in 12 pages.
Notice of Allowance received in U.S. Appl. No. 14/792,477 dated Apr. 19, 2018 in 13 pages.
Adams, et al., "Advances in Detectors: Hot IR sensors improve IR camera size, weight, and power", Laser Focus World, vol. 50, Issue 1, Jan. 17, 2014, 6 pages. Also available at http://www.ircameras.com/articles/advances-detectors-hot-ir-sensors-impro-ve-ir-camera-size-weight-power.
Allen et al., "Measurements of Methane Emissions at Natural Gas Production Sites in the United States", PNAS, Oct. 29, 2013, vol. 110, No. 44, pp. 7.
Alvarez et al., "Greater Focus Needed on Methane Leakage from Natural Gas Infrastructure", PNAS, Apr. 24, 2012, vol. 109, No. 17, pp. 12.
Amendment After Allowance as fiied in U.S. Appl. No. 15/471,398 (REBPH.001C2) dated , Jan. 24, 2019 in 5 pages.
Amendment after Allowance as filed in U.S. Appl. No. 14/543,692 (REBPH.001CI) dated Mar. 3, 2017 in 6 pages.
Amendment after Allowance as filed in U.S. Appl. No. 15/418,532 (REBPH.001A2C1) dated Sep. 14, 2018 in 6 pages.
Amendment as filed in U.S. Appl. No. 14/538,827 (REBPH.001A2) dated Dec. 16, 2016 in 9 pages.
Amendment as filed in U.S. Appl. No. 14/539,899 (REBPH.001PI) dated Jan. 27, 2017 in 5 pages.
Amendment as filed in U.S. Appl. No. 14/539,899 (REBPH.001PI) dated Jun. 9, 2016 in 6 pages.
Amendment as filed in U.S. Appl. No. 14/700,567 (REBPH.004A) dated Dec. 13, 2017 in 12 pages.
Amendment as filed in U.S. Appl. No. 14/700,567 (REBPH.004A) dated Jul. 5, 2018 in 10 pages.
Amendment as filed in U.S. Appl. No. 14/792,477 (REBPH.005A) dated Jan. 18, 2018 in 10 pages.
Amendment as filed in U.S. Appl. No. 15/166,092 (REBPH.008A) dated Nov. 15, 2018 in 11 pages.
Amendment as filed in U.S. Appl. No. 15/418,532 (REBPH.001A2CI) dated Nov. 22, 2017 in 8 pages.
Amendment as filed in U.S. Appl. No. 15/462,352 (REBPH.001P1C1) dated Apr. 30, 2019 in 5 pages.
Amendment as filed in U.S. Appl. No. 15/462,352 (REBPH.001P1C1) dated Aug. 21, 2019 in 5 pages.
Amendment as filed in U.S. Appl. No. 15/462,352 (REBPH.001P1C1) dated Feb. 28, 2018 in 5 pages.
Amendment as filed in U.S. Appl. No. 15/789,811 (REBPH.010A) dated Jan. 25, 2019 in 7 pages.
Amendment as filed in U.S. Appl. No. 15/789,829 (REBPH.012A) dated Dec. 4, 2018 in 9 pages.
Amendment as filed in U.S. Appl. No. 15/789,829 (REBPH.012A) dated May 24, 2019 in 7 pages.
Amendment as filed in U.S. Appl. No. 16/138,823 (REBPH.003C2) dated Nov. 14, 2019 in 6 pages.
Amendment as filed in U.S. Appl. No. 16/185,399 (REBPH.014A) dated Jul. 2, 2019 in 7 pages.
Amendment as filed in U.S. Appl. No. 16/530,232 (REBPH.OIOCI) dated Jan. 13, 2020 in 6 pages.
Amendment as filed in U.S. Appl. No. 16/549,297 (REBPH.001P1C2) dated Jan. 13, 2020 in 5 pages.
Amendment as filed in U.S. Appl. No. 16/661,407 (REBPH.005CI) dated Jan. 13, 2020 in 5 pages.
Amendment as filed in U.S. Appl. No. 16/664,615 (REBPH.014C1) dated Jan. 16, 2020 in 5 pages.
Annex to the communication dated Jan. 3, 2017 for EP Application No. 15165877.
Anonymous: "LeonardoDRS" Jan. 1, 2012 (Jan. 1, 2012), XP055683152 Retrieved from the Internet URL:https://www.leonardodrs.com/media/10437/2019 u8000 -mr-2012-04-618 rev04.pdf.
Applicant-Initiated Interview Summary received in U.S. Appl. No. 14/792,477 dated Oct. 23, 2019, 3 pages.

(56) References Cited

OTHER PUBLICATIONS

ARPA-E, "Portable Methane Detection System", dated Dec. 16, 2014 (including innovation update from May 2018) in 2 pages https://arpa-e, energy.gov/?q=slick-sheet-project/portable-mathane-detection-system.
ARPA-E, "Wearable, Continuously Monitoring Methane Imagers", as updated Jan. 15, 2018 in 2 pages https://arpa-e.energy.gov/sites/default/files/Rebellion-MONITOR-May1.pdf.
Bedard et al., "Image Mapping Spectrometry: Calibration and Characterization", Optical Engineering, Nov. 2012, vol. 51, No. 11, pp. 111711-1-111711-13.
Ben-David et al., "Probability Theory for 3-Layer Remote Sensing Radiative Transfer Model: Errata," Optics Express, May 20, 2013, vol. 21, No. 10, pp. 11852.
Ben-David et al., "Probability Theory for 3-Layer Remote Sensing Radiative Transfer Model: Univariate Case," Optics Express, Apr. 2012, vol. 20, No. 9, pp. 10004-10033.
Brady et al., "Multiscale Lens Design", Optics Express, Jun. 22, 2009, vol. 17, No. 13, pp. 10659-10674.
Brochure provided by Lofty Designs to Rebellion Photonics on Oct. 31, 2012 as noted from the email. Subsequent to that date brochure was used in connection with potential customers.
Catanzaro, et al., "Design of Dual-Band SWIR/MWIR and MWIR/LWIR Imagers", Proceedings of SPIE 5406, Infrared Technology and Applications XXX, Aug. 30, 2004, pp. 829-835.
Caulton et al., "Toward a Better Understanding and Quantification of Methane Emissions from Shale Gas Development", PNAS, Apr. 29, 2014, vol. 111, No. 17, pp. 7.
Chen et al., "Quantitative Sectioning and Noise Analysis for Structured Illumination Microscopy: Erratum", Optics Express, Oct. 19, 2015, vol. 23, No. 21, pp. 27633-27634.
Chidley et al., "Flow-Induced Birefringence: The Hidden PSF Killer in High Performance Injection-Molded Plastic Optics", Endoscopic Microscopy, Proceedings of SPIE vol. 6082, 2006, pp. 11.
Chu et al., "The NIST Quantitative Infrared Database", Journal of Research of the National Institute of Standards and Technology, Jan.-Feb. 1999, vol. 104, No. 1, pp. 59-81.
Comments on Allowance filed in U.S. Appl. No. 14/700,791 {REBPH.003A) dated May 19, 2017 in 2 pages.
Comments on Allowance flied in U.S. Appl. No. 15/623,942 (REBPH.003C1) dated Aug. 23, 2018 in 2 pages.
Communication Pursuant to Rules 161(2) and 162 for European Application No. 18875450.1 dated Jun. 17, 2020, 3 pages.
Corrected Notice of Allowance received in U.S. Appl. No. 14/538,827 (REBPH.001A2) dated Feb. 10, 2016 in 4 pages.
Corrected Notice of Allowance received in U.S. Appl. No. 14/538,827 (REBPH.001A2) dated Feb. 22, 2016 in 4 pages.
Corrected Notice of Allowance received in U.S. Appl. No. 15/418,532 (REBPH.001A2C1) dated Jul. 6, 2018 in 3 pages.
Cossel, et al., "Analysis of Trace Impurities in Semiconductor Gas via Cavity-Enhanced Direct Frequency Comb Spectroscopy", Applied Physics B, Sep. 2010, vol. 100, No. 4, pp. 917-924.
Decision to Refuse dated Apr. 19, 2018 for EP Application No. 15165877.0.
DiPietro et al., "Hyperspectral Matched Filter with False-Alarm Mitigation", Optical Engineering, Jan. 2012, vol. 51, No. 1, pp. 016202-1-016202-7.
U.S. Appl. No. 15/902,336, filed Feb. 22, 2018, now U.S. Pat. No. 10,955,355.
Weldon et al., "H2S and CO2 gas sensing using DFB laser diodes emitting at 1.57 μm", Sensors and Actuators B: Chemical, Oct. 1995, vol. 29, Issues 1-3, pp. 101-107.
Wikipedia entry https://en.wikipedia.org/wiki/Mobile_computing last modified on Dec. 30, 2016; retrieved from the internet on Feb. 2, 2017 in 6 pages.
Williams et al. ("Dual-Band MWIR/LWIR Radiometer for Absolute Temperature Measurements", Thermosense XXVII Edited by Jonathan Miles et al., Proc. of SPIE, vol. 6205, pp. 62050M-1 to 62050M-13 (2006).
Young et al., "An In-Scene Method for Atmospheric Compensation of Thermal Hyperspectral Data", Journal of Geophysical Research, 2002, vol. 107, No. D24, pp. 14-1-14-20.
Zheng et al., "A Static Multiplex Fabry-Perot Spectrometer", Sensors, Cameras, and Systems for Industrial/Scientific Applications X, Proceedings of SPIE-IS&T Electronic Imaging, SPIE vol. 7249, 2009, pp. 8.
Zheng et al., "Analytic-Domain Lens Design with Proximate Ray Tracing", Journal of the Optical Society of America A, Aug. 2010, vol. 27, No. 8, pp. 1791-1802.
Notice of Allowance received in U.S. Appl. No. 14/792,477 dated Jan. 30, 2019 in 11 pages.
Notice of Allowance received in U.S. Appl. No. 14/792,477 dated Jun. 21, 2019 in 10 pages.
Notice of Allowance received in U.S. Appl. No. 14/792,477 dated Sep. 20, 2018 in 14 pages.
Notice of Allowance received in U.S. Appl. No. 14/538,827 (REBPH.001A2) dated Feb. 1, 2016 in 18 pages.
Notice of Allowance received in U.S. Appl. No. 14/538,827 (REBPH.001A2) dated May 26, 2016 in 9 pages.
Notice of Allowance received in U.S. Appl. No. 14/538,827 (REBPH.001A2) dated Sep. 19, 2016 in 9 pages.
Notice of Allowance received in U.S. Appl. No. 14/539,899 (REBPH.001PI) dated Jun. 21, 2016 in 17 pages.
Notice of Allowance received in U.S. Appl. No. 14/539,899 (REBPH.001PI) dated Oct. 31, 2016 in 10 pages.
Notice of Allowance received in U.S. Appl. No. 14/543,692 (REBPH.001CI) dated Mar. 17, 2017 in 4 pages.
Notice of Allowance received in U.S. Appl. No. 14/571,398 (REBPH.001C2) dated Feb. 7, 2018 in 20 pages.
Notice of Allowance received in U.S. Appl. No. 14/571,398 (REBPH.001C2) dated Jul. 2, 2018 in 8 pages.
Notice of Allowance received in U.S. Appl. No. 14/571,398 (REBPH.001C2) dated Oct. 18, 2017 in 8 pages.
Notice of Allowance received in U.S. Appl. No. 14/571,398 (REBPH.001C2) dated Oct. 24, 2018 in 7 pages.
Notice of Allowance received in U.S. Appl. No. 14/700,791 (REBPH.003A) dated Feb. 21, 2017 in 20 pages.
Notice of Allowance received in U.S. Appl. No. 14/700,791 (REBPH.003A) dated Jul. 10, 2017 in 24 pages.
Notice of Allowance received in U.S. Appl. No. 14/700,791 (REBPH.003A) dated Jun. 9, 2016 in 11 pages.
Notice of Allowance received in U.S. Appl. No. 14/700,791 (REBPH.003A) dated Sep. 30, 2016 in 19 pages.
Notice of Allowance received in U.S. Appl. No. 15/166,092 (REBPH.008A) dated Oct. 18, 2019 in 19 pages.
Notice of Allowance received in U.S. Appl. No. 15/418,532 (REBPH.001A2C1) dated Dec. 5, 2018 in 11 pages.
Notice of Allowance received in U.S. Appl. No. 15/418,532 (REBPH.001A2C1) dated Jun. 15, 2018 in 12 pages.
Notice of Allowance received in U.S. Appl. No. 15/462,350 (REBPH.001P1C1) dated May 23, 2019,2019 in 10 pages.
Notice of Allowance received in U.S. Appl. No. 15/462,352 (REBPH.001P1C1) dated Feb. 12, 2019 in 9 pages.
Notice of Allowance received in U.S. Appl. No. 15/462,352 (REBPH.001P1C1) dated Jul. 17, 2018 in 25 pages.
Notice of Allowance received in U.S. Appl. No. 15/462,352 (REBPH.001P1C1) dated Oct. 31, 2018 in 9 pages.
Notice of Allowance received in U.S. Appl. No. 15/471,398 (REBPH.001C2) dated Feb. 27, 2019 in 14 pages.
Notice of Allowance received in U.S. Appl. No. 15/471,398 (REBPH.001C2) dated Mar. 6, 2019 in 5 pages.
Notice of Allowance received in U.S. Appl. No. 15/623,942 (REBPH,003C1) dated Jan. 24, 2018 in 22 pages.
Notice of Allowance received in U.S. Appl. No. 15/623,942 (REBPH.003C1) dated May 24, 2018 in 23 pages.
Notice of Allowance received in U.S. Appl. No. 15/789,811 (REBPH.010A) dated Mar. 27, 2019 in 9 pages.
Notice of Allowance received in U.S. Appl. No. 15/789,829 (REBPH.012A) dated Feb. 25, 2019 in 28 pages.
Notice of Allowance received in U.S. Appl. No. 15/789,829 (REBPH.012A) dated Jul. 19, 2019 in 14 pages.

(56) References Cited

OTHER PUBLICATIONS

Notice of Allowance received in U.S. Appl. No. 16/138,823 (REBPH.003C2) dated Jun. 14, 2019 in 10 pages.
Notice of Allowance received in U.S. Appl. No. 16/138,823 (REBPH.003C2) dated Mar. 12, 2020 in 28 pages.
Notice of Allowance received in U.S. Appl. No. 16/185,399 (REBPH.014A) dated Jul. 26, 2019 in 9 pages.
Notice of Allowance received in U.S. Appl. No. 16/185,399 (REBPH.014A) dated Nov. 7, 2019 in 8 pages.
Notice of Allowance received in U.S. Appl. No. 16/256,967 (REBPH.004C1) dated Feb. 18, 2020 in 7 pages.
Notice to File Corrected Application Papers received in U.S. Appl. No. 15/462,352 (REBPH.001P1C1) dated Aug. 8, 2018 in 3 pages.
Office Action as filed in U.S. Appl. No. 14/700,567 (REBPH.004A) dated Aug. 27, 2018 in 36 pages.
Office Action received in U.S. Appl. No. 14/543,692 dated Jun. 1, 2016 in 18 pages.
Office Action received in U.S. Appl. No. 15/789,829 dated Apr. 3, 2020, 27 pages.
Office Action received in U.S. Appl. No. 14/538,827 (REBPH.001A2) dated Jun. 30, 2015 in 8 pages.
Office Action received in U.S. Appl. No. 14/539,899 (REBPH.001P1) dated Mar. 26, 2015 in 6 pages.
Official Communication received in Canadian Application No. 2,873,989 (REBPH.001CA) dated Mar. 21, 2019 in 6 pages.
Official Communication received in Canadian Application No. 2,873,989 (REBPH.OOICA) dated Mar. 2, 2020 in 4 pages.
Official Communication received in European Application No. 13732285.5 (REBPH.001 EP) dated Sep. 10, 2019 in 6 pages.
Official Communication received in European Application No. 13732285.5 (REBPH.001EP) dated Jul. 26, 2018 in 6 pages.
Official Communication received in European Application No. 14192862.2 (REBPH.001EP2) dated Apr. 19, 2016 in 6 pages.
Official Communication received in European Application No. 14192862.2 (REBPH.001EP2) dated May 2, 2018 in 3 pages.
Official Communication received in European Application No. EP 15165880.4 (REBPH.004EP) dated Jul. 5, 2019 in 4 pages.
Official Communication received in U.S. Appl. No. 14/792,477 dated Jan. 27, 2017 in 10 pages.

\* cited by examiner

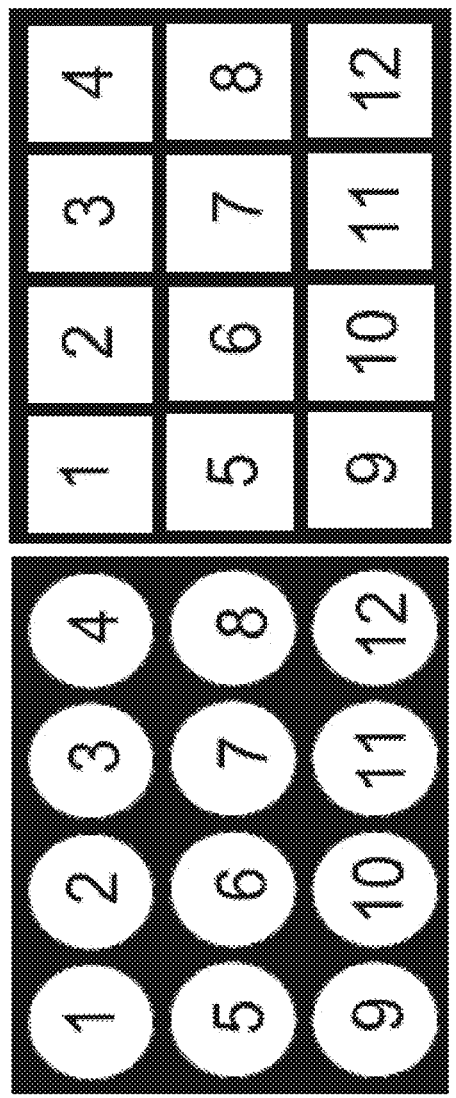

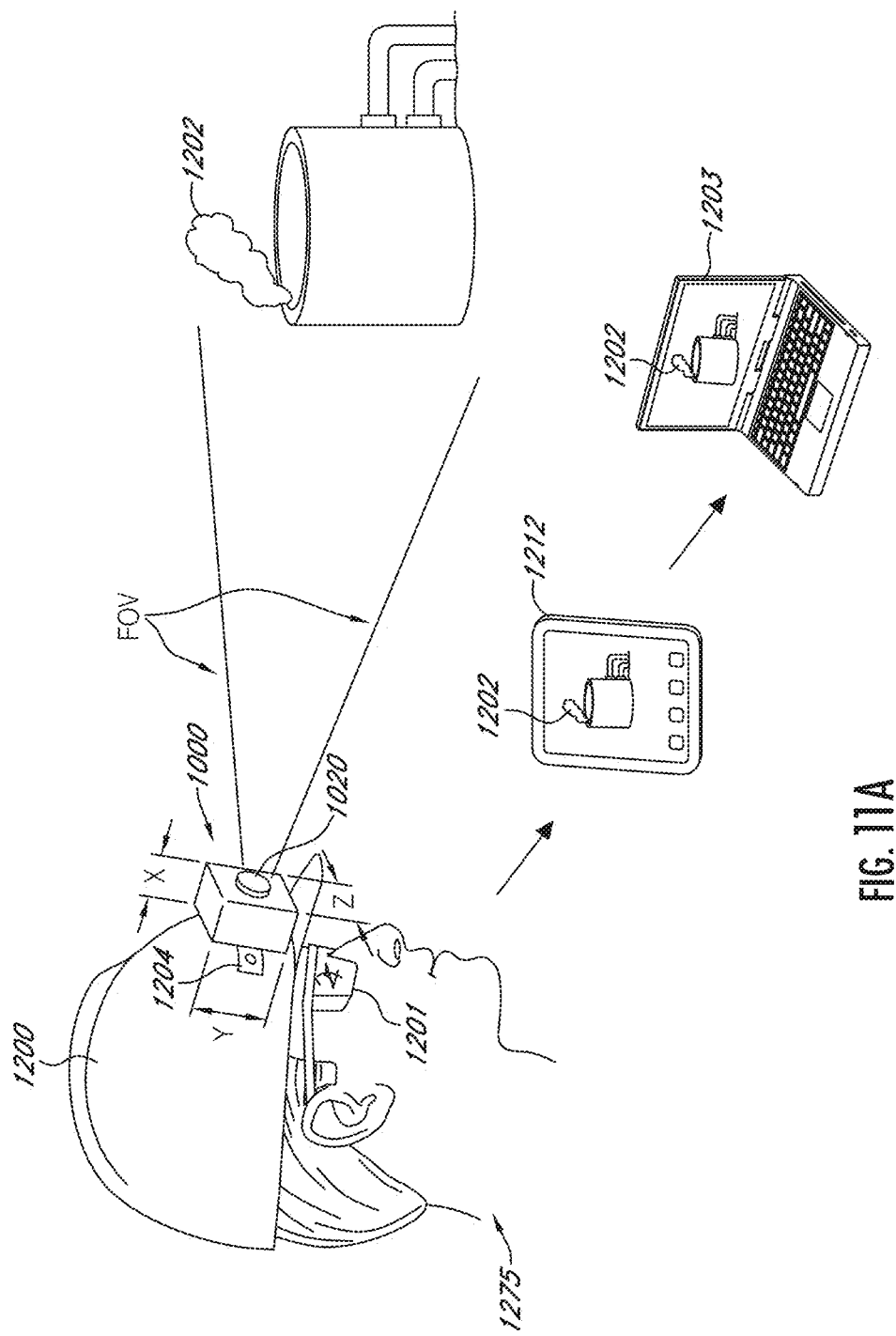

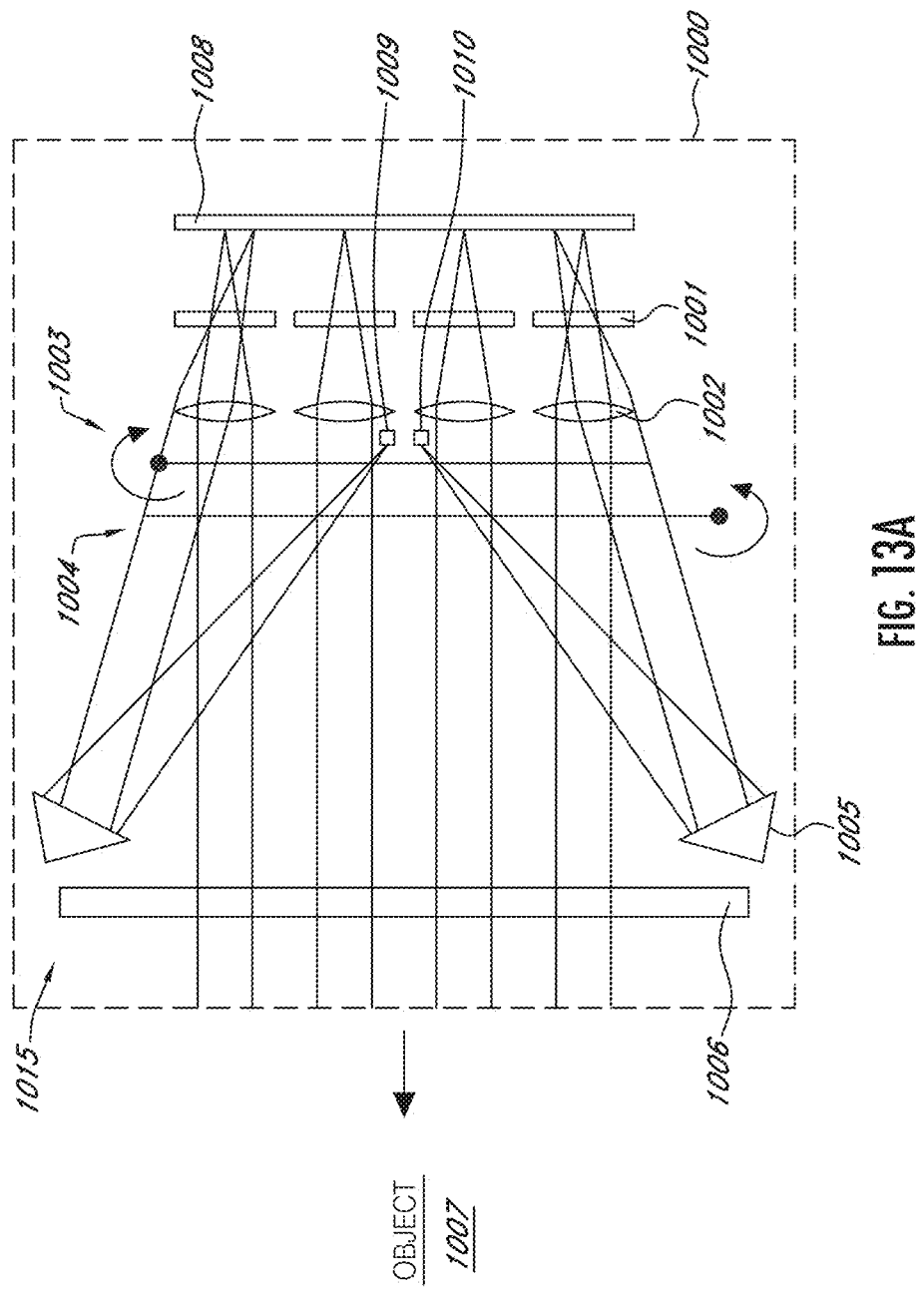

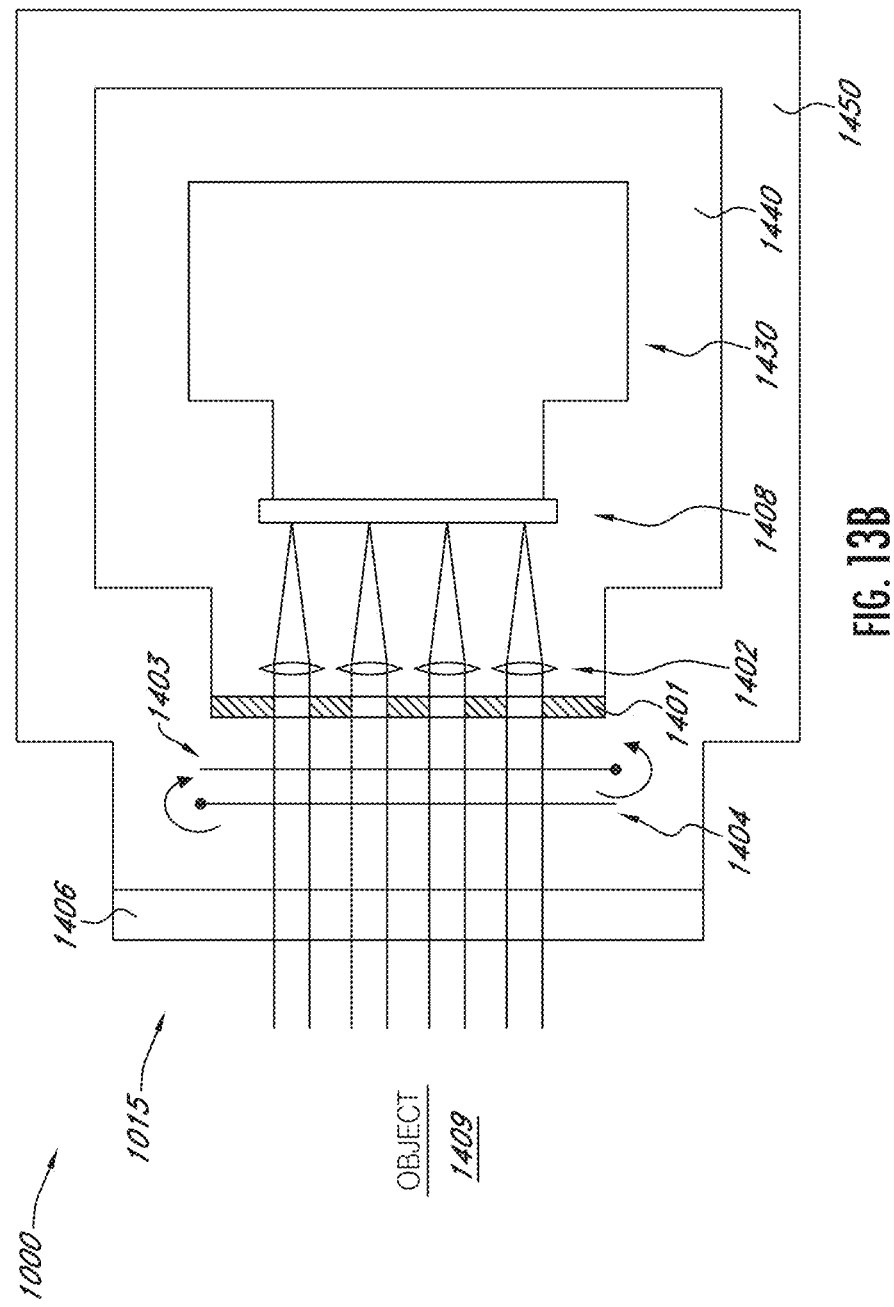

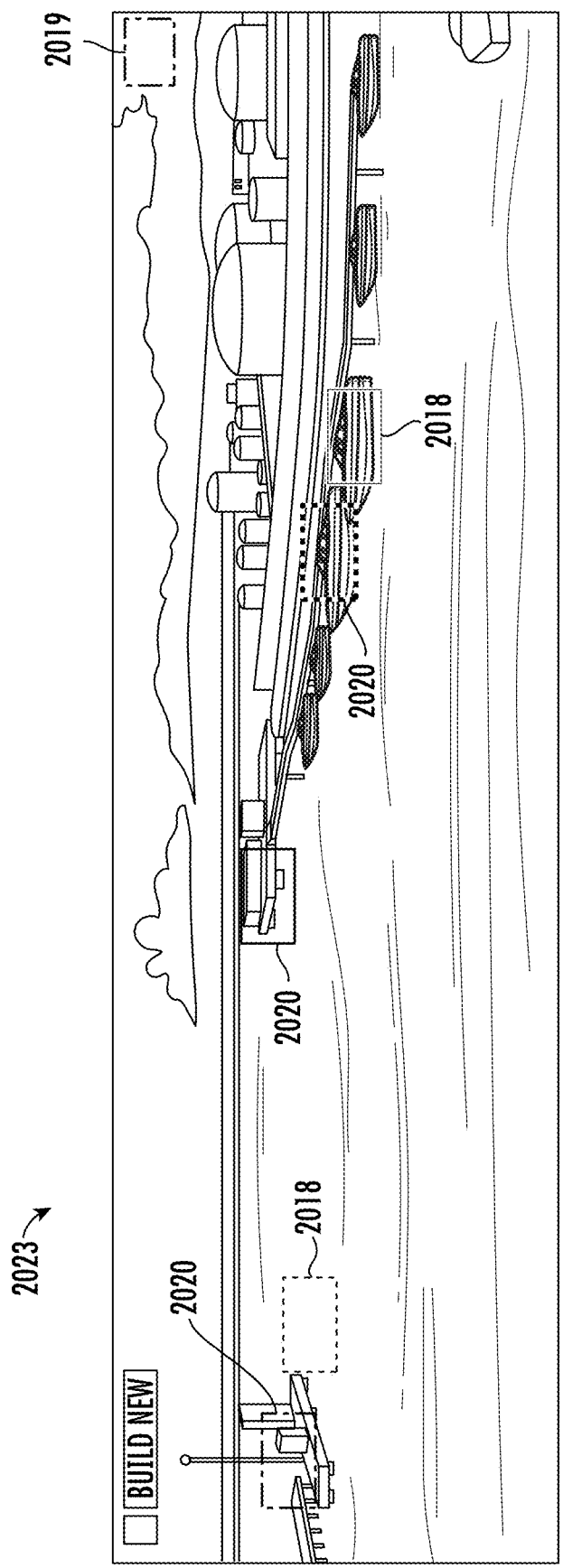

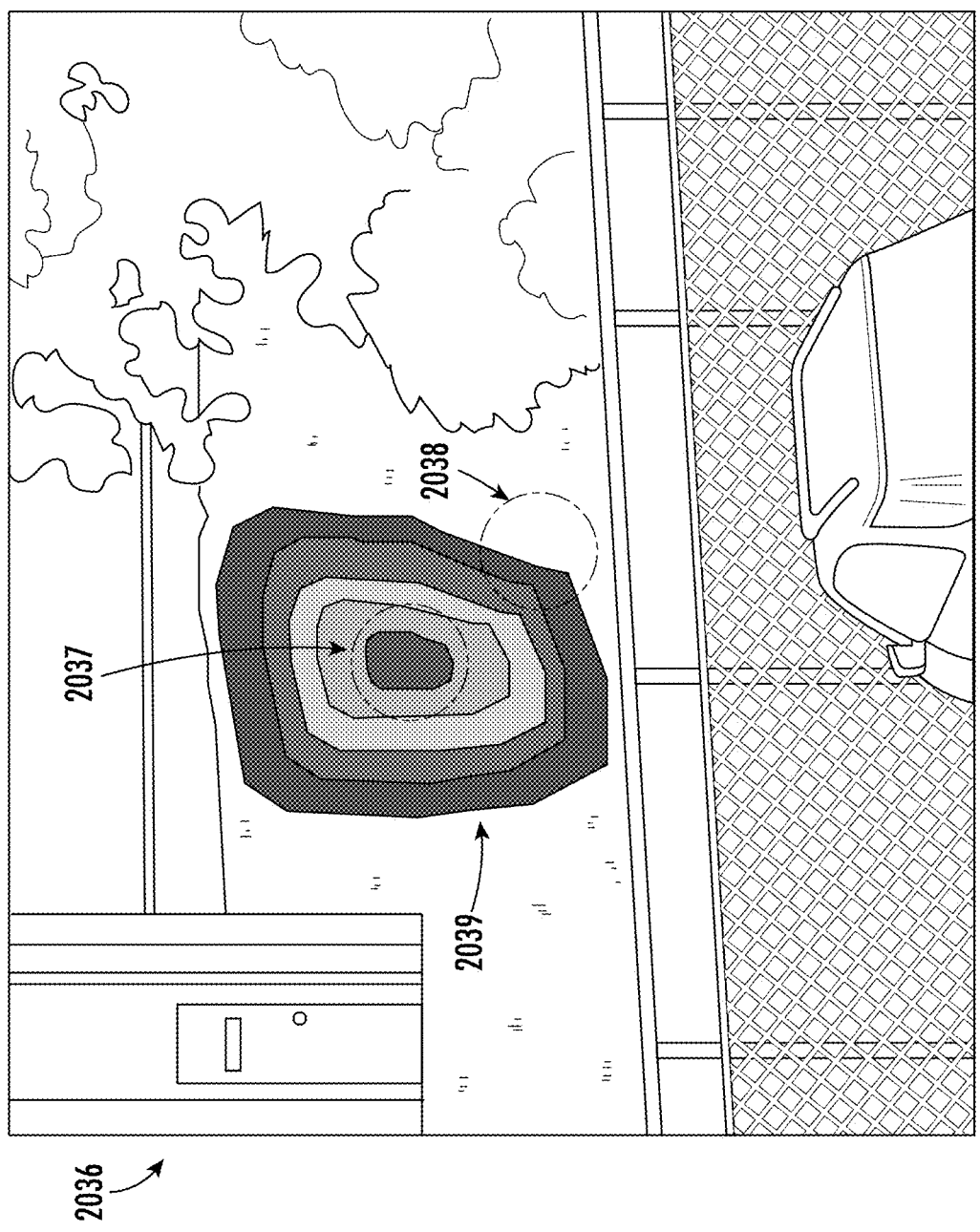

| EVENT ICON | PRIORITY | EVENT TYPE | DESCRIPTION | FULL MESSAGE | APPEARS IN STATUS BAR |
|---|---|---|---|---|---|
| ◇ | HIGH | ALARMING DETECTION | "<GAS> ALERT!" | "<GAS> ALERT AT <FOVNAME>" | ✓ |
| ◇ | HIGH | ALARMING EMULATED DETECTION | "<GAS> ALERT!" | "<GAS> ALERT AT <FOVNAME>" | ✓ |
| ▭ | MEDIUM | WOS DETECTION | "WINDOW OBSCURATION" | "WINDOW OBSCURED, DETECTION IS DISABLED" | ✓ |
| ✂ | MEDIUM | INTRUSION DETECTION | "INTRUSION DETECION" | "INTRUSION DETECTED" | ✓ |
| × | MEDIUM | DISK FULL | "[DATA/ROOT] DRIVE FULL" | "[DATA/ROOT] DRIVE IS OVER 90%" | ✓ |
| × | MEDIUM | DISK FAILURE | "DISK FAILURE" | "DISK FAILURE: A <RAIDNAME> RAID MEMBER FAILED A SMART SELF-TEST. <REPLACEMENT REQUIRED>" | ✓ |
| × | MEDIUM | DISK FAILURE | "DISK FAILURE" | "DISK FAILURE: DISK <DISKNAME>, MOUNTED AT <MOUNT>, IS MOUNTED READ-ONLY. THIS DISK MAY BE FAILING." | ✓ |
| × | MEDIUM | MEMORY WARNING | "MEMORY WARNING" | "MEMORY WARNING: A HARDWARE ISSUE HAS BEEN REPORTED. EXAMINE THE MCE LOG FOR DETAILS." | ✓ |
| × | MEDIUM | BANDWIDTH FAILURE | "BANDWIDTH FAILURE" | "BANDWIDTH FAILURE (<SENSORIP>)" | ✓ |
| × | MEDIUM | PING FAILURE | "PING FAILURE" | "PING FAILURE (<SENSORIP>)" | ✓ |
| × | LOW | HIGH DISK USE | "[DATA/ROOT] DRIVE USAGE" | "[DATA/ROOT] DRIVE IS OVER 70%" | ✓ |
| × | LOW | DISK NOT FOUND | "DATA DRIVE NOT FOUND" | "DISK/DATA DOES NOT SEEM TO EXIST" | ✓ |
| ◇ | DETECTION | GAS DETECTED | "<GAS> DETECTION" | "<GAS> DETECTION" | ✓ |
| ⊕ | DETECTION | LOW THERMAL CONTRAST | "LOW THERMAL CONTRAST" | "LOW THERMAL CONTRAST DETECTED" | ✓ |
| NONE | INFO | MODE CHANGE - ENTER TEST | "CONTROL MODE CHANGED" | "ENTERED TEST MODE" | NO |
| NONE | INFO | MODE CHANGE - RETURN AUTO | "CONTROL MODE CHANGED" | "RETURNING TO AUTOMATIC MODE" | NO |
| NONE | INFO | MODE CHANGE - ENTER MANUAL | "CONTROL MODE CHANGED" | "ENTERED MANUAL MODE" | NO |
| NONE | INFO | MODE CHANGE - EXTEND | "CONTROL MODE CHANGED" | "EXTENDING MANUAL MODE" | NO |
| NONE | INFO | THRESHOLD CHANGES | "DETECTION THRESHOLDS CHANGED" | "DETECTION THRESHOLDS FOR <GAS> WERE CHANGED TO ALARM-THRESHOLD-PPM-M=<VAL1> DETECTION-THRESHOLD-PPM-M=<VAL2>" | NO |
| NONE | INFO | PATH CHANGES | "PATH CHANGED" | "PATH CHANGED" | NO |
| NONE | INFO | ALGORITHIM EMULATED | "<ALGORITHM> [ALERT/DETECTION] EMULATION [ENABLED/DISABLED]" | "<ALGORITHM> [ALERT/DETECTION] EMULATION [ENABLED/DISABLED]" | NO |

FIG. 17B

SYSTEMS AND METHODS FOR MONITORING REMOTE INSTALLATIONS

CROSS-REFERENCE TO RELATED APPLICATIONS

This application is a continuation of U.S. Non-Provisional patent application Ser. No. 15/902,336, filed Feb. 22, 2018, entitled "SYSTEMS AND METHODS FOR MONITORING REMOTE INSTALLATIONS," which claims priority to and the benefit of U.S. Provisional Patent Application No. 62/462,345, filed Feb. 22, 2017, entitled "MONITORING SYSTEM FOR REMOTE FACILITIES;" and U.S. Provisional Patent Application No. 62/462,851, filed Feb. 23, 2017, entitled "SYSTEMS AND METHODS FOR MONITORING REMOTE INSTALLATIONS;" each of which is incorporated herein by reference in its entirety.

FIELD OF THE INVENTION

The present invention generally relates to systems and methods for monitoring remote installations and, in particular, to systems and methods for monitoring fluid leaks at petrochemical installations or facilities.

DESCRIPTION OF THE RELATED TECHNOLOGY

Many petroleum installations (such as drilling or processing sites) may be located in remote locations that are distant from central management offices and monitoring facilities. In these remote installations, chemicals may leak, which can present risks to human users at the installation and/or a reduction in the efficiency of petroleum collection. Accordingly, there remains a continuing need for improved monitoring efforts at petroleum installations.

SUMMARY

The systems, methods and devices of this disclosure each have several innovative aspects, no single one of which is solely responsible for the desirable attributes disclosed herein.

Various examples of optical devices comprising grating structures and their methods of manufacturing are described herein such as the examples enumerated below:

Example 1. A system for monitoring a petrochemical installation, the system comprising:
  an optical imaging system comprising an array of optical detectors; and
  processing electronics configured to process image data detected by the optical imaging system, the processing electronics configured to:
  detect a target species based at least in part on the processed image data; and
  based on a detected amount of the target species, transmit an alarm notification to an external computing device over a communications network indicating that the target species has been detected at the petrochemical installation.

Example 2. The system of Example 1, wherein the processing electronics are configured to detect the target species over multiple frames of the image data and to combine the multiple frames of image data into a summary alarm image that presents the detection of the target species over a period of time.

Example 3. The system of Example 2, wherein the summary alarm image comprises a single image.

Example 4. The system of Example 2, wherein the summary alarm image comprises a plurality of images.

Example 5. The system of any one of Examples 2 to 4, wherein the processing electronics are configured to create the summary alarm image by calculating an average concentration of the target species and/or an average of the image data representative of the concentration over the period of time.

Example 6. The system of any one of Examples 2 to 5, wherein the processing electronics are configured to generate a progressive mode to sequentially present summary alarm images for successive stored fields of view (FOVs).

Example 7. The system of any one of Examples 1 to 6, wherein the processing electronics are configured to create an events log comprising a plurality of events comprising one or more target species detected by the processing electronics.

Example 8. The system of Example 7, wherein the processing electronics are configured to analyze the events log, and based on the analysis, to transmit a priority ranking of events to the external computing device.

Example 9. The system of any one of Examples 7 to 8, wherein the processing electronics are configured to associate multiple events with one another and to form a group of the associated multiple events.

Example 10. The system of Example 9, wherein the processing electronics are configured to form the group of the associated multiple events based at least in part on at least one of event type, type of the detected one or more target species, event time, and a field of view (FOV) in which the one or more target species has been detected.

Example 11. The system of any one of Examples 1 to 10, wherein the processing electronics are configured to compare the detected amount of the target species to a threshold amount and, based on that comparison, transmit the alarm notification to the external computing device over the communications network indicating that the target species has been detected at the petrochemical installation.

Example 12. The system of Example 11, wherein the threshold amount is in a range of 1 ppm-m to 1000 ppm-m of the target species.

Example 13. The system of Example 12, wherein the threshold amount is in a range of 25 ppm-m to 1000 ppm-m of the target species.

Example 14. The system of Example 13, wherein the threshold amount is in a range of 25 ppm-m to 750 ppm-m of the target species.

Example 15. The system of any one of Examples 1 to 14, wherein the target species comprises methane.

Example 16. The system of any one of Examples 1 to 15, wherein the target species comprises hydrogen sulfide.

Example 17. The system of any one of Examples 1 to 16, wherein the target species comprises a gas.

Example 18. The system of any one of Examples 1 to 16, wherein the target species comprises a liquid.

Example 19. The system of any one of Examples 1 to 18, wherein the processing electronics are configured to detect an unauthorized intrusion of an animal (including a human) into the petroleum installation and, based on the detection, to transmit a second alarm notification to the external computing device over the communications network indicating the unauthorized intrusion.

Example 20. The system of any one of Examples 1 to 19, wherein the communications network comprises a wireless communications network.

Example 21. The system of Example 20, wherein the wireless communications network comprises a cellular communications network.

Example 22. The system of Example 21 wherein the wireless communications network is configured to transmit processed image data to the external computing device at speeds in a range of 0.1 Mbps to 10 Mbps.

Example 23. The system of Example 22, wherein the wireless communications network is configured to transmit processed image data to the external computing device at speeds in a range of 0.5 Mbps to 2 Mbps.

Example 24. The system of any one of Examples 1 to 23, wherein the communications network comprises an Ethernet communications network.

Example 25. The system of any one of Examples 1 to 24, wherein the processing electronics are configured to transmit information about one or more events detected at the petrochemical installation to the external computing device, the external computing device configured to generate a user interface presentable to a user on a display device.

Example 26. The system of Example 25, wherein the user interface comprises a visible image window and an infrared image window.

Example 27. The system of any one of Examples 1 to 26, wherein the optical imaging system comprises an infrared (IR) detector array.

Example 28. The system of any one of Examples 1 to 27, wherein the optical imaging system comprises a visible light detector array.

Example 29. The system of any one of Examples 27 to 28, wherein the optical imaging system defines a plurality of optical channels being spatially and spectrally different from one another, each of the plurality of optical channels positioned to transfer radiation incident on the optical imaging system towards the array of optical detectors.

Example 30. The system of Example 29, wherein the optical imaging system and the processing electronics are contained together in a data acquisition and processing module configured to be worn or carried by a person.

Example 31. The system of Example 29, wherein the optical imaging system and the processing electronics are configured to be mounted to a support structure at the petroleum installation.

Example 32. The system of any one of Examples 1 to 31, wherein the optical system comprises a plurality of spectrally distinct infrared optical filters.

Example 33. The system of any one of Examples 1 to 32, wherein the processing electronics are configured to monitor a progression of a liquid leak over a period of time.

Example 34. The system of Example 33, wherein the processing electronics are configured to generate a color map of the progression of the liquid leak based on a length of residence time of the liquid leak at locations of the petrochemical installation.

Example 35. The system of any one of Examples 1 to 34, wherein at least a portion of the processing electronics are located remote from the optical imaging system.

Example 36. The system of any one of Examples 1 to 35, wherein at least a portion of the processing electronics are located on a monitoring computer system.

Example 37. The system of any one of Examples 1 to 36, wherein the processing electronics are configured to generate a system overview image that illustrates locations of a plurality of optical imaging systems at the petrochemical installation, each optical imaging system of the plurality of optical imaging systems associated with an identifier.

Example 38. The system of any one of Examples 1 to 37, wherein the processing electronics are configured to generate a multi-view image that illustrates image data captured by multiple optical imaging systems at multiple sites of one or a plurality of petrochemical installations.

Example 39. The system of any one of Examples 1 to 38, wherein the processing electronics are configured to generate a mosaic image comprising a plurality of fields of view (FOVs) of the optical imaging system at the petrochemical installation.

Example 40. A system for monitoring one or more installations, the system comprising:
  a communications module configured to receive data from one or more optical imaging systems at the one or more installations, the one or more optical imaging systems configured to capture infrared image data at the one or more installations; and
  processing electronics configured to, based on a detected amount of a target species, transmit an alarm notification to an external computing device over a communications network indicating that the target species has been detected at the one or more installations.

Example 41. The system of Example 40, wherein the processing electronics are configured to detect a target species based at least in part on the infrared image data.

Example 42. The system of any one of Examples 40 to 41, wherein the processing electronics are configured to transmit data to the one or more optical imaging systems.

Example 43. The system of any one of Examples 40 to 42, wherein the processing electronics are configured to combine multiple frames of infrared image data into a summary alarm image that presents the detection of the target species over a period of time.

Example 44. The system of Example 43, wherein the summary alarm image comprises a single image.

Example 45. The system of Example 43, wherein the summary alarm image comprises a plurality of images.

Example 46. The system of any one of Examples 43 to 45, wherein the processing electronics are configured to create the summary alarm image by calculating an average concentration of the target species and/or an average of the image data representative of the concentration over the period of time.

Example 47. The system of any one of Examples 43 to 46, wherein the processing electronics are configured to generate a progressive mode to sequentially present summary alarm images for successive fields of view (FOVs) of an optical imaging system of the one or more optical imaging systems.

Example 48. The system of any one of Examples 40 to 47, wherein the processing electronics are configured to create an events log comprising a plurality of events comprising one or more target species detected by the processing electronics.

Example 49. The system of Example 48, wherein the processing electronics are configured to analyze the events log, and based on the analysis, to transmit a priority ranking of events to the external computing device.

Example 50. The system of any one of Examples 40 to 49, wherein the processing electronics are configured to compare the detected amount of the target species to a threshold amount and, based on that comparison, transmit the alarm notification to the external computing device over the communications network indicating that the target species has been detected at the one or more installations.

Example 51. The system of Example 50, wherein the threshold amount is in a range of 1 ppm-m to 1000 ppm-m of the target species.

Example 52. The system of Example 51, wherein the threshold amount is in a range of 25 ppm-m to 1000 ppm-m of the target species.

Example The system of Example 52, wherein the threshold amount is in a range of 25 ppm-m to 750 ppm-m of the target species.

Example 54. The system of any one of Examples 40 to 53, wherein the target species comprises methane.

Example 55. The system of any one of Examples 40 to 54, wherein the target species comprises hydrogen sulfide.

Example 56. The system of any one of Examples 40 to 55, wherein the target species comprises a gas.

Example 57. The system of any one of Examples 40 to 56, wherein the target species comprises a liquid.

Example 58. The system of any one of Examples 40 to 57, wherein the processing electronics are configured to detect an unauthorized intrusion of an animal (including a human) into the one or more petroleum installations and, based on the detection, to transmit a second alarm notification to the external computing device over the communications network indicating the unauthorized intrusion.

Example 59. The system of any one of Examples 40 to 58, wherein the communications network comprises a wireless communications network.

Example 60. The system of Example 59, wherein the wireless communications network comprises a cellular communications network.

Example 61. The system of Example 60, wherein the wireless communications network is configured to transmit processed image data to the external computing device at speeds in a range of 0.1 Mbps to 10 Mbps.

Example 62. The system of Example 61, wherein the wireless communications network is configured to transmit processed image data to the external computing device at speeds in a range of 0.5 Mbps to 2 Mbps.

Example 63. The system of any one of Examples 40 to 58, wherein the communications network comprises an Ethernet communications network Example 64. The system of any one of Examples 40 to 63, wherein the processing electronics are configured to transmit information about one or more events detected at the one or more installations to the external computing device, the external computing device configured to generate a user interface presentable to a user on a display device.

Example 65. The system of Example 64, wherein the user interface comprises a visible image window and an infrared image window.

Example 66. The system of any one of Examples 40 to 65, further comprising the one or more optical imaging systems.

Example 67. The system of any one of Examples 40 to 66, wherein the one or more optical imaging systems comprise an infrared (IR) detector array.

Example 68. The system of any one of Examples 40 to 67, wherein the one or more optical imaging systems comprise a visible light detector array.

Example 69. The system of any one of Examples 66 to 68, wherein the one or more optical imaging systems define a plurality of optical channels being spatially and spectrally different from one another, each of the plurality of optical channels positioned to transfer radiation incident on the optical imaging system towards an array of optical detectors.

Example 70. The system of Example 69, wherein the one or more optical imaging systems and the processing electronics are contained together in respective data acquisition and processing modules configured to be worn or carried by a person.

Example 71. The system of Example 69, wherein the one or more optical imaging systems and the processing electronics are configured to be mounted to respective support structures at the one or more petroleum installations.

Example 72. The system of any one of Examples 40 to 71, wherein the one or more optical imaging systems comprise a plurality of spectrally distinct infrared optical filters.

Example 73. The system of any one of Examples 40 to 72, wherein the processing electronics are configured to monitor a progression of a liquid leak over a period of time.

Example 74. The system of Example 73, wherein the processing electronics are configured to generate a color map of the progression of the liquid leak based on a length of residence time of the liquid leak at locations of the one or more installations.

Example 75. The system of any one of Examples 40 to 74, wherein at least a portion of the processing electronics are located remote from the one or more optical imaging systems.

Example 76. The system of any one of Examples 40 to 75, wherein the processing electronics are configured to generate a system overview image that illustrates locations of a plurality of optical imaging systems at the one or more installations, each optical imaging system of the plurality of optical imaging systems associated with an identifier.

Example 77. The system of any one of Examples 40 to 76, wherein the processing electronics are configured to generate a multi-view image that illustrates image data captured by multiple optical imaging systems at multiple sites of the one or a plurality of installations.

Example 78. The system of any one of Examples 40 to 77, wherein the processing electronics are configured to generate a mosaic image comprising a plurality of fields of view (FOVs) of an optical imaging system of the one or more optical imaging systems at the installation.

Example 79. A system for monitoring an installation, the system comprising:
  an optical imaging system comprising an array of optical detectors; and
  processing electronics configured to process image data detected by the optical imaging system, the processing electronics configured to:
  detect a target species based at least in part on the processed image data over multiple frames of the processed image data; and
  combine the multiple frames of processed image data into a summary alarm image that presents the detection of the target species over a period of time.

Example 80. The system of Example 79, wherein the summary alarm image comprises a single image.

Example 81. The system of any one of Examples 79 to 80, wherein the processing electronics are configured to create the summary alarm image by calculating an average concentration of the target species and/or an average of the image data representative of the concentration over the period of time.

Example 82. The system of any one of Examples 79 to 81, wherein the processing electronics are configured to generate a progressive mode to sequentially present summary alarm images for successive fields of view (FOVs) of the optical imaging system.

Example 83. The system of any one of Examples 79 to 82, wherein the processing electronics are configured to create an events log comprising a plurality of events comprising one or more target species detected by the processing electronics.

Example 84. The system of Example 83, wherein the processing electronics are configured to analyze the events log, and based on the analysis, to generate a priority ranking of events.

Example 85. The system of any one of Examples 79 to 84, wherein the processing electronics are configured to generate a mosaic image comprising a plurality of fields of view (FOVs) of the optical imaging system at the installation.

Example 86. The system of any one of Examples 79 to 85, wherein the processing electronics are configured to monitor a progression of a liquid leak over a period of time.

Example 87. The system of Example 86, wherein the processing electronics are configured to generate a color map of the progression of the liquid leak based on a length of residence time of the liquid leak at locations of the installation.

Example 88. The system of any one of Examples 79 to 87, wherein at least a portion of the processing electronics are located remote from the optical imaging system.

Example 89. The system of any one of Examples 79 to 88, wherein the processing electronics are configured to generate a system overview image that illustrates locations of a plurality of optical imaging systems at the installation, each optical imaging system of the plurality of optical imaging systems associated with an identifier.

Example 90. The system of any one of Examples 79 to 89, wherein the processing electronics are configured to generate a multi-view image that illustrates image data captured by multiple optical imaging systems at multiple sites of one or a plurality of installations.

Example 91. A system for monitoring an installation, the system comprising:
  an optical imaging system comprising an array of optical detectors; and
  processing electronics configured to process infrared image data detected by the optical imaging system, the processing electronics configured to:
  detect a target species based at least in part on the processed image data, the target species comprising a liquid leak at the installation; and
  monitor a progression of the liquid leak over a period of time.

Example 92. The system of Example 91, wherein the processing electronics are configured to generate a color map of the progression of the liquid leak based on a length of residence time of the liquid leak at locations of the one or more installations.

Example 93. A system for monitoring one or more installations, the system comprising:
  a plurality of optical imaging systems, each optical imaging system of the plurality of optical imaging systems comprising an array of optical detectors; and
  processing electronics configured to process image data detected by the plurality of optical imaging systems, the processing electronics configured to:
  detect one or more target species at the one or more installations based at least in part on the processed image data;
  generate a system overview image that illustrates locations of the plurality of optical imaging systems at the one or more installations, each optical imaging system of the plurality of optical imaging systems associated with an identifier; and
  associate the location of the optical imaging system at which the target species has been detected with the identifier.

Example 94. The system of Example 93, wherein, based on a detected amount of the one or more target species, the processing electronics are configured to transmit an alarm notification to an external computing device over a communications network indicating that the one or more target species has been detected at the one or more installations.

Example 95. The system of Example 94, wherein the processing electronics are configured to notify the external computing device of the location of the optical imaging system at which the one or more target species has been detected.

Example 96. A system for monitoring one or more installations, the system comprising:
  a plurality of optical imaging systems, each optical imaging system of the plurality of optical imaging systems comprising an array of optical detectors; and
  processing electronics configured to process image data detected by the plurality of optical imaging systems, the processing electronics configured to:
  detect one or more target species based at least in part on the processed image data;
  generate a multi-view image that illustrates image data captured by the plurality of optical imaging systems at a plurality of locations of the one or more installations; and
  associate the location of the optical imaging system at which the target species has been detected with an identifier.

Example 97. The system of Example 96, wherein, based on a detected amount of the one or more target species, the processing electronics are configured to transmit an alarm notification to an external computing device over a communications network indicating that the one or more target species has been detected at the one or more installations.

Example 98. The system of Example 97, wherein the processing electronics are configured to notify the external computing device of the location of the optical imaging system at which the one or more target species has been detected.

Example 99. A system for monitoring one or more installations, the system comprising:
  an optical imaging system comprising an array of optical detectors; and
  processing electronics configured to process image data detected by the optical imaging system, the processing electronics configured to:
  detect a target species based at least in part on the processed image data;
  generate a mosaic image comprising a plurality of fields of view (FOVs) of the optical imaging system at the petrochemical installation; and
  identify a field of view of the plurality of FOVs at which the target species has been detected.

Example 100. The system of Example 99, wherein, based on a detected amount of the target species, the processing electronics are configured to transmit an alarm notification to an external computing device over a communications network indicating that the target species has been detected at the one or more installations.

Example 101. The system of Example 100, wherein the processing electronics are configured to notify the external computing device of the field of view at which the one or more target species has been detected.

Example 102. A system for monitoring one or more installations, the system comprising:
  an optical imaging system comprising an array of optical detectors, the array of optical detectors comprising one or more visible image sensors and one or more infrared image sensors; and
  processing electronics configured to process image data detected by the optical imaging system, the processing electronics configured to:
  detect a target species based at least in part on the processed image data;
  generate a visible image and an infrared image from the processed image data, the detected target species rendered on at least one of the visible image and the infrared image; and
  generate a user interface that simultaneously illustrates the visible image and the infrared image.

Example 103. The system of Example 102, wherein the processing electronics are configured to transmit an alarm notification to an external computing device over a communications network indicating that the target species has been detected at the one or more installations.

Example 104. The system of Example 103, wherein the processing electronics are configured to transmit the user interface to the external computing device over the communications network, such that the external computing device can render the visible image and the infrared image on a display.

Example 105. A system for monitoring one or more installations, the system comprising:
  an optical imaging system comprising an array of optical detectors; and
  processing electronics configured to process image data detected by the optical imaging system, the processing electronics configured to:
  detect one or more target species based at least in part on the processed image data; and
  create an events log comprising a plurality of events, the plurality of events comprising one or more leaks associated with the one or more target species detected by the processing electronics.

Example 106. The system of Example 105, wherein the processing electronics are configured to analyze the events log, and based on the analysis, to create a priority ranking of the events.

Example 107. The system of any one of Examples 105 to 106, wherein the processing electronics are configured to transmit the event log to an external computing device over a communications network.

Example 108. The system of any one of Examples 105 to 107, wherein the processing electronics are configured to associate multiple events with one another and to form a group of the associated multiple events.

Example 109. The system of Example 108, wherein the processing electronics are configured to form the group of the associated multiple events based at least in part on at least one of event type, type of the detected one or more target species, event time, and a field of view (FOV) in which the one or more target species has been detected.

Example 110. A system for monitoring one or more installations, the system comprising:
  an optical imaging system comprising an array of optical detectors; and
  processing electronics configured to process image data detected by the optical imaging system, the processing electronics configured to:
  detect one or more target species based at least in part on the processed image data; and
  detect an unauthorized intrusion of an animal (including a human) into the one or more installations based at least in part on the processed image data.

Example 111. The system of Example 110, wherein, based on the detection of the one or more target species, the processing electronics are configured to transmit an alarm notification to an external computing device over a communications network.

Example 112. The system of any one of Examples 110 to 111, wherein, based on the detection of the unauthorized intrusion, the processing electronics are configured to transmit a second alarm notification to an external computing device over a communications network indicating the unauthorized intrusion.

Example 113. The system of any one of Examples 1 to 112, wherein the optical system comprises an infrared imaging system.

Example 114. The system of any one of Examples 1 to 113, wherein the optical imaging system defines a plurality of optical channels being spatially and spectrally different from one another, each of the plurality of optical channels positioned to transfer radiation incident on the optical imaging system towards the array of optical detectors.

Example 115. The system of Example 114, wherein the optical imaging system and the processing electronics are contained together in a data acquisition and processing module configured to be worn or carried by a person.

Example 116. The system of Example 114, wherein the optical imaging system and the processing electronics are configured to be mounted to a support structure at the petroleum installation.

Example 117. The system of any one of Examples 1 to 116, wherein the optical system comprises a plurality of spectrally distinct infrared optical filters.

Example 118. The system of any one of Examples 1 to 117, wherein the processing electronics are remote from the optical system.

Example 119. A non-transitory computer readable medium having instructions stored thereon that, when executed by processing electronics, based on a detected amount of a target species, transmits an alarm notification to an external computing device over a communications network indicating that the target species has been detected at a petrochemical installation.

Example 120. A non-transitory computer readable medium having instructions stored thereon that, when executed by processing electronics, receives data from one or more optical imaging systems at one or more installations, the one or more optical imaging systems configured to capture infrared image data at the one or more installations, and, based on a detected amount of the a target species, transmits an alarm notification to an external computing device over a communications network indicating that the target species has been detected at the one or more installations.

Example 121. A non-transitory computer readable medium having instructions stored thereon that, when executed by processing electronics, combines multiple frames of processed image data into a summary alarm image that presents a detection of a target species over a period of time.

Example 122. A non-transitory computer readable medium having instructions stored thereon that, when executed by processing electronics, monitors a progression of a liquid leak over a period of time.

Example 123. A non-transitory computer readable medium having instructions stored thereon that, when executed by processing electronics, generates a system overview image that illustrates locations of a plurality of optical imaging systems at one or more installations, each optical imaging system of the plurality of optical imaging systems associated with an identifier, and associates the location of the optical imaging system at which a target species has been detected with the identifier.

Example 124. A non-transitory computer readable medium having instructions stored thereon that, when executed by processing electronics, generates a multi-view image that illustrates image data captured by a plurality of optical imaging systems at a plurality of locations of one or more installations, and associates the location of the optical imaging system at which a target species has been detected with an identifier.

Example 125. A non-transitory computer readable medium having instructions stored thereon that, when executed by processing electronics, generates a mosaic image comprising a plurality of fields of view (FOVs) of an optical imaging system at a petrochemical installation, and identifies a field of view of the plurality of FOVs at which a target species has been detected.

Example 126. A non-transitory computer readable medium having instructions stored thereon that, when executed by processing electronics, generates a visible image and an infrared image from processed image data, wherein a detected target species is rendered on at least one of the visible image and the infrared image, and generates a user interface that simultaneously illustrates the visible image and the infrared image.

Example 127. A non-transitory computer readable medium having instructions stored thereon that, when executed by processing electronics, creates an events log comprising a plurality of events, the plurality of events comprising one or more leaks associated with one or more detected target species.

Example 128. A non-transitory computer readable medium having instructions stored thereon that, when executed by processing electronics, detects one or more target species based at least in part on processed image data, and detects an unauthorized intrusion of an animal (including a human) into one or more installations based at least in part on the processed image data.

Example 129. The non-transitory computer readable medium of any one of Examples 119 to 128, wherein the computer readable medium has instructions stored thereon that, when executed by processing electronics, detects the target species.

Example 130. The non-transitory computer readable medium of any one of Examples 119 to 129, further comprising the processing electronics of any of the preceding Examples.

Example 131. The non-transitory computer readable medium of any one of Examples 119 to 130, in combination with the system of any of the preceding Examples.

Example 132. A system comprising processing electronics configured to, based on a detected amount of a target species, transmit an alarm notification to an external computing device over a communications network indicating that the target species has been detected at a petrochemical installation.

Example 133. A system comprising processing electronics configured to combine multiple frames of processed image data into a summary alarm image that presents a detection of a target species over a period of time.

Example 134. A system comprising processing electronics configured to monitor a progression of a liquid leak over a period of time.

Example 135. A system comprising processing electronics configured to generate a system overview image that illustrates locations of a plurality of optical imaging systems at one or more installations, each optical imaging system of the plurality of optical imaging systems associated with an identifier, and to associate the location of the optical imaging system at which the target species has been detected with the identifier.

Example 136. A system comprising processing electronics configured to generate a multi-view image that illustrates image data captured by a plurality of optical imaging systems at a plurality of locations of one or more installations, and associate the location of the optical imaging system at which a target species has been detected with an identifier.

Example 137. A system comprising processing electronics configured to generate a mosaic image comprising a plurality of fields of view (FOVs) of an optical imaging system at a petrochemical installation, and to identify a field of view of the plurality of FOVs at which a target species has been detected.

Example 138. A system comprising processing electronics configured to generate a visible image and an infrared image from processed image data, wherein a detected target species is rendered on at least one of the visible image and the infrared image, and to generate a user interface that simultaneously illustrates the visible image and the infrared image.

Example 139. A system comprising processing electronics configured to create an events log comprising a plurality of events, the plurality of events comprising one or more leaks associated with one or more target species detected by the processing electronics.

Example 140. A system comprising processing electronics configured to detect one or more target species based at least in part on processed image data, and to detect an unauthorized intrusion of an animal (including a human) into one or more installations based at least in part on the processed image data.

Example 141. The system of any one of Examples 132 to 140, wherein the processing electronics are configured to detect the one or more target species.

Example 142. The system of any one of Examples 132 to 141, in combination with any of the preceding Examples.

Example 143. The system of any one of Examples 132 to 142, wherein the processing electronics are configured to receive image data based on images captured by at least one infrared optical imaging system, Example 144. A method for monitoring one or more installations, the method comprising:
  detecting a target species based at least in part on infrared image data captured by one or more optical imaging systems at the one or more installations; and
  based on a detected amount of the target species, transmitting an alarm notification to an external computing device over a communications network indicating that the target species has been detected at the one or more installations.

Example 145. The method of Example 144, further comprising capturing the infrared image data with the one or more optical imaging systems.

Example 146. The method of any one of Examples 144 to 145, further comprising detecting the target species over multiple frames of the infrared image data and combining the multiple frames of infrared image data into a summary alarm image that presents the detection of the target species over a period of time.

Example 147. The method of Example 146, further comprising creating the summary alarm image by calculating an average concentration of the target species and/or an average of the image data representative of the concentration over the period of time.

Example 148. The method of any one of Examples 146 to 147, further comprising generating a progressive mode to sequentially present summary alarm images for successive fields of view (FOVs) of an optical imaging system of the one or more optical imaging systems.

Example 149. The method of any one of Examples 144 to 148, further comprising creating an events log comprising a plurality of events comprising one or more fluid leaks.

Example 150. The method of Example 149, further comprising analyzing the events log, and based on the analysis, transmitting a priority ranking of events to the external computing device.

Example 151. The method of any one of Examples 144 to 150, further comprising comparing the detected amount of the target species to a threshold amount and, based on that comparison, transmit the alarm notification to the external computing device over the communications network indicating that the target species has been detected at the one or more installations.

Example 152. The method of Example 151, wherein the threshold amount is in a range of 1 ppm-m to 1000 ppm-m of the target species.

Example 153. The method of any one of Examples 144 to 152, further comprising detecting an unauthorized intrusion of an animal (including a human) into the one or more petroleum installations and, based on the detection, transmitting a second alarm notification to the external computing device over the communications network indicating the unauthorized intrusion.

Example 154. The method of any one of Examples 144 to 153, further comprising transmitting information about one or more events detected at the one or more installations to the external computing device, the external computing device configured to render a user interface presentable to a user on a display device.

Example 155. The method of Example 154, wherein the user interface comprises a visible image window and an infrared image window.

Example 156. The method of any one of Examples 144 to 155, further generating a system overview image that illustrates locations of a plurality of optical imaging systems at the one or more installations, each optical imaging system of the plurality of optical imaging systems associated with an identifier.

Example 157. The method of any one of Examples 144 to 156, further comprising generating a multi-view image that illustrates image data captured by multiple optical imaging systems at multiple sites of the one or a plurality of installations.

Any of Examples 1 to 157 can include any of the features described above (for example, any of the features in Examples 1 to 157), and do not necessarily need to include the optical imaging system and does not necessarily need to detect the target species.

Details of one or more implementations of the subject matter described in this disclosure are set forth in the accompanying drawings and the description below. Other features, aspects, and advantages will become apparent from the description, the drawings and the claims. Note that the relative dimensions of the following figures may not be drawn to scale.

BRIEF DESCRIPTION OF THE DRAWINGS

FIG. 5A is a diagram of a 4-by-3 pupil array comprising circular optical filters (and IR blocking material between the optical filters) used to spectrally divide an optical wavefront imaged with an embodiment of the system.

FIG. 5B is a diagram of a 4-by-3 pupil array comprising rectangular optical filters (and IR blocking material between the optical filters) used to spectrally divide an optical wavefront imaged with an embodiment of the system.

FIG. 11A is a schematic diagram illustrating a mobile infrared imaging system configured to be carried or worn by a human user.

FIG. 13A is a schematic system diagram of an optical system configured to be used in the mobile infrared imaging systems disclosed herein, according to various embodiments.

FIG. 13B is a schematic system diagram of an optical system configured to be used in the mobile infrared imaging systems disclosed herein, according to other embodiments.

FIG. 16B is a schematic diagram of a mosaic image window, according to various embodiments.

FIG. 16D illustrates a time lapsed leak progression image that shows the progression of a liquid leak over a time period, according to various embodiments.

FIG. 17B is a schematic diagram of an event guide, according to various embodiments.

Like reference numbers and designations in the various drawings indicate like elements.

DETAILED DESCRIPTION

I. Overview of Various Embodiments

Figure 1:
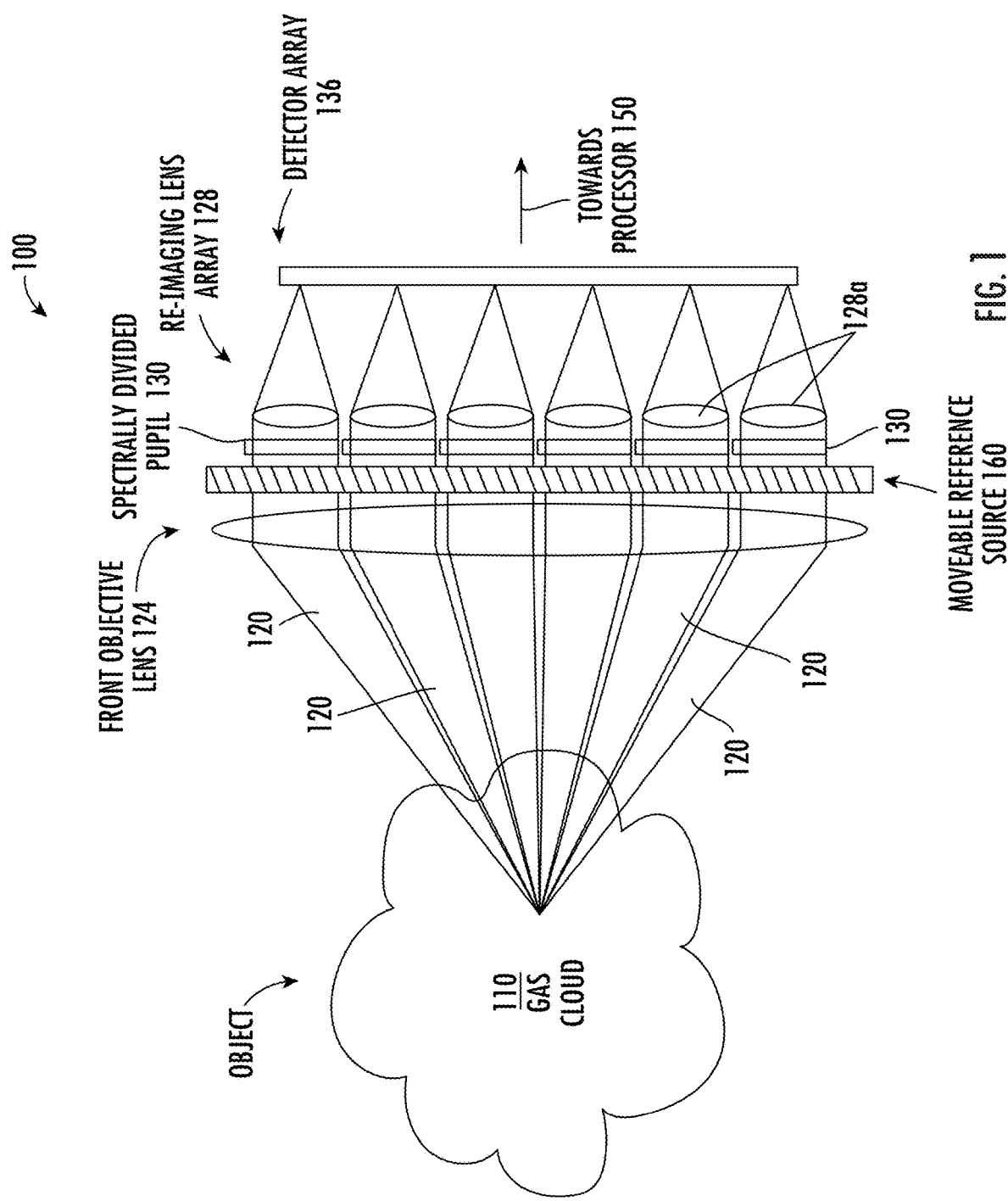
FIG. 1 shows an embodiment of an imaging system including a common front objective lens that has a pupil divided spectrally and re-imaged with a plurality of lenses onto an infrared FPA.

The following description is directed to certain implementations for the purposes of describing the innovative aspects of this disclosure. However, a person having ordinary skill in the art will readily recognize that the teachings herein can be applied in a multitude of different ways. The described implementations may be implemented in any device, apparatus, or system that can be configured to operate as an imaging system such as in an infra-red imaging system. The methods and systems described herein can be included in or associated with a variety of devices such as, but not limited to devices used for visible and infrared spectroscopy, multispectral and hyperspectral imaging devices used in oil and gas exploration, refining, and transportation, agriculture, remote sensing, defense and homeland security, surveillance, astronomy, environmental monitoring, etc. The methods and systems described herein have applications in a variety of fields including but not limited to agriculture, biology, physics, chemistry, defense and homeland security, environment, oil and gas industry, etc. The teachings are not intended to be limited to the implementations depicted solely in the Figures, but instead have wide applicability as will be readily apparent to one having ordinary skill in the art.

The spectral image of the scene can be represented as a three-dimensional data cube where two axes of the cube represent two spatial dimensions of the scene and a third axes of the data cube represents spectral information of the scene in different wavelength regions. The data cube can be processed using mathematical methods to obtain information about the scene. Some of the existing spectral imaging systems generate the data cube by scanning the scene in the spatial domain (e.g., by moving a slit across the horizontal and vertical dimensions of the scene) and/or spectral domain. Such scanning approaches acquire only a portion of the full data cube at a time. These portions of the full data cube are stored and then later processed to generate a full data cube.

Various embodiments disclosed herein describe a divided-aperture infrared spectral imaging (DAISI) system that is structured and adapted to provide identification of target chemical contents of the imaged scene. The system is based on spectrally-resolved imaging and can provide such identification with a single-shot (also referred to as a snapshot) comprising a plurality of images having different wavelength compositions that are obtained generally simultaneously. Without any loss of generality, snapshot refers to a system in which most of the data elements that are collected are continuously viewing the light emitted from the scene. In contrast in scanning systems, at any given time only a minority of data elements are continuously viewing a scene, followed by a different set of data elements, and so on, until the full dataset is collected. Relatively fast operation can be achieved in a snapshot system because it does not need to use spectral or spatial scanning for the acquisition of infrared (IR) spectral signatures of the target chemical contents. Instead, IR detectors (such as, for example, infrared focal plane arrays or FPAs) associated with a plurality of different optical channels having different wavelength profiles can be used to form a spectral cube of imaging data. Although spectral data can be obtained from a single snapshot comprising multiple simultaneously acquired images corresponding to different wavelength ranges, in various embodiments, multiple snap shots may be obtained. In various embodiments, these multiple snapshots can be averaged. Similarly, in certain embodiments multiple snap shots may be obtained and a portion of these can be selected and possibly averaged. Also, in contrast to commonly used IR spectral imaging systems, the DAISI system does not require cooling. Accordingly, it can advantageously use uncooled infrared detectors. For example, in various implementations, the imaging systems disclosed herein do not include detectors configured to be cooled to a temperature below 300 Kelvin. As another example, in various implementations, the imaging systems disclosed herein do not include detectors configured to be cooled to a temperature below 273 Kelvin. As yet another example, in various implementations, the imaging systems disclosed herein do not include detectors configured to be cooled to a temperature below 250 Kelvin. As another example, in various implementations, the imaging systems disclosed herein do not include detectors configured to be cooled to a temperature below 200 Kelvin.

Implementations disclosed herein provide several advantages over existing IR spectral imaging systems, most if not all of which may require FPAs that are highly sensitive and cooled in order to compensate, during the optical detection, for the reduction of the photon flux caused by spectrum-scanning operation. The highly sensitive and cooled FPA systems are expensive and require a great deal of maintenance. Since various embodiments disclosed herein are configured to operate in single-shot acquisition mode without spatial and/or spectral scanning, the instrument can receive photons from a plurality of points (e.g., every point) of the object substantially simultaneously, during the single reading. Accordingly, the embodiments of imaging system described herein can collect a substantially greater amount of optical power from the imaged scene (for example, an order of magnitude more photons) at any given moment in time especially in comparison with spatial and/or spectral scanning systems. Consequently, various embodiments of the imaging systems disclosed herein can be operated using uncooled detectors (for example, FPA unit including an array of microbolometers) that are less sensitive to photons in the IR but are well fit for continuous monitoring applications. For example, in various implementations, the imaging systems disclosed herein do not include detectors configured to be cooled to a temperature below 300 Kelvin. As another example, in various implementations, the imaging systems disclosed herein do not include detectors configured to be cooled to a temperature below 273 Kelvin. As yet another example, in various implementations, the imaging systems disclosed herein do not include detectors configured to be cooled to a temperature below 250 Kelvin. As another example, in various implementations, the imaging systems disclosed herein do not include detectors configured to be cooled to a temperature below 200 Kelvin. Imaging systems including uncooled detectors can be capable of operating in extreme weather conditions, require less power, are capable of operation during day and night, and are less expensive. Some embodiments described herein can also be less susceptible to motion artifacts in comparison with spatially and/or spectrally scanning systems which can cause errors in either the spectral data, spatial data, or both.

In various embodiments disclosed herein, the DAISI system can be mobile. For example, the DAISI system can be configured to be worn or carried by a person, e.g., the DAISI system can be miniaturized to fit in a relatively small housing or compartment. For example, the components of the DAISI system can be sized and shaped to fit within small dimensions and can have a mass sufficiently small to enable the human user to carry or wear the system without undue exertion. As explained herein, in some embodiments, the DAISI system can be sized and shaped to fit within a volume of less than about 300 cubic inches, or in some embodiments, less than about 200 cubic inches. In still other embodiments, the DAISI system can be sized and shaped to fit within a volume less than about 100 cubic inches. For example, in some arrangements, the DAISI system can be sized and shaped to fit within a volume in a range of about 50 cubic inches to about 300 cubic inches. In other arrangements, the DAISI system can be sized and shaped to fit within a volume in a range of about 80 cubic inches to about 200 cubic inches.

Advantageously, such a portable and/or wearable DAISI system can enable the user to monitor installations in remote locations and to detect the presence of various gases (e.g., poisonous gases) in real-time. Further, the portable DAISI system can enable the user to travel to different installations to monitor the presence of gases or chemicals in multiple locations. For example, the user may travel to an oil drilling installation in which oil is pumped from the ground. The user can carry or attach the portable DAISI system to his or her clothing or body (e.g., by way of a clip, hat, etc.) and can activate the system while he or she is on-site. Optical components on board the portable DAISI system can capture one or more snapshot multispectral images of portions of the installation susceptible to gas or chemical leaks. Computing units on board the portable DAISI system can process the captured multispectral image data to detect and/or classify gases or chemicals present at the site. A communications module can notify the user of the detected gases. For example, in various embodiments, the communications module can send a notification to a user interface (such as a set of computing eyeglasses, a mobile computing device such as a mobile smartphone, a tablet computing device, a laptop computing device, or any other suitable interface), and the user interface can display information about the detected gases to the user in real-time, e.g., at the oil drilling installation.

In various embodiments, DAISI systems can be provided at multiple locations, for example, to monitor different installations or facilities. For example, in various arrangements, multiple DAISI systems (which may be portable in some embodiments) can be deployed at different petrochemical installations, e.g., at oil and/or gas well(s), along pipeline(s), at petrochemical processing plants, or at any other facility where it may be important to detect leaked fluids (e.g., gas leaks, liquid oil spills, etc.). Various embodiments disclosed herein enable the monitoring of one or multiple remote facilities so that the user or operator of the DAISI systems can determine the location, type, timing, and/or concentration of a fluid leak (e.g. a gas or liquid leak) at any installation being monitored.

II. Examples of Divided Aperture Intrared Spectral Imager Systems

FIG. 1 provides a diagram schematically illustrating spatial and spectral division of incoming light by an embodiment 100 of a divided aperture infrared spectral imager (DAISI) system that can image an object 110 possessing IR spectral signature(s). The system 100 includes a front objective lens 124, an array of optical filters 130, an array of reimaging lenses 128 and a detector array 136. In various embodiments, the detector array 136 can include a single FPA or an array of FPAs. Each detector in the detector array 136 can be disposed at the focus of each of the lenses in the array of reimaging lenses 128. In various embodiments, the detector array 136 can include a plurality of photo-sensitive devices. In some embodiments, the plurality of photo-sensitive devices may comprise a two-dimensional imaging sensor array that is sensitive to radiation having wavelengths between 1 μm and 20 μm (for example, in near infra-red wavelength range, mid infra-red wavelength range, or long infra-red wavelength range). In various embodiments, the plurality of photo-sensitive devices can include CCD or CMOS sensors, bolometers, microbolometers or other detectors that are sensitive to infra-red radiation.

An aperture of the system 100 associated with the front objective lens system 124 is spatially and spectrally divided by the combination of the array of optical filters 130 and the array of reimaging lenses 128. In various embodiments, the combination of the array of optical filters 130 and the array of reimaging lenses 128 can be considered to form a spectrally divided pupil that is disposed forward of the optical detector array 136. The spatial and spectral division of the aperture into distinct aperture portions forms a plurality of optical channels 120 along which light propagates. In various embodiments, the array 128 of re-imaging lenses 128a and the array of spectral filters 130 which respectively correspond to the distinct optical channels 120. The plurality of optical channels 120 can be spatially and/or spectrally distinct. The plurality of optical channels 120 can be formed in the object space and/or image space. In one implementation, the distinct channels 120 may include optical channels that are separated angularly in space. The array of spectral filters 130 may additionally include a filter-holding aperture mask (comprising, for example, IR light-blocking materials such as ceramic, metal, or plastic). Light from the object 110 (for example a cloud of gas), the optical properties of which in the IR are described by a unique absorption, reflection and/or emission spectrum, is received by the aperture of the system 100. This light propagates through each of the plurality of optical channels 120 and is further imaged onto the optical detector array 136. In various implementations, the detector array 136 can include at least one FPA. In various embodiments, each of the re-imaging lenses 128a can be spatially aligned with a respectively-corresponding spectral region. In the illustrated implementation, each filter element from the array of spectral filters 130 corresponds to a different spectral region. Each re-imaging lens 128a and the corresponding filter element of the array of spectral filter 130 can coincide with (or form) a portion of the divided aperture and therefore with respectively-corresponding spatial channel 120. Accordingly, in various embodiment an imaging lens 128a and a corresponding spectral filter can be disposed in the optical path of one of the plurality of optical channels 120. Radiation from the object 110 propagating through each of the plurality of optical channels 120 travels along the optical path of each re-imaging lens 128a and the corresponding filter element of the array of spectral filter 130 and is incident on the detector array (e.g., FPA component) 136 to form a single image (e.g., sub-image) of the object 110. The image formed by the detector array 136 generally includes a plurality of sub-images formed by each of the optical channels 120. Each of the plurality of sub-images can provide different spatial and spectral information of the object 110. The different spatial information results from some parallax because of the different spatial locations of the smaller apertures of the divided aperture. In various embodiments, adjacent sub-images can be characterized by close or substantially equal spectral signatures. The detector array (e.g., FPA component) 136 is further operably connected with a processor 150 (not shown). The processor 150 can be programmed to aggregate the data acquired with the system 100 into a spectral data cube. The data cube represents, in spatial (x, y) and spectral (λ) coordinates, an overall spectral image of the object 110 within the spectral region defined by the combination of the filter elements in the array of spectral filters 130. Additionally, in various embodiments, the processor or processing electronics 150 may be programmed to determine the unique absorption characteristic of the object 110. Also, the processor/processing electronics 150 can, alternatively or in addition, map the overall image data cube into a cube of data representing, for example, spatial distribution of concentrations, c, of targeted chemical components within the field of view associated with the object 110.

Various implementations of the embodiment 100 can include an optional moveable temperature-controlled reference source 160 including, for example, a shutter system comprising one or more reference shutters maintained at different temperatures. The reference source 160 can include a heater, a cooler or a temperature-controlled element configured to maintain the reference source 160 at a desired temperature. For example, in various implementations, the embodiment 100 can include two reference shutters maintained at different temperatures. The reference source 160 is removably and, in one implementation, periodically inserted into an optical path of light traversing the system 100 from the object 110 to the detector array (e.g., FPA component) 136 along at least one of the channels 120. The removable reference source 160 thus can block such optical path. Moreover, this reference source 160 can provide a reference IR spectrum to recalibrate various components including the detector array 136 of the system 100 in real time. The configuration of the moveable reference source 160 is further discussed below.

In the embodiment 100, the front objective lens system 124 is shown to include a single front objective lens positioned to establish a common field-of-view (FOV) for the reimaging lenses 128a and to define an aperture stop for the whole system. In this specific case, the aperture stop substantially spatially coincides with and/or is about the same size as or slightly larger than the plurality of smaller limiting apertures corresponding to different optical channels 120. As a result, the positions for spectral filters of the different optical channels 120 coincide with the position of the aperture stop of the whole system, which in this example is shown as a surface between the lens system 124 and the array 128 of the reimaging lenses 128a. In various implementations, the lens system 124 can be an objective lens 124. However, the objective lens 124 is optional and various embodiments of the system 100 need not include the objective lens 124. In various embodiments, the objective lens 124 can slightly shift the images obtained by the different detectors in the array 136 spatially along a direction perpendicular to optical axis of the lens 124, thus the functionality of the system 100 is not necessarily compromised when the objective lens 124 is not included. Generally, however, the field apertures corresponding to different optical channels may be located in the same or different planes. These field apertures may be defined by the aperture of the reimaging lens 128a and/or filters in the divided aperture 130 in certain implementations. In one implementation, the field apertures corresponding to different optical channels can be located in different planes and the different planes can be optical conjugates of one another. Similarly, while all of the filter elements in the array of spectral filters 130 of the embodiment 100 are shown to lie in one plane, generally different filter elements of the array of spectral filter 130 can be disposed in different planes. For example, different filter elements of the array of spectral filters 130 can be disposed in different planes that are optically conjugate to one another. However, in other embodiments, the different filter elements can be disposed in non-conjugate planes.

Figure 2:
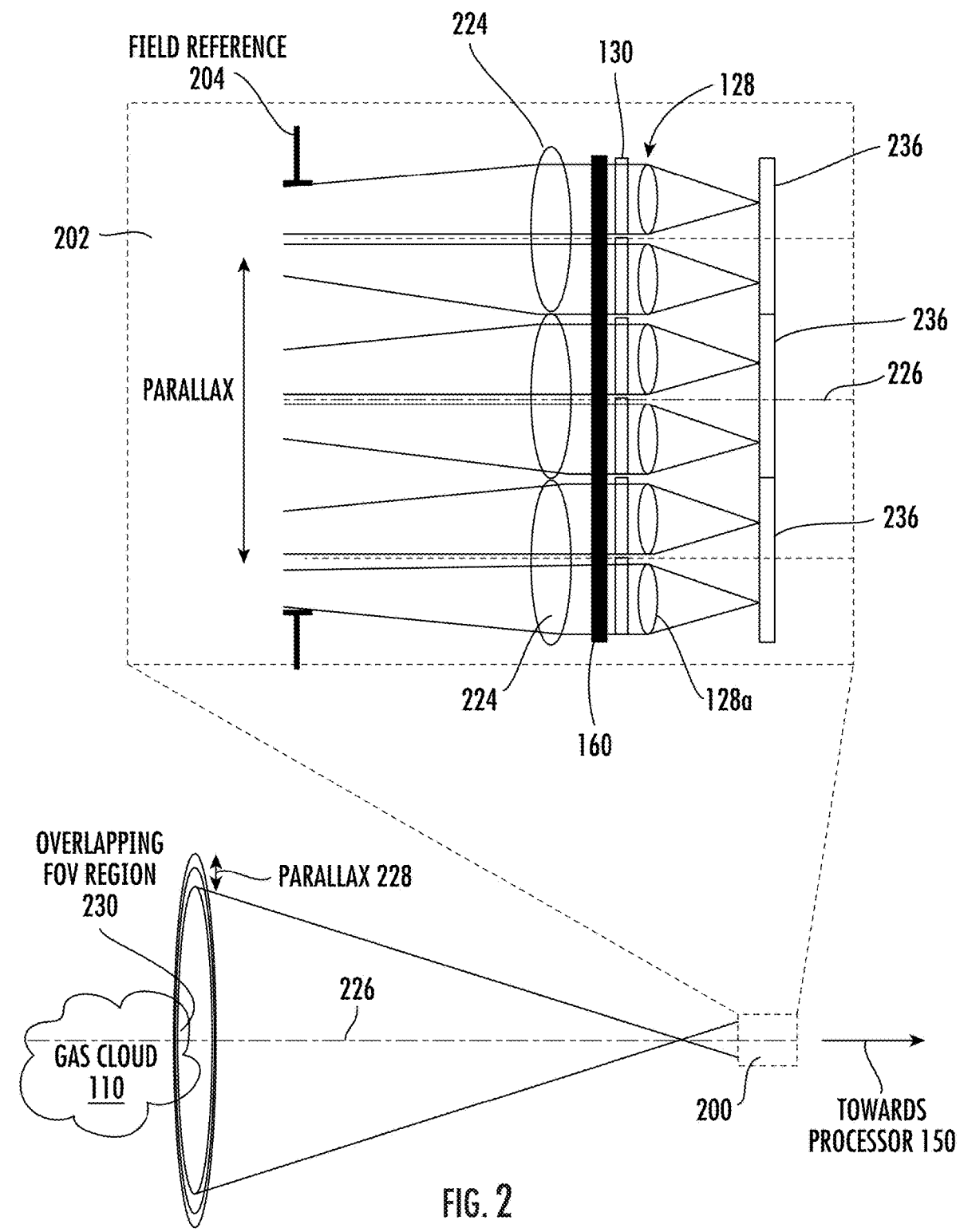
FIG. 2 shows an embodiment with a divided front objective lens and an array of infrared sensing FPAs.

In contrast to the embodiment 100, the front objective lens 124 need not be a single optical element, but instead can include a plurality of lenses 224 as shown in an embodiment 200 of the DAISI imaging system in FIG. 2. These lenses 224 are configured to divide an incoming optical wavefront from the object 110. For example, the array of front objective lenses 224 can be disposed so as to receive an IR wavefront emitted by the object that is directed toward the DAISI system. The plurality of front objective lenses 224 divide the wavefront spatially into non-overlapping sections. FIG. 2 shows three objective lenses 224 in a front optical portion of the optical system contributing to the spatial division of the aperture of the system in this example. The plurality of objective lenses 224, however, can be configured as a two-dimensional (2D) array of lenses. FIG. 2 presents a general view of the imaging system 200 and the resultant field of view of the imaging system 200. An exploded view 202 of the imaging system 200 is also depicted in greater detail in a figure inset of FIG. 2. As illustrated in the detailed view 202, the embodiment of the imaging system 200 includes a field reference 204 at the front end of the system. The field reference 204 can be used to truncate the field of view. The configuration illustrated in FIG. 2 has an operational advantage over embodiment 100 of FIG. 1 in that the overall size and/or weight and/or cost of manufacture of the embodiment 200 can be greatly reduced because the objective lens is smaller. Each pair of the lenses in the array 224 and the array 128 is associated with a field of view (FOV). Each pair of lenses in the array 224 and the array 128 receives light from the object from a different angle. Accordingly, the FOV of the different pairs of lenses in the array 224 and the array 128 do not completely overlap as a result of parallax. As the distance between the imaging system 200 (portion 202) and the object 110 increases, the overlapping region 230 between the FOVs of the individual lenses 224 increases while the amount of parallax 228 remains approximately the same, thereby reducing its effect on the system 200. When the ratio of the parallax-to-object-distance is substantially equal to the pixel-size-to-system-focal-length ratio then the parallax effect may be considered to be negligible and, for practical purposes, no longer distinguishable. While the lenses 224 are shown to be disposed substantially in the same plane, optionally different objective lenses in the array of front objective lenses 224 can be disposed in more than one plane. For example, some of the individual lenses 224 can be displaced with respect to some other individual lenses 224 along the axis 226 (not shown) and/or have different focal lengths as compared to some other lenses 224. As discussed below, the field reference 204 can be useful in calibrating the multiple detectors 236.

In one implementation, the front objective lens system such as the array of lenses 224 is configured as an array of lenses integrated or molded in association with a monolithic substrate. Such an arrangement can reduce the costs and complexity otherwise accompanying the optical adjustment of individual lenses within the system. An individual lens 224 can optionally include a lens with varying magnification. As one example, a pair of thin and large diameter Alvarez plates can be used in at least a portion of the front objective lens system. Without any loss of generality, the Alvarez plates can produce a change in focal length when translated orthogonally with respect to the optical beam.

In further reference to FIG. 1, the detector array 136 (e.g., FPA component) configured to receive the optical data representing spectral signature(s) of the imaged object 110 can be configured as a single imaging array (e.g., FPA) 136. This single array may be adapted to acquire more than one image (formed by more than one optical channel 120) simultaneously. Alternatively, the detector array 136 may include a FPA unit. In various implementations, the FPA unit can include a plurality of optical FPAs. At least one of these plurality of FPAs can be configured to acquire more than one spectrally distinct image of the imaged object. For example, as shown in the embodiment 200 of FIG. 2, in various embodiments, the number of FPAs included in the FPA unit may correspond to the number of the front objective lenses 224. In the embodiment 200 of FIG. 2, for example, three FPAs 236 are provided corresponding to the three objective lenses 224. In one implementation of the system, the FPA unit can include an array of microbolometers. The use of multiple microbolometers advantageously allows for an inexpensive way to increase the total number of detection elements (i.e. pixels) for recording the three-dimensional data cube in a single acquisition event (i.e. one snapshot). In various embodiments, an array of microbolometers more efficiently utilizes the detector pixels of the array of FPAs (e.g., each FPA) as the number of unused pixels is reduced, minimized and/or eliminated between the images that may exist when using a single microbolometer.

Figure 3A:
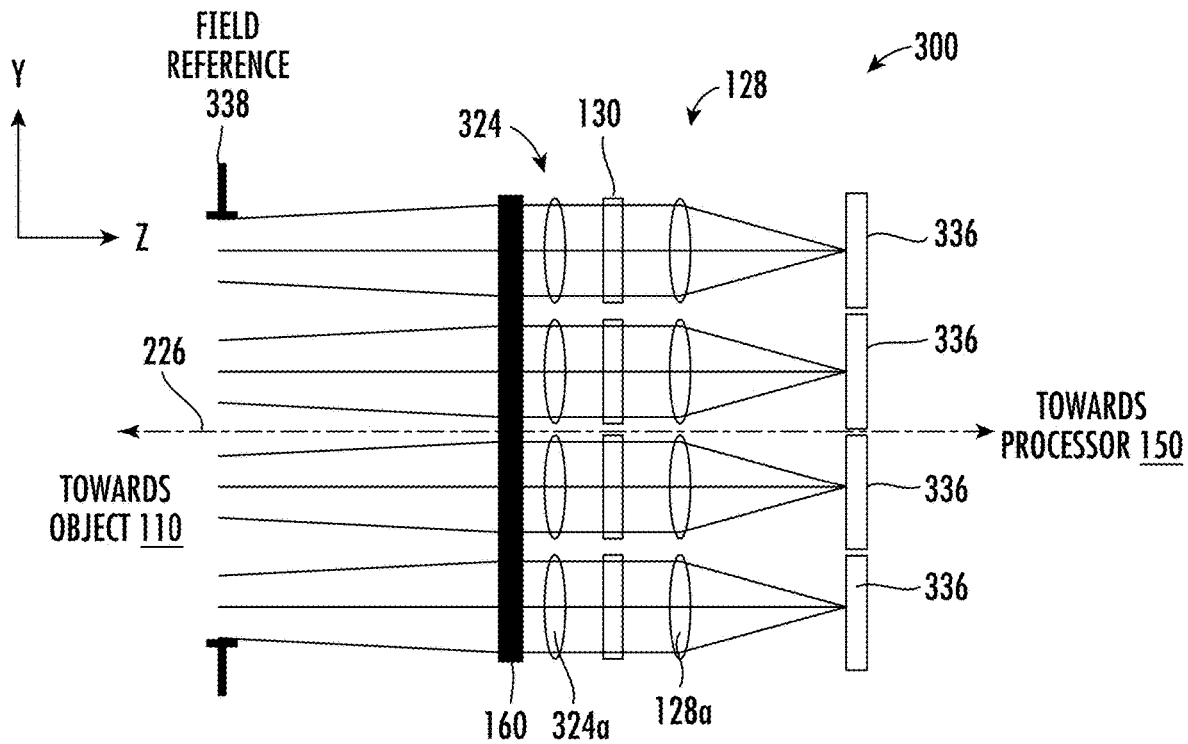
FIG. 3A represents an embodiment employing an array of front objective lenses operably matched with the re-imaging lens array.

FIG. 3A illustrates schematically an embodiment 300 of the imaging system in which the number of the front objective lenses 324a in the lens array 324, the number of re-imaging lenses 128a in the lens array 128, and the number of FPAs 336 are the same. So configured, each combination of respectively corresponding front objective lens 324, re-imaging lens 128a, and FPAs 336 constitutes an individual imaging channel. Such a channel is associated with acquisition of the IR light transmitted from the object 110 through an individual filter element of the array of optical filters 130. A field reference 338 of the system 300 is configured to have a uniform temperature across its surface and be characterized by a predetermined spectral curve of radiation emanating therefrom. In various implementations, the field reference 338 can be used as a calibration target to assist in calibrating or maintaining calibration of the FPA. Accordingly, in various implementations, the field reference 338 is used for dynamically adjusting the data output from each FPA 336 after acquisition of light from the object 110. This dynamic calibration process helps provide that output of the different (e.g., most, or each of the) FPA 336 represents correct acquired data, with respect to the other FPAs 336 for analysis, as discussed below in more detail.

Figure 3B:
FIG. 3B illustrates a two-dimensional array of optical components corresponding to the embodiment of FIG. 3A.

FIG. 3B illustrates the plan view perpendicular to the axis 226 of an embodiment 300 of the imaging system illustrated in FIG. 3A. For the embodiment shown in FIG. 3B, the optical components (e.g., objective lenses 324a, filter elements of the array of spectral filters 130, re-imaging lenses 128a and FPA units 336) are arranged as a 4×3 array. In one implementation, the 4×3 array 340 of optical components (lenses 324a, 128a; detector elements 336) is used behind the temperature controlled reference target 160. The field reference aperture 338 can be adapted to obscure and/or block a peripheral portion of the bundle of light propagating from the object 110 towards the FPA units 336. As a result, the field reference 338 obscures and/or blocks the border or peripheral portion(s) of the images of the object 110 formed on the FPA elements located along the perimeter 346 of the detector system. Generally, two elements of the FPA unit will produce substantially equal values of digital counts when they are used to observe the same portion of the scene in the same spectral region using the same optical train. If any of these input parameters (for example, scene to be observed, spectral content of light from the scene, or optical elements delivering light from the scene to the two detector elements) differ, the counts associated with the elements of the FPA unit will differ as well. Accordingly, and as an example, in a case when the two FPAs of the FPA unit 336 (such as those denoted as #6 and #7 in FIG. 3B) remain substantially un-obscured by the field reference 338, the outputs from these FPAs can be dynamically adjusted to the output from one of the FPAs located along perimeter 346 (such as, for example, the FPA element #2 or FPA element #11) that processes light having similar spectral characteristics.

Figure 4:
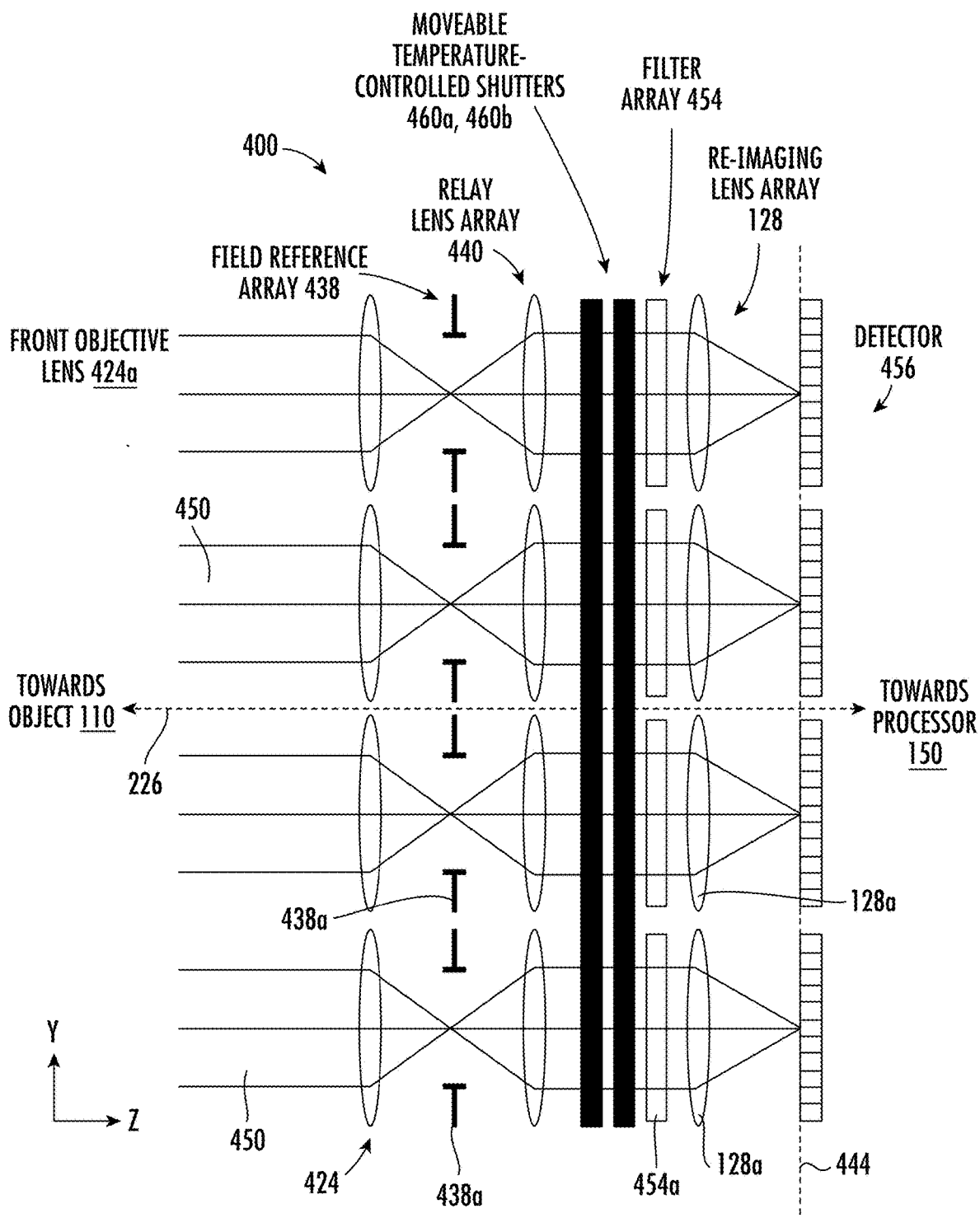
FIG. 4 is a diagram of the embodiment employing an array of field references (e.g., field stops that can be used as references for calibration) and an array of respectively corresponding relay lenses.

FIG. 4 illustrates schematically a portion of another embodiment of an imaging system 400 that contains an array 424 of front objective lenses 424a. The array 424 of lenses 424a adapted to receive light from the object 110 and relay the received light to the array 128 of re-imaging lenses 128a through an array 438 of field references (or field stops) 438a, and through an array 440 of the relay lenses. The spectral characteristics of the field references/field stops 438a can be known. The field references 438a are disposed at corresponding intermediate image planes defined, with respect to the object 110, by respectively corresponding front objective lenses 424a. When refractive characteristics of all of the front objective lenses 424a are substantially the same, all of the field references 438a are disposed in the same plane. A field reference 438a of the array 438 obscures (or casts a shadow on) a peripheral region of a corresponding image (e.g., sub-image) formed at the detector plane 444 through a respectively corresponding spatial imaging channel 450 of the system 400 prior to such image being spectrally processed by the processor 150. The array 440 of relay lenses then transmits light along each of the imaging channels 450 through different spectral filters 454a of the filter array 454, past the calibration apparatus that includes two temperature controlled shutters 460a, 460b, and then onto the detector module 456. In various embodiments, the detector module 456 can include a microbolometer array or some other IR FPA.

The embodiment 400 has several operational advantages. It is configured to provide a spectrally known object within every image (e.g., sub-image) and for every snapshot acquisition which can be calibrated against. Such spectral certainty can be advantageous when using an array of IR FPAs like microbolometers, the detection characteristics of which can change from one imaging frame to the next due to, in part, changes in the scene being imaged as well as the thermal effects caused by neighboring FPAs. In various embodiments, the field reference array 438 of the embodiment 400—can be disposed within the Rayleigh range (approximately corresponding to the depth of focus) associated with the front objective lenses 424, thereby removing unusable blurred pixels due to having the field reference outside of this range. Additionally, the embodiment 400 of FIG. 4 can be more compact than, for example, the configuration 300 of FIG. 3A. In the system shown in FIG. 3A, for example, the field reference 338 may be separated from the lens array 324 by a distance greater than several (for example, five) focal lengths to minimize/reduce blur contributed by the field reference to an image formed at a detector plane.

In various embodiments, the multi-optical FPA unit of the IR imaging system can additionally include an FPA configured to operate in a visible portion of the spectrum. In reference to FIG. 1, for example, an image of the scene of interest formed by such visible-light FPA may be used as a background to form a composite image by overlapping an IR image with the visible-light image. The IR image may be overlapped virtually, with the use of a processor and specifically-designed computer program product enabling such data processing, or actually, by a viewer. The IR image may be created based on the image data acquired by the individual FPAs 136. The so-formed composite image facilitates the identification of the precise spatial location of the target species, the spectral signatures of which the system is able to detect/recognize.

Optical Filters.

The optical filters, used with an embodiment of the system, that define spectrally-distinct IR image (e.g., sub-image) of the object can employ absorption filters, interference filters, and Fabry-Perot etalon based filters, to name just a few. When interference filters are used, the image acquisition through an individual imaging channel defined by an individual re-imaging lens (such as a lens 128a of FIGS. 1, 2, 3, and 4) may be carried out in a single spectral bandwidth or multiple spectral bandwidths. Referring again to the embodiments 100, 200, 300, 400 of FIGS. 1 through 4, and in further reference to FIG. 3B, examples of a 4-by-3 array of spectral filters 130 is shown in FIGS. 5A and 5B. Individual filters 1 through 12 are juxtaposed with a supporting opto-mechanical element (not shown) to define a filter-array plane that is oriented, in operation, substantially perpendicularly to the general optical axis 226 of the imaging system. In various implementations, the individual filters 1 through 12 need not be discrete optical components. Instead, the individual filters 1 through 12 can comprise one or more coatings that are applied to one or more surfaces of the reimaging lenses (such as a lens 128a of FIGS. 1, 2, 3, and 4) or the surfaces of one or more detectors.

Figure 6A:
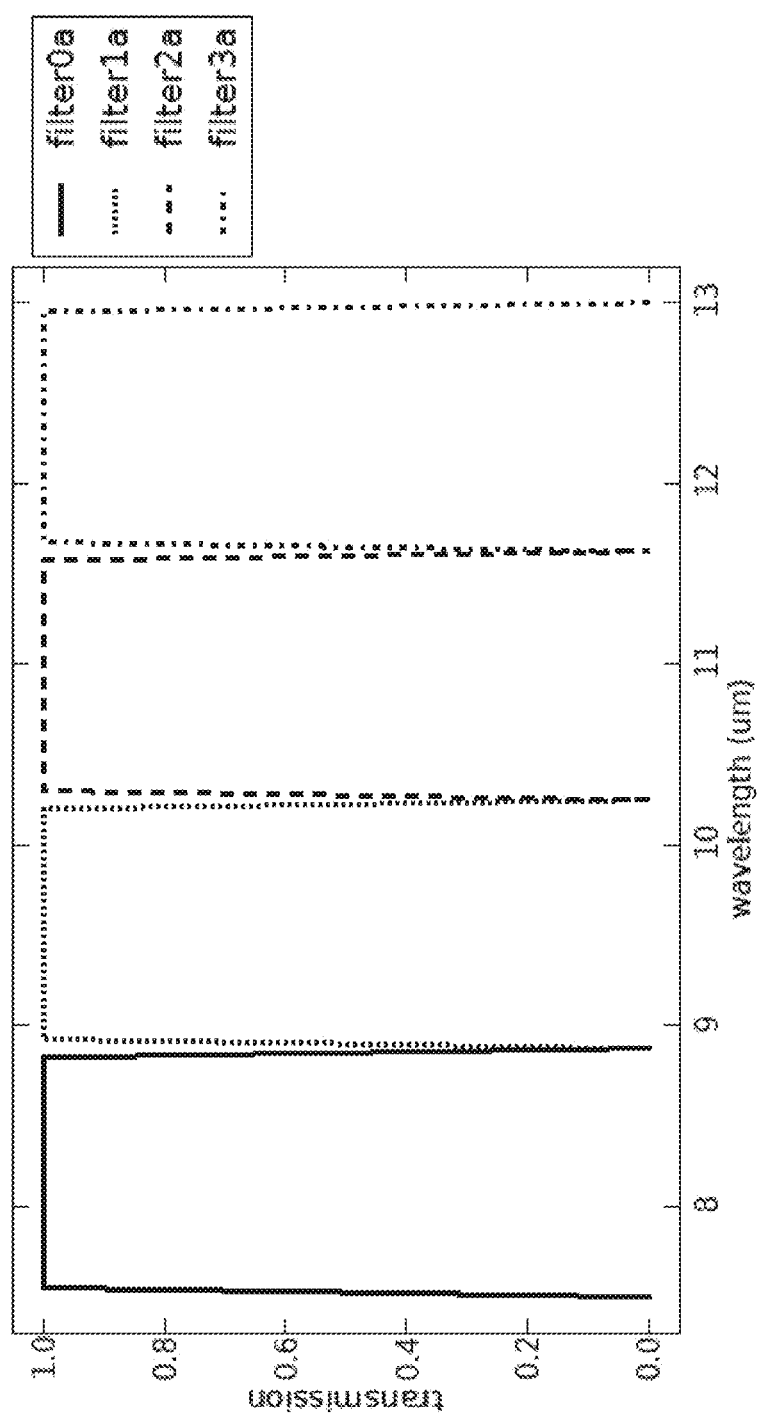
FIG. 6A depicts theoretical plots of transmission characteristics of a combination of band-pass filters used with an embodiment of the system.
Figure 6B:
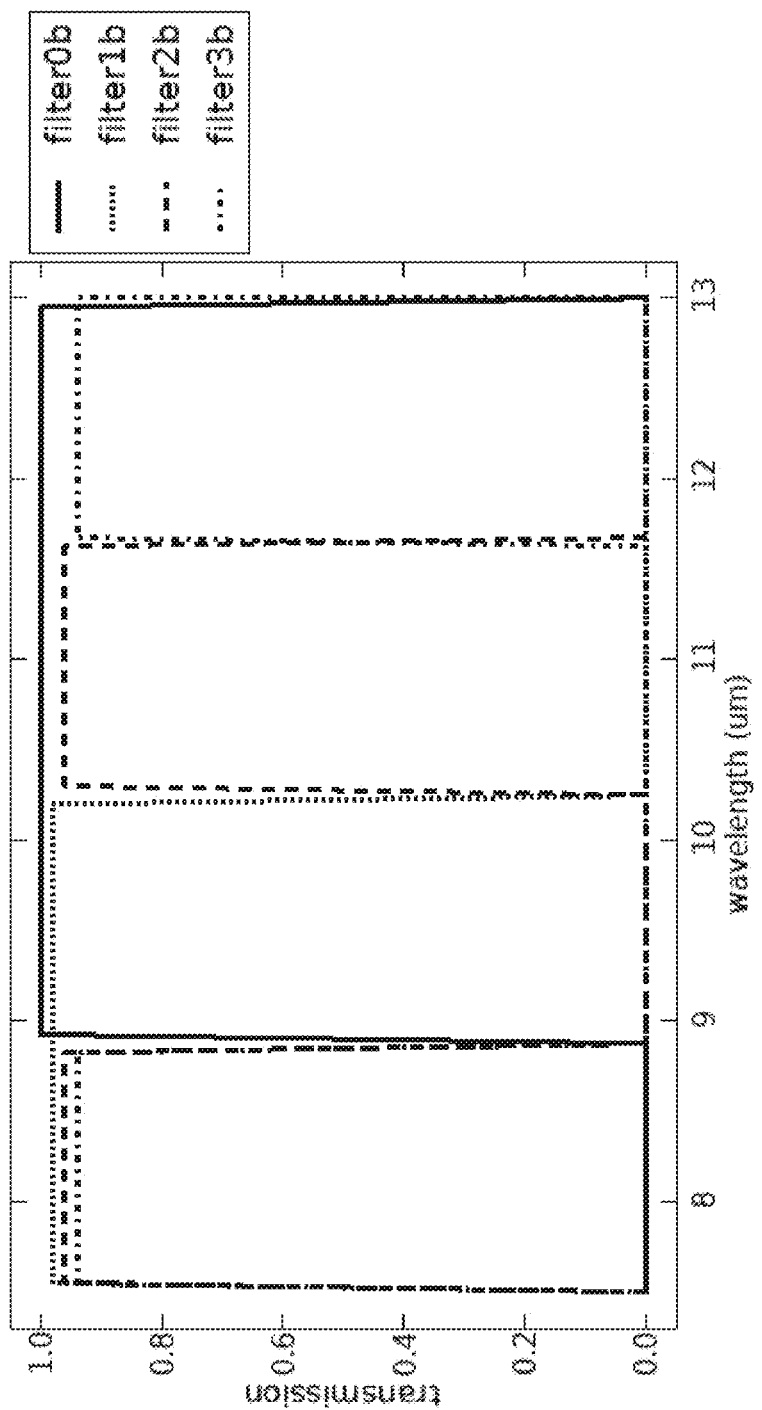
FIG. 6B depicts theoretical plots of transmission characteristics of a spectrally multiplexed notch-pass filter combination used in an embodiment of the system.

The optical filtering configuration of various embodiments disclosed herein may advantageously use a bandpass filter defining a specified spectral band. Any of the filters 0a through 3a, the transmission curves of which are shown in FIG. 6A may, for example, be used. The filters may be placed in front of the optical FPA (or generally, between the optical FPA and the object). In particular, and in further reference to FIGS. 1, 2 3, and 4, when optical detector arrays 136, 236, 336, 456 include microbolometers, the predominant contribution to noise associated with image acquisition is due to detector noise. To compensate and/or reduce the noise, various embodiments disclosed herein utilize spectrally-multiplexed filters. In various implementations, the spectrall-multiplexed filters can comprise a plurality of long pass filters, a plurality long pass filters, a plurality of band pass filters and any combinations thereof. An example of the spectral transmission characteristics of spectrally-multiplexed filters 0b through 3d for use with various embodiments of imaging systems disclosed herein is depicted in FIG. 6B. Filters of FIG. 6C can be referred to as long-wavelength pass, LP filters. An LP filter generally attenuates shorter wavelengths and transmits (passes) longer wavelengths (e.g., over the active range of the target IR portion of the spectrum). In various embodiments, short-wavelength-pass filters, SP, may also be used. An SP filter generally attenuates longer wavelengths and transmits (passes) shorter wavelengths (e.g., over the active range of the target IR portion of the spectrum). At least in part due to the snap-shot/non-scanning mode of operation, embodiments of the imaging system described herein can use less sensitive microbolometers without compromising the SNR. The use of microbolometers, as detector-noise-limited devices, in turn not only benefits from the use of spectrally multiplexed filters, but also does not require cooling of the imaging system during normal operation.

Referring again to FIGS. 6A, 6B, 6C, and 6D, each of the filters (0b . . . 3d) transmits light in a substantially wider region of the electromagnetic spectrum as compared to those of the filters (0a . . . 3a). Accordingly, when the spectrally-multiplexed set of filters (0b . . . 0d) is used with an embodiment of the imaging system, the overall amount of light received by the FPAs (for example, 236, 336) is larger than would be received when using the bandpass filters (0a . . . 4a). This "added" transmission of light defined by the use of the spectrally-multiplexed LP (or SP) filters facilitates an increase of the signal on the FPAs above the level of the detector noise. Additionally, by using, in an embodiment of the imaging system, filters having spectral bandwidths greater than those of band-pass filters, the uncooled FPAs of the embodiment of the imaging system experience less heating from radiation incident thereon from the imaged scene and from radiation emanating from the FPA in question itself. This reduced heating is due to a reduction in the back-reflected thermal emission(s) coming from the FPA and reflecting off of the filter from the non-band-pass regions. As the transmission region of the multiplexed LP (or SP) filters is wider, such parasitic effects are reduced thereby improving the overall performance of the FPA unit.

In one implementation, the LP and SP filters can be combined, in a spectrally-multiplexed fashion, in order to increase or maximize the spectral extent of the transmission region of the filter system of the embodiment.

The advantage of using spectrally multiplexed filters is appreciated based on the following derivation, in which a system of M filters is examined (although it is understood that in practice an embodiment of the invention can employ any number of filters). As an illustrative example, the case of M=7 is considered. Analysis presented below relates to one spatial location in each of the images (e.g., sub-images) formed by the differing imaging channels (e.g., different optical channels 120) in the system. A similar analysis can be performed for each point at an image (e.g., sub-image), and thus the analysis can be appropriately extended as required.

The unknown amount of light within each of the M spectral channels (corresponding to these M filters) is denoted with $f_1$, $f_2$, $f_3$, $f_3$ . . . $f_M$, and readings from corresponding detector elements receiving light transmitted by each filter is denoted as $g_1$, $g_2$, $g_3$ . . . $g_M$, while measurement errors are represented by $n_1$, $n_2$, $n_3$, . . . $n_M$. Then, the readings at the seven FPA pixels each of which is optically filtered by a corresponding band-pass filter of FIG. 6A can be represented by:

$g_1 = f_1 + n_1$, $g_2 = f_2 + n_2$ $g_3 = f_3 + n_3$, $g_4 = f_4 + n_4$, $g_5 = f_5 + n_5$, $g_6 = f_6 + n_6$ $g_7 = f_7 + n_7$,

These readings (pixel measurements) $g_i$ are estimates of the spectral intensities $f_i$. The estimates $g_i$ are not equal to the corresponding $f_i$ values because of the measurement errors $n_i$. However, if the measurement noise distribution has zero mean, then the ensemble mean of each individual measurement can be considered to be equal to the true value, i.e. $\langle g_i \rangle = f_i$. Here, the angle brackets indicate the operation of calculating the ensemble mean of a stochastic variable. The variance of the measurement can, therefore, be represented as:

$\langle (g_i - f_i)^2 \rangle = \langle n_i^2 \rangle = \sigma^2$

In embodiments utilizing spectrally-multiplexed filters, in comparison with the embodiments utilizing band-pass filters, the amount of radiant energy transmitted by each of the spectrally-multiplexed LP or SP filters towards a given detector element can exceed that transmitted through a spectral band of a band-pass filter. In this case, the intensities of light corresponding to the independent spectral bands can be reconstructed by computational means. Such embodiments can be referred to as a "multiplex design".

One matrix of such "multiplexed filter" measurements includes a Hadamard matrix requiring "negative" filters that may not be necessarily appropriate for the optical embodiments disclosed herein. An S-matrix approach (which is restricted to having a number of filters equal to an integer that is multiple of four minus one) or a row-doubled Hadamard matrix (requiring a number of filters to be equal to an integer multiple of eight) can be used in various embodiments. Here, possible numbers of filters using an S-matrix setup are 3, 7, 11, etc and, if a row-doubled Hadamard matrix setup is used, then the possible number of filters is 8, 16, 24, etc. For example, the goal of the measurement may be to measure seven spectral band $f_i$ intensities using seven measurements $g_i$ as follows:

$g_1 = f_1 + 0 + f_3 + 0 + f_5 + 0 + f_7 + n_1$, $g_2 = 0 + f_2 + f_3 + 0 + 0 + f_6 + f_7 + n_2$ $g_3 = f_1 + f_2 + 0 + 0 + f_5 + 0 + f_7 + n_3$ $g_4 = 0 + 0 + 0 + f_4 + f_5 + f_7 + f_8 + n_4$ $g_5 = f_1 + 0 + f_3 + f_4 + 0 + f_6 + 0 + n_5$ $g_6 = 0 + f_2 + f_3 + f_4 + f_5 + 0 + 0 + n_6$ $g_7 = f_1 + f_2 + 0 + f_4 + 0 + 0 + f_7 + n_7$

Optical transmission characteristics of the filters described above are depicted in FIG. 6B. Here, a direct estimate of the $f_i$ is no longer provided through a relationship similar to $\langle g_i \rangle = f_i$. Instead, if a "hat" notation is used to denote an estimate of a given value, then a linear combination of the measurements can be used such as, for example, $$\hat{f}_1 = \frac{1}{4}(+g_1 - g_2 + g_3 - g_4 + g_5 - g_6 + g_7),$$

$$\hat{f}_2 = \frac{1}{4}(-g_1 + g_2 + g_3 - g_4 - g_5 + g_6 + g_7),$$

$$\hat{f}_3 = \frac{1}{4}(+g_1 + g_2 - g_3 - g_4 + g_5 + g_6 - g_7),$$

$$\hat{f}_4 = \frac{1}{4}(-g_1 - g_2 - g_3 + g_4 + g_5 + g_6 + g_7),$$

$$\hat{f}_5 = \frac{1}{4}(+g_1 - g_2 + g_3 + g_4 - g_5 + g_6 - g_7),$$

$$\hat{f}_6 = \frac{1}{4}(-g_1 + g_2 + g_3 + g_4 + g_5 - g_6 - g_7),$$

$$\hat{f}_7 = \frac{1}{4}(+g_1 + g_2 - g_3 + g_4 - g_5 - g_6 + g_7),$$

These $\hat{f}_i$ are unbiased estimates when the $n_i$ are zero mean stochastic variables, so that $\langle \hat{f}_i - f_i \rangle = 0$. The measurement variance corresponding to $i^{th}$ measurement is given by the equation below:

$$\langle (\hat{f}_i - f_i)^2 \rangle = \frac{7}{16} \sigma^2$$

From the above equation, it is observed that by employing spectrally-multiplexed system the signal-to-noise ratio (SNR) of a measurement is improved by a factor of $\sqrt{16/7} = 1.51 = 1.51 \sqrt{7/16} = 0.66$.

For N channels, the SNR improvement achieved with a spectrally-multiplexed system can be expressed as $(N+1)/(2\sqrt{N})$. For example, an embodiment employing 12 spectral channels (N=12) is characterized by a SNR improvement, over a non-spectrally-multiplexed system, comprising a factor of up to 1.88.

Figure 6C:
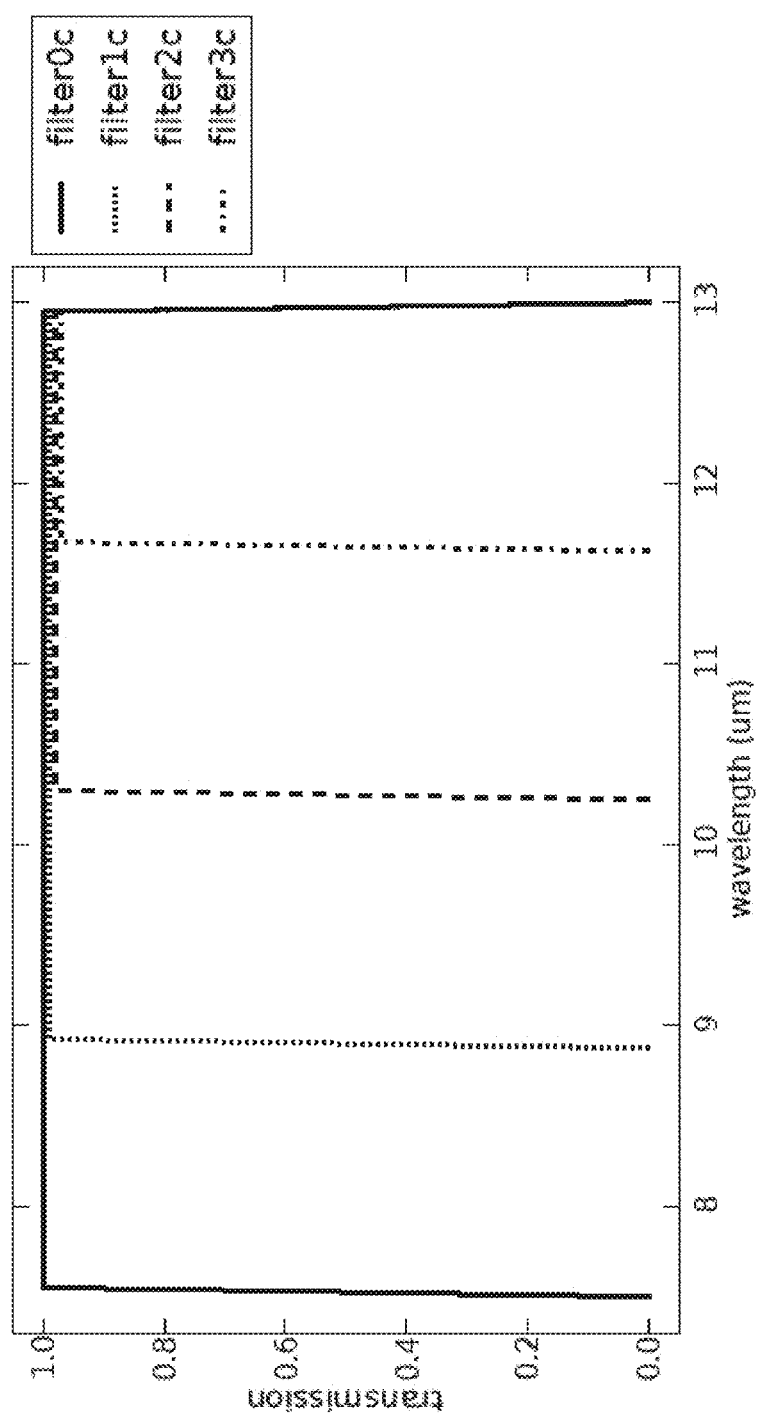
FIG. 6C shows theoretical plots of transmission characteristics of spectrally multiplexed long-pass filter combination used in an embodiment of the system.
Figure 6D:
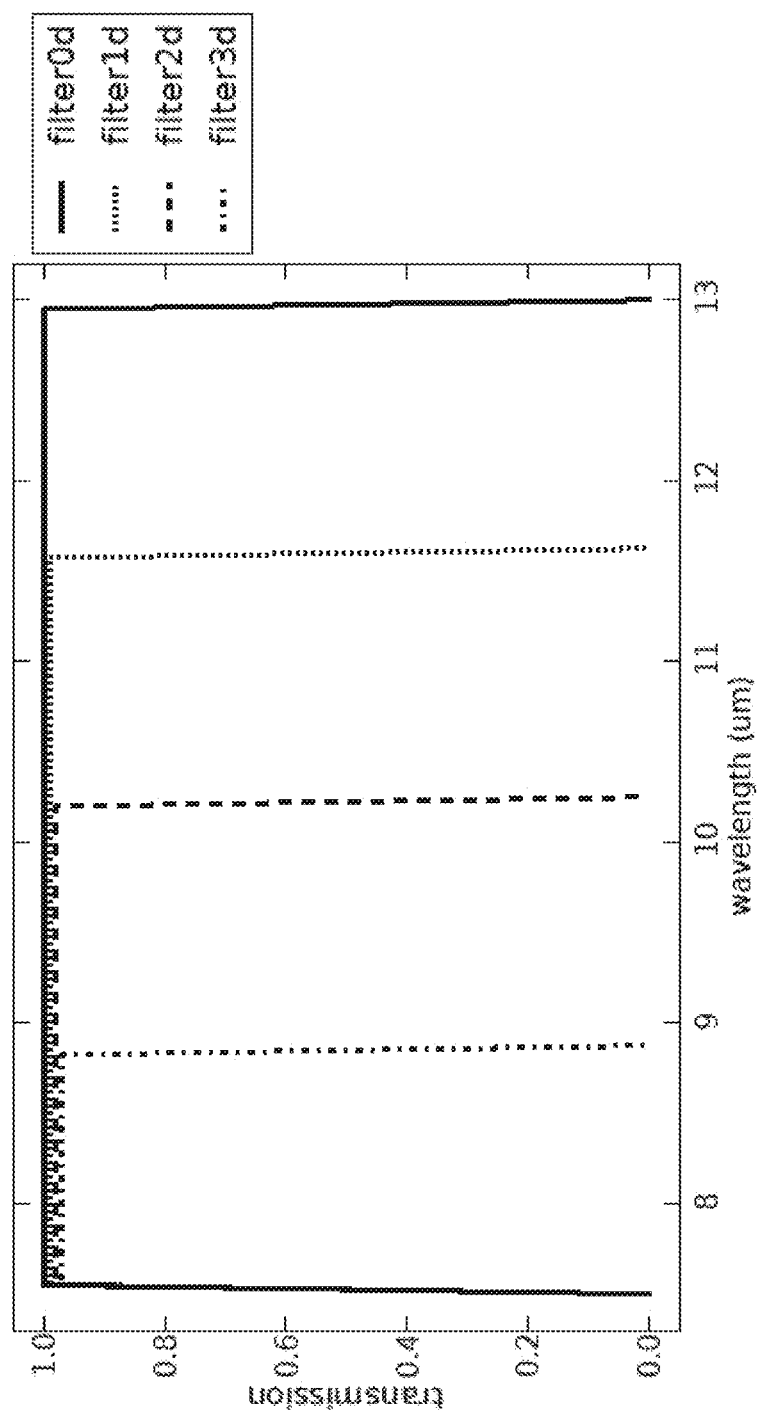
FIG. 6D shows theoretical plots of transmission characteristics of spectrally multiplexed short-pass filter combination used in an embodiment of the system.

Two additional examples of related spectrally-multiplexed filter arrangements 0c through 3c and 0d through 3d that can be used in various embodiments of the imaging systems described herein are shown in FIGS. 6C and 6D, respectively. The spectrally-multiplexed filters shown in FIGS. 6C and 6D can be used in embodiments of imaging systems employing uncooled FPAs (such as microbolometers). FIG. 6C illustrates a set of spectrally-multiplexed long-wavelength pass (LP) filters used in the system. An LP filter generally attenuates shorter wavelengths and transmits (passes) longer wavelengths (e.g., over the active range of the target IR portion of the spectrum). A single spectral channel having a transmission characteristic corresponding to the difference between the spectral transmission curves of at least two of these LP filters can be used to procure imaging data for the data cube using an embodiment of the system described herein. In various implementations, the spectral filters disposed with respect to the different FPAs can have different spectral characteristics. In various implementations, the spectral filters may be disposed in front of only some of the FPAs while the remaining FPAs may be configured to receive unfiltered light. For example, in some implementations, only 9 of the 12 detectors in the 4×3 array of detectors described above may be associated with a spectral filter while the other 3 detectors may be configured to received unfiltered light. Such a system may be configured to acquire spectral data in 10 different spectral channels in a single data acquisition event.

The use of microbolometers, as detector-noise-limited devices, in turn not only can benefit from the use of spectrally multiplexed filters, but also does not require cooling of the imaging system during normal operation. In contrast to imaging systems that include highly sensitive FPA units with reduced noise characteristics, the embodiments of imaging systems described herein can employ less sensitive microbolometers without compromising the SNR. This result is at least in part due to the snap-shot/non-scanning mode of operation.

As discussed above, an embodiment may optionally, and in addition to a temperature-controlled reference unit (for example temperature controlled shutters such as shutters 160, 460a, 460b), employ a field reference component (e.g., field reference aperture 338 in FIG. 3A), or an array of field reference components (e.g., filed reference apertures 438 in FIG. 4), to enable dynamic calibration. Such dynamic calibration can be used for spectral acquisition of one or more or every data cube. Such dynamic calibration can also be used for a spectrally-neutral camera-to-camera combination to enable dynamic compensation of parallax artifacts. The use of the temperature-controlled reference unit (for example, temperature-controlled shutter system 160) and field-reference component(s) facilitates maintenance of proper calibration of each of the FPAs individually and the entire FPA unit as a whole.

In particular, and in further reference to FIGS. 1, 2, 3, and 4, the temperature-controlled unit generally employs a system having first and second temperature zones maintained at first and second different temperatures. For example, shutter system of each of the embodiments 100, 200, 300 and 400 can employ not one but at least two temperature-controlled shutters that are substantially parallel to one another and transverse to the general optical axis 226 of the embodiment(s) 100, 200, 300, 400. Two shutters at two different temperatures may be employed to provide more information for calibration; for example, the absolute value of the difference between FPAs at one temperature as well as the change in that difference with temperature change can be recorded. Referring, for example, to FIG. 4, in which such multi-shutter structure is shown, the use of multiple shutters enables the user to create a known reference temperature difference perceived by the FPAs 456. This reference temperature difference is provided by the IR radiation emitted by the shutter(s) 460a, 460b when these shutters are positioned to block the radiation from the object 110. As a result, not only the offset values corresponding to each of the individual FPAs pixels can be adjusted but also the gain values of these FPAs. In an alternative embodiment, the system having first and second temperature zones may include a single or multi-portion piece. This single or multi-portion piece may comprise for example a plate. This piece may be mechanically-movable across the optical axis with the use of appropriate guides and having a first portion at a first temperature and a second portion at a second temperature.

Indeed, the process of calibration of an embodiment of the imaging system starts with estimating gain and offset by performing measurements of radiation emanating, independently, from at least two temperature-controlled shutters of known and different radiances. The gain and offset can vary from detector pixel to detector pixel. Specifically, first the response of the detector unit 456 to radiation emanating from one shutter is carried out. For example, the first shutter 460a blocks the FOV of the detectors 456 and the temperature $T_1$ is measured directly and independently with thermistors. Following such initial measurement, the first shutter 460a is removed from the optical path of light traversing the embodiment and another second shutter (for example, 460b) is inserted in its place across the optical axis 226 to prevent the propagation of light through the system. The temperature of the second shutter 460b can be different than the first shutter ($T_2 \neq T_1$). The temperature of the second shutter 460b is also independently measured with thermistors placed in contact with this shutter, and the detector response to radiation emanating from the shutter 460b is also recorded. Denoting operational response of FPA pixels (expressed in digital numbers, or "counts") as $g_i$ to a source of radiance $L_i$, the readings corresponding to the measurements of the two shutters can be expressed as:

$$g_1 = \gamma L_1(T_1) + g_{offset}$$

$$g_2 = \gamma L_2(T_2) + g_{offset}$$

Here, $g_{offset}$ is the pixel offset value (in units of counts), and $\gamma$ is the pixel gain value (in units of counts per radiance unit). The solutions of these two equations with respect to the two unknowns $g_{offset}$ and $\gamma$ can be obtained if the values of $g_1$ and $g_2$ and the radiance values $L_1$ and $L_2$ are available. These values can, for example, be either measured by a reference instrument or calculated from the known temperatures $T_1$ and $T_2$ together with the known spectral response of the optical system and FPA. For any subsequent measurement, one can then invert the equation(s) above in order to estimate the radiance value of the object from the detector measurement, and this can be done for each pixel in each FPA within the system.

As already discussed, and in reference to FIGS. 1 through 4, the field-reference apertures may be disposed in an object space or image space of the optical system, and dimensioned to block a particular portion of the IR radiation received from the object. In various implementations, the field-reference aperture, the opening of which can be substantially similar in shape to the boundary of the filter array (for example, and in reference to a filter array of FIGS. 3B, 5B—e.g., rectangular). The field-reference aperture can be placed in front of the objective lens (124, 224, 324, 424) at a distance that is at least several times (in one implementation—at least five times) larger than the focal length of the lens such that the field-reference aperture is placed closer to the object. Placing the field-reference aperture closer to the object can reduce the blurriness of the image. In the embodiment 400 of FIG. 4, the field-reference aperture can be placed within the depth of focus of an image conjugate plane formed by the front objective lens 424. The field reference, generally, can facilitate, effectuates and/or enable dynamic compensation in the system by providing a spectrally known and temporally-stable object within every scene to reference and stabilize the output from the different FPAs in the array.

Because each FPA's offset value is generally adjusted from each frame to the next frame by the hardware, comparing the outputs of one FPA with another can have an error that is not compensated for by the static calibration parameters $g_{offset}$ and $\gamma$ established, for example, by the movable shutters 160. In order to ensure that FPAs operate in radiometric agreement over time, it is advantageous for a portion of each detector array to view a reference source (such as the field reference 338 in FIG. 3A, for example) over a plurality of frames obtained over time. If the reference source spectrum is known a priori (such as a blackbody source at a known temperature), one can measure the response of each FPA to the reference source in order to estimate changes to the pixel offset value. However, the temperature of the reference source need not be known. In such implementations, dynamic calibration of the different detectors can be performed by monitoring the change in the gain and the offset for the various detectors from the time the movable shutters used for static calibration are removed. An example calculation of the dynamic offset proceeds as follows.

Among the FPA elements in an array of FPAs in an embodiment of the imaging system, one FPA can be selected to be the "reference FPA". The field reference temperature measured by all the other FPAs can be adjusted to agree with the field reference temperature measured by the reference as discussed below. The image obtained by each FPA includes a set of pixels obscured by the field reference 338. Using the previously obtained calibration parameters $g_{offset}$ and $\gamma$ (the pixel offset and gain), the effective blackbody temperature $T_i$ of the field reference as measured by each FPA is estimated using the equation below:

$$T_i = \text{mean}\{(g+\Delta g_i + g_{offset})/\gamma\} = \text{mean}\{(g-g_{offset})/\gamma\} + \Delta T_i$$

Using the equation above, the mean value over all pixels that are obscured by the field reference is obtained. In the above equation $\Delta g_i$ is the difference in offset value of the current frame from $\Delta g_{offset}$ obtained during the calibration step. For the reference FPA, $\Delta g_i$ can be simply set to zero. Then, using the temperature differences measured by each FPA, one obtains $$T_i - T_{ref} = \text{mean}\{(g+\Delta g_i + g_{offset})/\gamma\} + \Delta T_i - \text{mean}\{(g-g_{offset})/\gamma\} = \Delta T_i$$

Once $\Delta T_i$ for each FPA is measured, its value can be subtracted from each image in order to force operational agreement between such FPA and the reference FPA. While the calibration procedure has been discussed above in reference to calibration of temperature, a procedurally similar methodology of calibration with respect to radiance value can also be implemented.

Examples of Methodology of Measurements.

Prior to optical data acquisition using an embodiment of the IR imaging system as described herein, one or more, most, or potentially all the FPAs of the system can be calibrated. For example, greater than 50%, 60%, 70%, 80% or 90% of the FPAs 336 can be initially calibrated. As shown in FIG. 3A, these FPAs 336 may form separate images of the object using light delivered in a corresponding optical channel that may include the combination of the corresponding front objective and re-imaging lenses 324, 128. The calibration procedure can allow formation of individual images in equivalent units (so that, for example, the reading from the FPA pixels can be re-calculated in units of temperature or radiance units, etc.). Moreover, the calibration process can also allow the FPAs (e.g., each of the FPAs) to be spatially co-registered with one another so that a given pixel of a particular FPA can be optically re-mapped through the optical system to the same location at the object as the corresponding pixel of another FPA.

To achieve at least some of these goals, a spectral differencing method may be employed. The method involves forming a difference image from various combinations of the images from different channels. In particular, the images used to form difference images can be registered by two or more different FPAs in spectrally distinct channels having different spectral filters with different spectral characteristics. Images from different channels having different spectral characteristics will provide different spectral information. Comparing (e.g., subtracting) these images, can therefore yield valuable spectral based information. For example, if the filter element of the array of spectral filters 130 corresponding to a particular FPA 336 transmits light from the object 110 including a cloud of gas, for example, with a certain spectrum that contains the gas absorption peak or a gas emission peak while another filter element of the array of spectral filters 130 corresponding to another FPA 336 does not transmit such spectrum, then the difference between the images formed by the two FPAs at issue will highlight the presence of gas in the difference image.

A shortcoming of the spectral differencing method is that contributions of some auxiliary features associated with imaging (not just the target species such as gas itself) can also be highlighted in and contribute to the difference image. Such contributing effects include, to name just a few, parallax-induced imaging of edges of the object, influence of magnification differences between the two or more optical channels, and differences in rotational positioning and orientation between the FPAs. While magnification-related errors and FPA-rotation-caused errors can be compensated for by increasing the accuracy of the instrument construction as well as by post-processing of the acquired imaging, parallax is scene-induced and is not so easily correctable. In addition, the spectral differencing method is vulnerable to radiance calibration errors. Specifically, if one FPA registers radiance of light from a given feature of the object as having a temperature of 40° C., for example, while the data from another FPA represents the temperature of the same object feature as being 39° C., then such feature of the object will be enhanced or highlighted in the difference image (formed at least in part based on the images provided by these two FPAs) due to such radiance-calibration error.

One solution to some of such problems is to compare (e.g., subtract) images from the same FPA obtained at different instances in time. For example, images can be compared to or subtracted from a reference image obtained at another time. Such reference image, which is subtracted from other later obtained images, may be referred to as a temporal reference image. This solution can be applied to spectral difference images as well. For example, the image data resulting from spectral difference images can be normalized by the data corresponding to a temporal reference image. For instance, the temporal reference images can be subtracted from the spectral difference image to obtain the temporal difference image. This process is referred to, for the purposes of this disclosure, as a temporal differencing algorithm or method and the resultant image from subtracting the temporal reference image from another image (such as the spectral difference image) is referred to as the temporal difference image. In some embodiments where spectral differencing is employed, a temporal reference image may be formed, for example, by creating a spectral difference image from the two or more images registered by the two or more FPAs at a single instance in time. This spectral difference image is then used as a temporal reference image. The temporal reference image can then be subtracted from other later obtained images to provide normalization that can be useful in subtracting out or removing various errors or deleterious effects. For example, the result of the algorithm is not affected by a prior knowledge of whether the object or scene contains a target species (such as gas of interest), because the algorithm can highlight changes in the scene characteristics. Thus, a spectral difference image can be calculated from multiple spectral channels as discussed above based on a snap-shot image acquisition at any later time and can be subtracted from the temporal reference image to form a temporal difference image. This temporal difference image is thus a normalized difference image. The difference between the two images (the temporal difference image) can highlight the target species (gas) within the normalized difference image, since this species was not present in the temporal reference frame. In various embodiments, more than two FPAs can be used both for registering the temporal reference image and a later-acquired difference image to obtain a better SNR figure of merit. For example, if two FPAs are associated with spectral filters having the same spectral characteristic, then the images obtained by the two FPAs can be combined after they have been registered to get a better SNR figure.

While the temporal differencing method can be used to reduce or eliminate some of the shortcomings of the spectral differencing, it can introduce unwanted problems of its own. For example, temporal differencing of imaging data is less sensitive to calibration and parallax induced errors than the spectral differencing of imaging data. However, any change in the imaged scene that is not related to the target species of interest (such as particular gas, for example) is highlighted in a temporally-differenced image. Thus such change in the imaged scene may be erroneously perceived as a location of the target species triggering, therefore, an error in detection of target species. For example, if the temperature of the background against which the gas is being detected changes (due to natural cooling down as the day progresses, or increases due to a person or animal or another object passing through the FOV of the IR imaging system), then such temperature change produces a signal difference as compared to the measurement taken earlier in time. Accordingly, the cause of the scenic temperature change (the cooling object, the person walking, etc.) may appear as the detected target species (such as gas). It follows, therefore, that an attempt to compensate for operational differences among the individual FPAs of a multi-FPA IR imaging system with the use of methods that turn on spectral or temporal differencing can cause additional problems leading to false detection of target species. Among these problems are scene-motion-induced detection errors and parallax-caused errors that are not readily correctable and/or compensatable. Accordingly, there is a need to compensate for image data acquisition and processing errors caused by motion of elements within the scene being imaged. Various embodiments of data processing algorithms described herein address and fulfill the need to compensate for such motion-induced and parallax-induced image detection errors.

In particular, to reduce or minimize parallax-induced differences between the images produced with two or more predetermined FPAs, another difference image can be used that is formed from the images of at least two different FPAs to estimate parallax effects. Parallax error can be determined by comparing the images from two different FPAs where the position between the FPAs is known. The parallax can be calculated from the known relative position difference. Differences between the images from these two FPAs can be attributed to parallax, especially, if the FPA have the same spectral characteristics, for example have the same spectral filter or both have no spectral filters. Parallax error correction, however, can still be obtained from two FPAs that have different spectral characteristics or spectral filters, especially if the different spectral characteristics, e.g., the transmission spectra of the respective filters are known and/or negligible. Use of more than two FPAs or FPAs of different locations such as FPAs spaced farther apart can be useful. For example, when the spectral differencing of the image data is performed with the use of the difference between the images collected by the outermost two cameras in the array (such as, for example, the FPAs corresponding to filters 2 and 3 of the array of filters of FIG. 5A), a difference image referred to as a "difference image 2-3" is formed. In this case, the alternative "difference image 1-4" is additionally formed from the image data acquired by, for example, the alternative FPAs corresponding to filters 1 and 4 of FIG. 5A. Assuming or ensuring that both of these two alternative FPAs have approximately the same spectral sensitivity to the target species, the alternative "difference image 1-4" will highlight pixels corresponding to parallax-induced features in the image. Accordingly, based on positive determination that the same pixels are highlighted in the spectral "difference image 2-3" used for target species detection, a conclusion can be made that the image features corresponding to these pixels are likely to be induced by parallax and not the presence of target species in the imaged scene. It should be noted that compensation of parallax can also be performed using images created by individual re-imaging lenses, 128*a*, when using a single FPA or multiple FPA's as discussed above. FPAs spaced apart from each other in different directions can also be useful. Greater than 2, for example, 3 or 4, or more FPAs can be used to establish parallax for parallax correction. In certain embodiments two central FPAs and one corner FPA are used for parallax correction. These FPA may, in certain embodiments, have substantially similar or the same spectral characteristics, for example, have filters having similar or the same transmission spectrum or have no filter at all.

Another capability of the embodiments described herein is the ability to perform the volumetric estimation of a gas cloud. This can be accomplished by using (instead of compensating or negating) the parallax induced effects described above. In this case, the measured parallax between two or more similar spectral response images (e.g., two or more channels or FPAs) can be used to estimate a distance between the imaging system and the gas cloud or between the imaging system and an object in the field of view of the system. The parallax induced transverse image shift, d, between two images is related to the distance, z, between the cloud or object 110 and the imaging system according to the equation $z=-sz'/d$. Here, s, is the separation between two similar spectral response images, and z' is the distance to the image plane from the back lens. The value for z' is typically approximately equal to the focal length f of the lens of the imaging system. Once the distance z between the cloud and the imaging system is calculated, the size of the gas cloud can be determined based on the magnification, m=f/z, where each image pixel on the gas cloud, $\Delta x'$, corresponds to a physical size in object space $\Delta x=\Delta x'/m$. To estimate the volume of the gas cloud, a particular symmetry in the thickness of the cloud based on the physical size of the cloud can be assumed. For example, the cloud image can be rotated about a central axis running through the cloud image to create a three dimensional volume estimate of the gas cloud size. It is worth noting that in the embodiments described herein only a single imaging system is required for such volume estimation. Indeed, due to the fact that the information about the angle at which the gas cloud is seen by the system is decoded in the parallax effect, the image data includes the information about the imaged scene viewed by the system in association with at least two angles.

When the temporal differencing algorithm is used for processing the acquired imaging data, a change in the scene that is not caused by the target species can inadvertently be highlighted in the resulting image. In various embodiments, compensation for this error makes use of the temporal differencing between two FPAs that are substantially equally spectrally sensitive to the target species. In this case, the temporal difference image will highlight those pixels the intensity of which have changed in time (and not in wavelength). Therefore, subtracting the data corresponding to these pixels on both FPAs, which are substantially equally spectrally sensitive to the target species, to form the resulting image, excludes the contribution of the target species to the resulting image. The differentiation between (i) changes in the scene due to the presence of target species and (ii) changes in the scene caused by changes in the background not associated with the target species is, therefore, possible. In some embodiments, these two channels having the same or substantially similar spectral response so as to be substantially equally spectrally sensitive to the target species may comprise FPAs that operate using visible light. It should also be noted that, the data acquired with a visible light FPA (when present as part of the otherwise IR imaging system) can also be used to facilitate such differentiation and compensation of the motion-caused imaging errors. Visible cameras generally have much lower noise figure than IR cameras (at least during daytime). Consequently, the temporal difference image obtained with the use of image data from the visible light FPA can be quite accurate. The visible FPA can be used to compensate for motion in the system as well as many potential false-alarms in the scene due to motion caused by people, vehicles, birds, and steam, for example, as long as the moving object can be observed in the visible region of the spectra. This has the added benefit of providing an additional level of false alarm suppression without reducing the sensitivity of the system since many targets such as gas clouds cannot be observed in the visible spectral region. In various implementations, an IR camera can be used to compensate for motion artifacts.

Another method for detection of the gases is to use a spectral unmixing approach. A spectral unmixing approach assumes that the spectrum measured at a detector pixel is composed of a sum of component spectra (e.g., methane and other gases). This approach attempts to estimate the relative weights of these components needed to derive the measurement spectrum. The component spectra are generally taken from a predetermined spectral library (for example, from data collection that has been empirically assembled), though sometimes one can use the scene to estimate these as well (often called "endmember determination"). In various embodiments, the image obtained by the detector pixel is a radiance spectrum and provides information about the brightness of the object. To identify the contents of a gas cloud in the scene and/or to estimate the concentration of the various gases in the gas cloud, an absorption/emission spectrum of the various gases of interest can be obtained by comparing the measured brightness with an estimate of the expected brightness. The spectral unmixing methodology can also benefit from temporal, parallax, and motion compensation techniques.

In various embodiments, a method of identifying the presence of a target species in the object includes obtaining the radiance spectrum (or the absorption spectrum) from the object in a spectral region indicative of the presence of the target species and calculating a correlation (e.g., a correlation coefficient) by correlating the obtained radiance spectrum (or the absorption spectrum) with a reference spectrum for the target species. The presence or absence of the target species can be determined based on an amount of correlation (e.g., a value of correlation coefficient). For example, the presence of the target species in the object can be confirmed if the amount of correlation or the value of correlation coefficient is greater than a threshold. In various implementations, the radiance spectrum (or the absorption spectrum) can be obtained by obtaining a spectral difference image between a filtered optical channel and/or another filtered optical channel/unfiltered optical channel or any combinations thereof.

For example, an embodiment of the system configured to detect the presence of methane in a gas cloud comprises optical components such that one or more of the plurality of optical channels is configured to collect IR radiation to provide spectral data corresponding to a discrete spectral band located in the wavelength range between about 7.9 μm and about 8.4 μm corresponding to an absorption peak of methane. The multispectral data obtained in the one or more optical channels can be correlated with a predetermined absorption spectrum of methane in the wavelength range between about 7.9 and 8.4 μm. In various implementations, the predetermined absorption spectrum of methane can be saved in a database or a reference library accessible by the system. Based on an amount of correlation (e.g., a value of correlation coefficient), the presence or absence of methane in the gas cloud can be detected.

Examples of Practical Embodiments and Operation

The embodiment 300 of FIG. 3 is configured to employ 12 optical channels and 12 corresponding microbolometer FPAs 336 to capture a video sequence substantially immediately after performing calibration measurements. The video sequence corresponds to images of a standard laboratory scene and the calibration measurements are performed with the use of a reference source including two shutters, as discussed above, one at room temperature and one 5° C. above room temperature. The use of 12 FPAs allows increased chance of simultaneous detection and estimation of the concentrations of about 8 or 9 gases present at the scene. In various embodiments, the number of FPAs 336 can vary, depending on the balance between the operational requirements and consideration of cost.

Due to the specifics of operation in the IR range of the spectrum, the use of the so-called noise-equivalent temperature difference (or NETD) is preferred and is analogous to the SNR commonly used in visible spectrum instruments. The array of microbolometer FPAs 336 is characterized to perform at NETD≤72 mK at an f-number of 1.2. Each measurement was carried out by summing four consecutive frames, and the reduction in the NETD value expected due to such summation would be described by corresponding factor of √4=2. Under ideal measurement conditions, therefore, the FPA NETD should be about 36 mK.

It is worth noting that the use of optically-filtered FPAs in various embodiments of the system described herein can provide a system with higher number of pixels. For example, embodiments including a single large format microbolometer FPA array can provide a system with large number of pixels. Various embodiments of the systems described herein can also offer a high optical throughput for a substantially low number of optical channels. For example, the systems described herein can provide a high optical throughput for a number of optical channels between 4 and 50. By having a lower number of optical channels (e.g., between 4 and 50 optical channels), the systems described herein have wider spectral bins which allows the signals acquired within each spectral bin to have a greater integrated intensity.

An advantage of the embodiments described herein over various scanning based hyperspectral systems that are configured for target species detection (for example, gas cloud detection) is that, the entire spectrum can be resolved in a snapshot mode (for example, during one image frame acquisition by the FPA array). This feature enables the embodiments of the imaging systems described herein to take advantage of the compensation algorithms such as the parallax and motion compensation algorithms mentioned above. Indeed, as the imaging data required to implement these algorithms are collected simultaneously with the target-species related data, the compensation algorithms are carried out with respect to target-species related data and not with respect to data acquired at another time interval. This rapid data collection thus improves the accuracy of the data compensation process. In addition, the frame rate of data acquisition is much higher. For example, embodiments of the imaging system described herein can operate at video rates from about 5 Hz and higher. For example, various embodiments described herein can operate at frame rates from about 5 Hz to about 60 Hz or 200 Hz. Thus, the user is able to recognize in the images the wisps and swirls typical of gas mixing without blurring out of these dynamic image features and other artifacts caused by the change of scene (whether spatial or spectral) during the lengthy measurements. In contradistinction, scanning based imaging systems involve image data acquisition over a period of time exceeding a single-snap-shot time and can, therefore, blur the target gas features in the image and inevitably reduce the otherwise achievable sensitivity of the detection. This result is in contrast to embodiments of the imaging system described herein that are capable of detecting the localized concentrations of gas without it being smeared out with the areas of thinner gas concentrations. In addition, the higher frame rate also enables a much faster response rate to a leak of gas (when detecting such leak is the goal). For example, an alarm can trigger within fractions of a second rather than several seconds.

Figure 7:
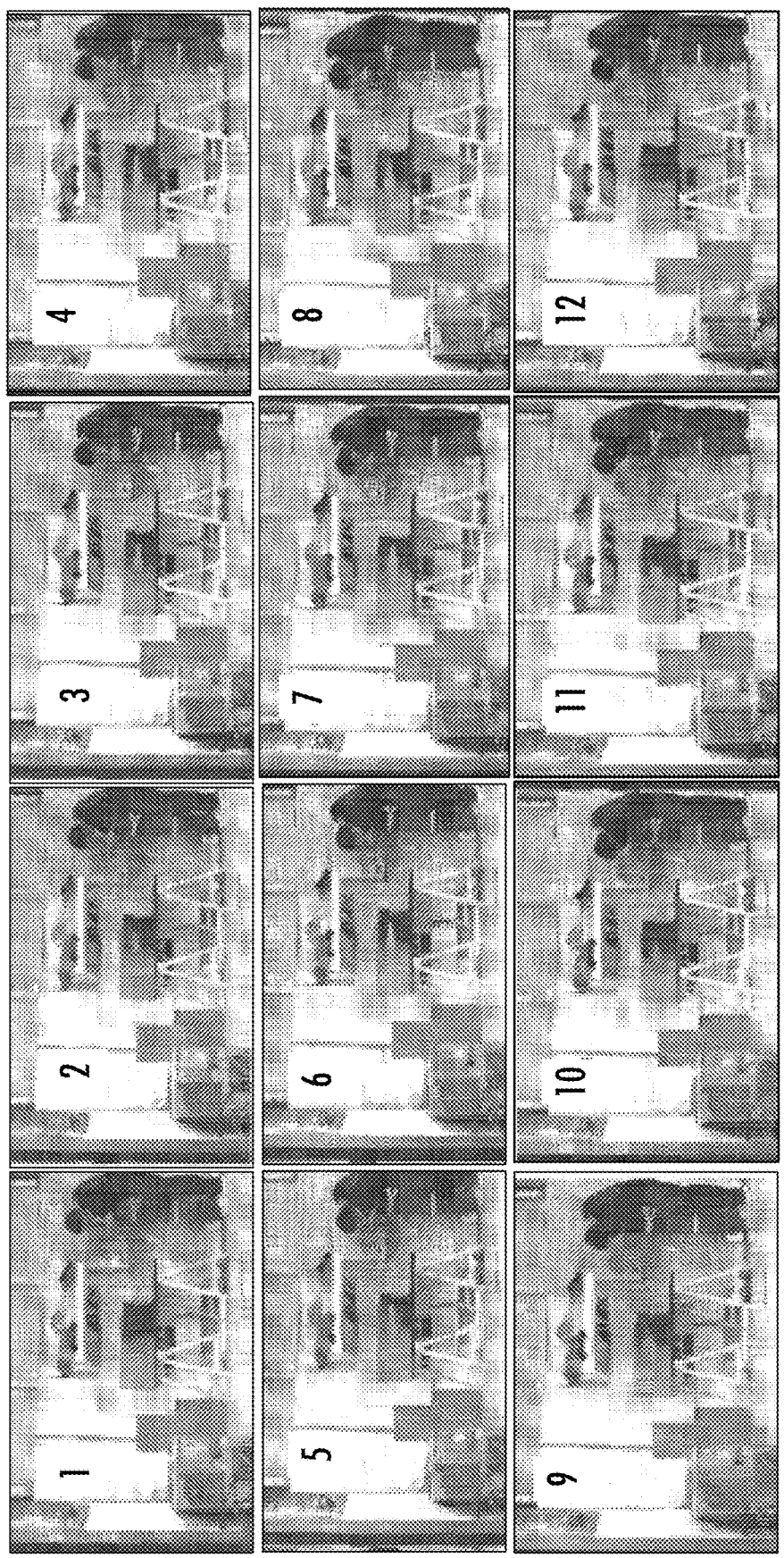
FIG. 7 is a set of video-frames illustrating operability of an embodiment of the system used for gas detection.

To demonstrate the operation and gas detection capability of the imaging systems described herein, a prototype was constructed in accordance with the embodiment 300 of FIG. 3A and used to detect a hydrocarbon gas cloud of propylene at a distance of approximately 10 feet. FIG. 7 illustrates video frames 1 through 12 representing gas-cloud-detection output 710 (seen as a streak of light) in a sequence from t=1 to t=12. The images 1 through 12 are selected frames taken from a video-data sequence captured at a video-rate of 15 frames/sec. The detected propylene gas is shown as a streak of light 710 (highlighted in red) near the center of each image. The first image is taken just prior to the gas emerging from the nozzle of a gas-contained, while the last image represents the system output shortly after the nozzle has been turned off.

Figure 8A:
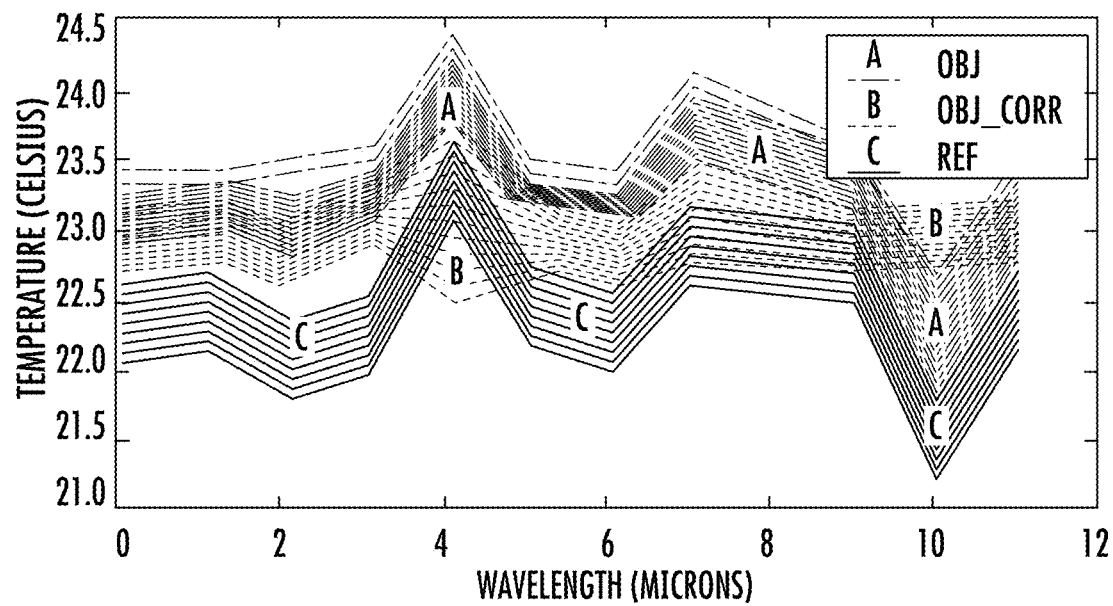
FIGS. 8A and 8B are plots (on axes of wavelength in microns versus the object temperature in Celsius representing effective optical intensity of the object) illustrating results of dynamic calibration of an embodiment of the system.
Figure 8B:
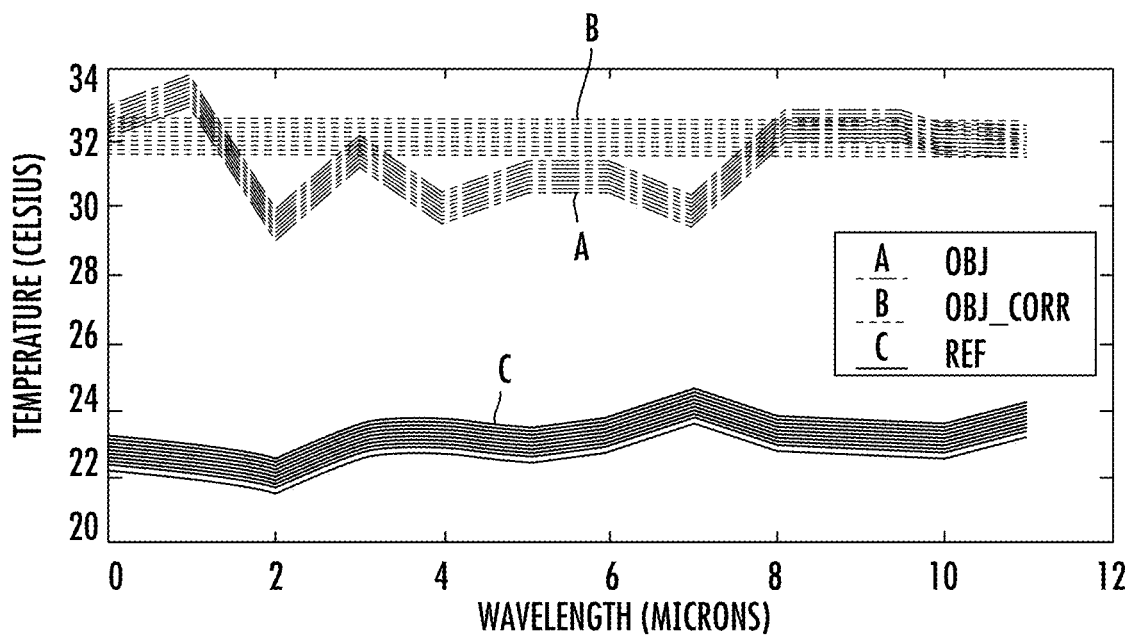

The same prototype of the system can also demonstrate the dynamic calibration improvement described above by imaging the scene surrounding the system (the laboratory) with known temperature differences. The result of implementing the dynamic correction procedure is shown in FIGS. 8A, 8B, where the curves labeled "obj" (or "A") represent temperature estimates of an identified region in the scene. The abscissa in each of the plots of FIGS. 8A, 8B indicates the number of a FPA, while the ordinate corresponds to temperature (in degrees C.). Accordingly, it is expected that when all detector elements receive radiant data that, when interpreted as the object's temperature, indicates that the object's temperature perceived by all detector elements is the same, any given curve would be a substantially flat line. Data corresponding to each of the multiple "obj" curves are taken from a stream of video frames separated from one another by about 0.5 seconds (for a total of 50 frames). The recorded "obj" curves shown in FIG. 8A indicate that the detector elements disagree about the object's temperature, and that difference in object's temperature perceived by different detector elements is as high as about 2.5° C. In addition, all of the temperature estimates are steadily drifting in time, from frame to frame. The curves labeled "ref" (or "C") correspond to the detectors' estimates of the temperature of the aperture 338 of the embodiment 300 of FIG. 3A. The results of detection of radiation carried out after each detector pixel has been subjected to the dynamic calibration procedure described above are expressed with the curved labeled "obj corr" (or "B"). Now, the difference in estimated temperature of the object among the detector elements is reduced to about 0.5° C. (thereby improving the original reading at least by a factor of 5).

FIG. 8B represents the results of similar measurements corresponding to a different location in the scene (a location which is at a temperature about 9° C. above the estimated temperature of the aperture 338 of FIG. 3A). As shown, the correction algorithm discussed above is operable and effective and applicable to objects kept at different temperature. Accordingly, the algorithm is substantially temperature independent.

Dynamic Calibration Elements and References

Figure 9A:
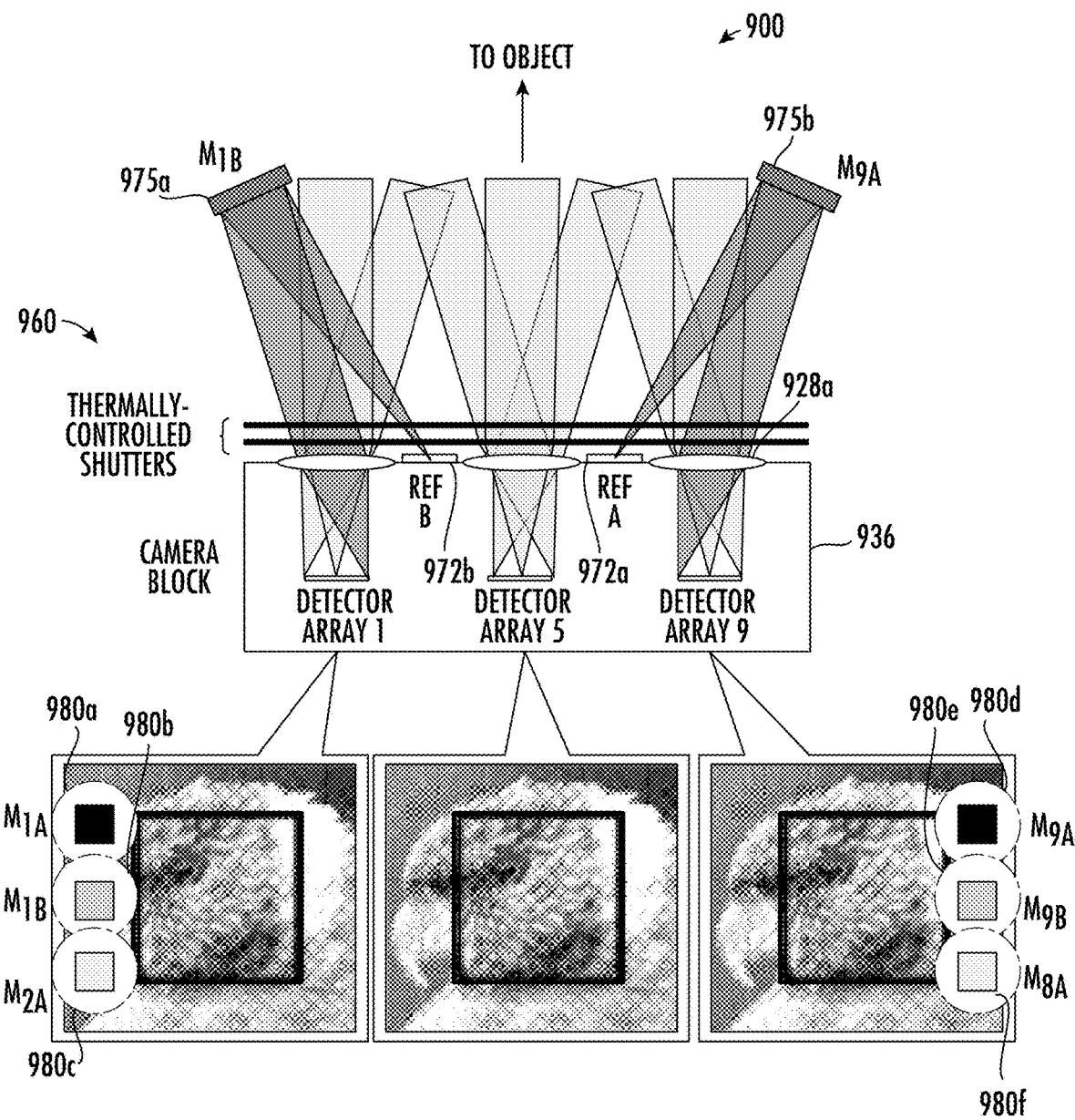
FIGS. 9A and 9B illustrate a cross-sectional view of different embodiments of an imaging system comprising an arrangement of reference sources and mirrors that can be used for dynamic calibration.
Figure 9B:
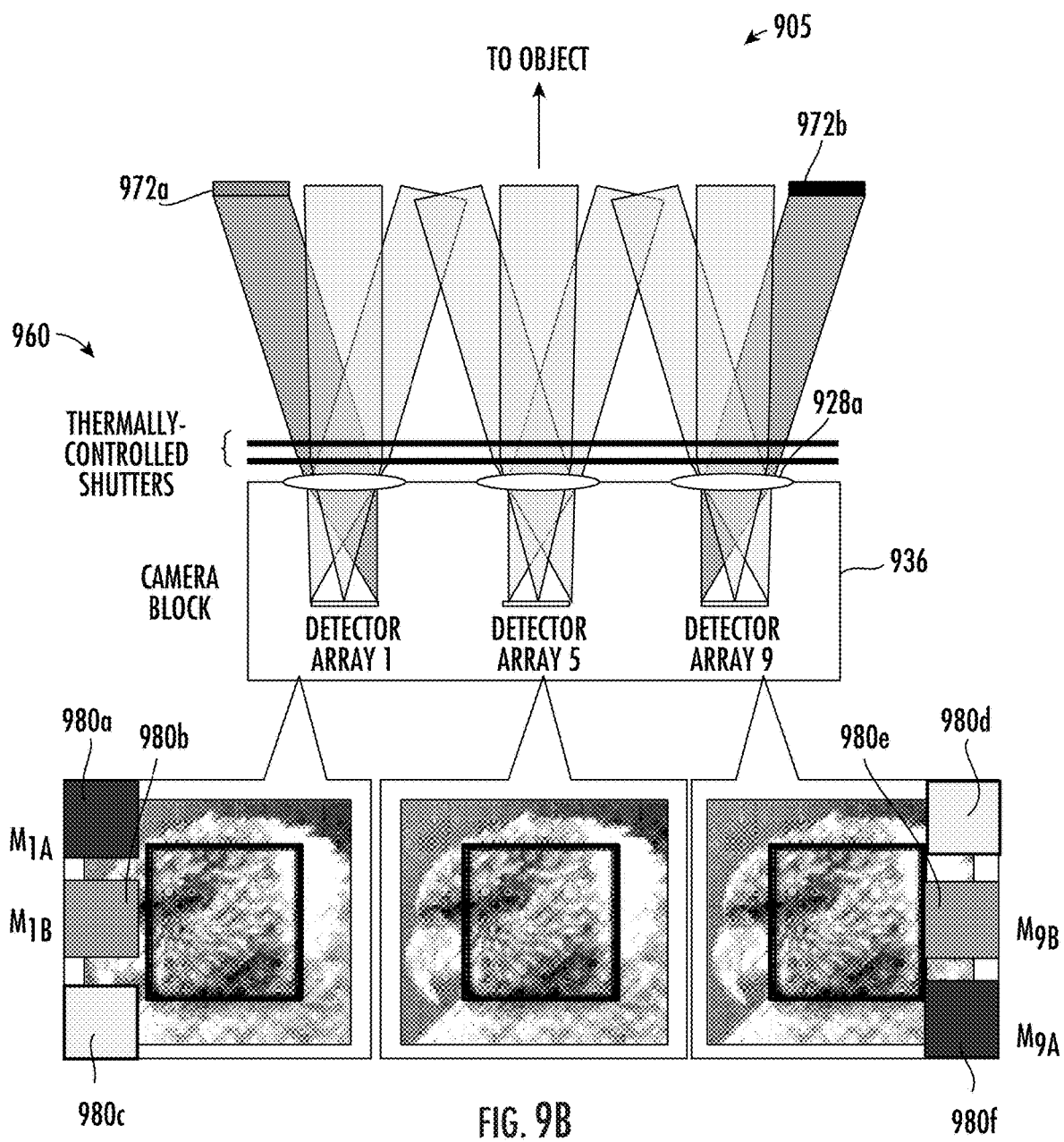

FIGS. 9A and 9B illustrates schematically different implementations 900 and 905 respectively of the imaging system that include a variety of temperature calibration elements to facilitate dynamic calibration of the FPAs. The temperature calibration elements can include mirrors 975*a*, 975*b* (represented as $M_{1A}$, $M_{9A}$, etc.) as well as reference sources 972*a* and 972*b*. The implementation 900 can be similarly configured as the embodiment 300 and include one or more front objective lens, a divided aperture, one or more spectral filters, an array of imaging lenses 928*a* and an imaging element 936. In various implementations, the imaging element 936 (e.g., camera block) can include an array of cameras. In various implementations, the array of cameras can comprise an optical FPA unit. The optical FPA unit can comprise a single FPA, an array of FPAs. In various implementations, the array of cameras can include one or more detector arrays represented as detector array 1, detector array 5, detector array 9 in FIGS. 9A and 9B. In various embodiments, the FOV of each of the detector arrays 1, 5, 9 can be divided into a central region and a peripheral region. Without any loss of generality, the central region of the FOV of each of the detector arrays 1, 5, 9 can include the region where the FOV of all the detector arrays 1, 5, 9 overlap. In the embodiment illustrated in FIG. 9A, the reference sources 972a and 972b are placed at a distance from the detector arrays 1, 5, 9, for example, and mirrors 975a and 975b that can image them onto the detector arrays are then placed at the location of the scene reference aperture (e.g., 338 of FIG. 3A).

In FIG. 9A, the mirrors 975a and 975b are configured to reflect radiation from the reference sources 972a and 972b (represented as ref A and ref B). The mirrors 975a and 975b can be disposed away from the central FOV of the detector arrays 1, 5, 9 such that the central FOV is not blocked or obscured by the image of the reference source 972a and 972b. In various implementations, the FOV of the detector array 5 could be greater than the FOV of the detector arrays 1 and 9. In such implementations, the mirrors 975a and 975b can be disposed away from the central FOV of the detector array 5 at a location such that the reference source 972a and 972b is imaged by the detector array 5. The mirrors 975a and 975b may comprise imaging optical elements having optical power that image the reference sources 972a and 972b onto the detector arrays 1 and 9. In this example, the reference sources 972a and 972b can be disposed in the same plane as the re-imaging lenses 928a, however, the reference sources 972a and 972b can be disposed in a different plane or in different locations. For example, the reference sources 972a and 972b can be disposed in a plane that is conjugate to the plane in which the detector array 1, detector array 5, and detector array 9 are disposed such that a focused image of the reference sources 972a and 972b is formed by the detector arrays. In some implementations, the reference sources 972a and 972b can be disposed in a plane that is spaced apart from the conjugate plane such that a defocused image of the reference sources 972a and 972b is formed by the detector arrays. In various implementations, the reference sources 972a and 972b need not be disposed in the same plane.

As discussed above, in some embodiments, the reference sources 972a and 972b are imaged onto the detector array 1 and detector array 9, without much blur such that the reference sources 972a and 972b are focused. In contrast, in other embodiments, the image of reference sources 972a and 972b formed on the detector array 1, and detector array 9 are blurred such that the reference sources 972a and 972b are defocused, and thereby provide some averaging, smoothing, and/or low pass filtering. The reference sources 972a and 972b may comprise a surface of known temperature and may or may not include a heater or cooler attached thereto or in thermal communication therewith. For example, the reference source 972a and 972b may comprises heaters and coolers respectively or may comprise a surface with a temperature sensor and a heater and sensor respectively in direct thermal communication therewith to control the temperature of the reference surface. In various implementations, the reference sources 972a and 972b can include a temperature controller configured to maintain the reference sources 972a and 972b at a known temperature. In some implementations, the reference sources 972a and 972b can be associated with one or more sensors that measure the temperature of the reference sources 972a and 972b and communicate the measured temperature to the temperature controller. In some implementations, the one or more sensors can communicate the measured temperature to the data-processing unit. In various implementations, the reference sources 972a and 972b may comprise a surface of unknown temperature. For example, the reference sources may comprise a wall of a housing comprising the imaging system. In some implementations, the reference sources 972a and 972b can comprise a surface that need not be associated with sensors, temperature controllers. However, in other implementations, the reference sources 972a and 972b can comprise a surface that can be associated with sensors, temperature controllers.

In FIG. 9B, the temperature-calibration elements comprise temperature-controlled elements 972a and 972b (e.g., a thermally controlled emitter, a heating strip, a heater or a cooler) disposed a distance from the detector arrays 1, 5, 9. In various embodiments, the temperature-controlled elements 972a and 972b can be disposed away from the central FOV of the detector arrays 1, 5, 9 such that the central FOV is not blocked or obscured by the image of the reference source 972a and 972b. The radiation emitted from the reference sources 972a and 972b is also imaged by the detector array 936 along with the radiation incident from the object. Depending on the position of the reference sources 972a and 972b the image obtained by the detector array of the reference sources can be blurred (or defocused) or sharp (or focused). The images 980a, 980b, 980c, 980d, 980e and 980f of the temperature-controlled elements 972a and 972b can be used as a reference to dynamically calibrate the one or more cameras in the array of cameras.

In the implementations depicted in FIGS. 9A and 9B, the detector arrays 1, 5 and 9 are configured to view (or image) both the reference sources 972a and 972b. Accordingly, multiple frames (e.g., every or substantially every frame) within a sequence of images contains one or more regions in the image in which the object image has known thermal and spectral properties. This allows multiple (e.g., most or each) cameras within the array of cameras to be calibrated to agree with other (e.g., most or every other) camera imaging the same reference source(s) or surface(s). For example, detector arrays 1 and 9 can be calibrated to agree with each other. As another example, detector arrays 1, 5 and 9 can be calibrated to agree with each other. In various embodiments, the lenses 928a provide blurred (or defocused) images of the reference sources 972a, 972b on the detector arrays 1 and 9 because the location of the reference sources are not exactly in a conjugate planes of the detector arrays 1 and 9. Although the lenses 928a are described as providing blurred or defocused images, in various embodiments, reference sources or surfaces are imaged on the detectors arrays 1, 5, 9 without such blur and defocus and instead are focused images. Additionally optical elements may be used, such as for example, the mirrors shown in FIG. 9A to provide such focused images.

The temperature of the reference sources 972b, 972a can be different. For example, the reference source 972a can be at a temperature $T_A$, and the reference source 972b can be at a temperature $T_B$ lower than the temperature $T_A$. A heater can be provided under the temperature-controlled element 972a to maintain it at a temperature $T_A$, and a cooler can be provided underneath the temperature-controlled element 972b to maintain it at a temperature $T_B$. In various implementations, the embodiments illustrated in FIGS. 9A and 9B can be configured to image a single reference source 972 instead of two references sources 972a and 972b maintained at different temperatures. It is understood that the single reference source need not be thermally controlled. For example, in various implementations, a plurality of detectors in the detector array can be configured to image a same surface of at least one calibration element whose thermal and spectral properties are unknown. In such implementations, one of the plurality of detectors can be configured as a reference detector and the temperature of the surface of the at least one calibration element imaged by the plurality of detectors can be estimated using the radiance spectrum obtained by the reference detector. The remaining plurality of detectors can be calibrated such that their temperature and/or spectral measurements agree with the reference detector. For example, detector arrays 1 and 9 can be calibrated to agree with each other. As another example, detector arrays 1, 5 and 9 can be calibrated to agree with each other.

The reference sources 972a and 972b can be coated with a material to make it behave substantially as a blackbody (for which the emission spectrum is known for any given temperature). If a temperature sensor is used at the location of each reference source, then the temperature can be tracked at these locations. As a result, the regions in the image of each camera (e.g., on the detector arrays 1 and 9) in which the object has such known temperature (and, therefore, spectrum) can be defined. A calibration procedure can thus be used so that most of the cameras (if not every camera) so operated agrees, operationally, with most or every other camera, for objects at the temperatures represented by those two sources. Calibrating infrared cameras using sources at two different temperatures is known as a "two-point" calibration, and assumes that the measured signal at a given pixel is linearly related to the incident irradiance. Since this calibration can be performed during multiple, more, or even every frame of a sequence, it is referred to as a "dynamic calibration".

An example of the dynamic calibration procedure is as follows. If there is a temperature sensor on the reference sources or reference surface, then the temperature measurements obtained by these temperature sensors can be used to determine their expected emission spectra. These temperature measurements are labeled as $T_A[R]$, $T_B[R]$, and $T_C[R]$ for the "reference temperatures" of sources/surfaces A, B, and C. These temperature measurements can be used as scalar correction factors to apply to the entire image of a given camera, forcing it to agree with the reference temperatures. Correcting the temperature estimate of a given pixel from T to T' can use formulae analogous to those discussed below in reference to FIGS. 10A, 10B, 10C. If no direct temperature sensor is used, then one of the cameras can be used instead. This camera can be referred to as the "reference camera". In this case, the same formulae as those provided in paragraph below can be used, but with $T_A[R]$ and $T_B[R]$ representing the temperatures of the reference sources/surfaces A and B as estimated by the reference camera. By applying the dynamic calibration correction formulae, all of the other cameras are forced to match the temperature estimates of the reference camera.

In the configuration illustrated in FIG. 9B, the reference sources 972a and 972b are placed such that the images of the sources on the detector arrays are blurred. The configuration illustrated in FIG. 9A is similar to the system 400 illustrated in FIG. 4 where the reference sources are placed at an intermediate image plane (e.g., a conjugate image plane). In this configuration, the array of reference apertures, similar to reference apertures 438a in FIG. 4, will have an accompanying array of reference sources or reference surfaces such that the reference sources or surfaces (e.g., each reference source or surface) are imaged onto a camera or a detector array such as FPAs 1, 5, 9. With this approach, the reference source or surface images are at a conjugate image plane and thus are not appreciably blurred, so that their images can be made to block a smaller portion of each camera's field of view.

A "static" calibration (a procedure in which the scene is largely blocked with a reference source such as the moving shutters 960 in FIGS. 9A and 9B, so that imaging of an unknown scene cannot be performed in parallel with calibration) allows a plurality of the cameras (for example, most or each camera) to accurately estimate the temperature of a plurality of elements (for example, most or each element in the scene) immediately after the calibration is complete. It cannot, however, prevent the cameras' estimates from drifting away from one another during the process of imaging an unknown scene. The dynamic calibration can be used to reduce or prevent this drift, so that all cameras imaging a scene can be forced to agree on the temperature estimate of the reference sources/surfaces, and adjust this correction during every frame.

Figure 10A:
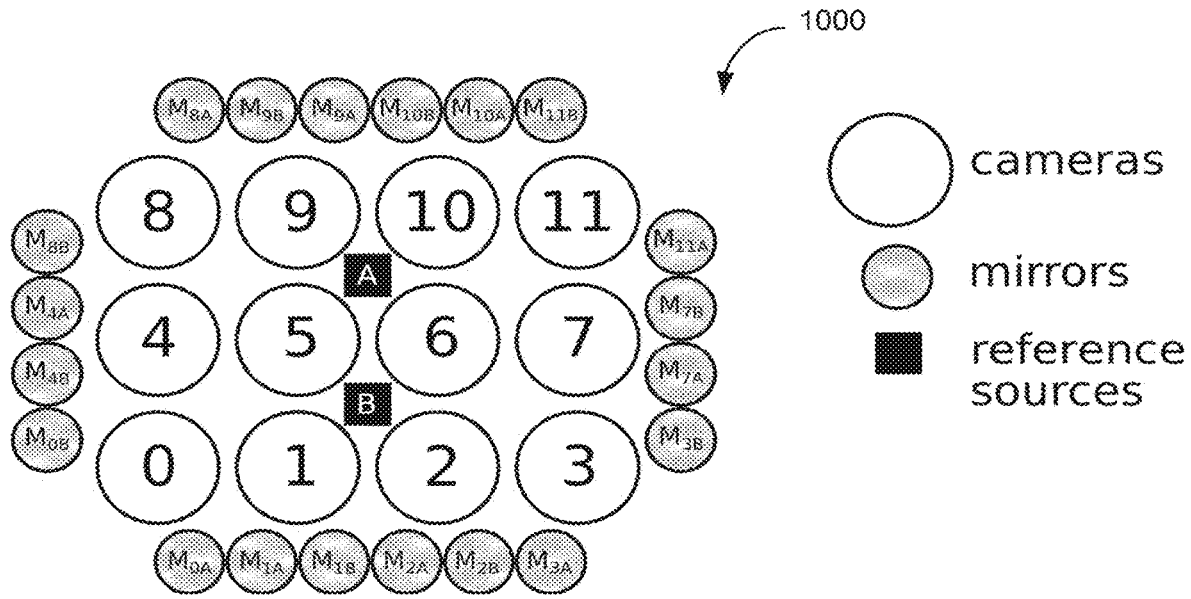
FIGS. 10A-10C illustrate a plan view of different embodiments of an imaging system comprising an arrangement of reference sources and mirrors that can be used for dynamic calibration.

FIG. 10A illustrates schematically a related embodiment 1000 of the imaging system, in which one or more mirrors $M_{0A}, \ldots M_{11A}$ and $M_{0B}, \ldots M_{11B}$ are placed within the fields of view of one or more cameras 0, . . . , 11, partially blocking the field of view. The cameras 0, . . . , 11 are arranged to form an outer ring of cameras including cameras 0, 1, 2, 3, 7, 11, 10, 9, 8 and 4 surrounding the central cameras 5 and 6. In various implementations, the FOV of the central cameras 5 and 6 can be less than or equal to the FOV of the outer ring of cameras 0, 1, 2, 3, 7, 11, 10, 9, 8 and 4. In such implementations, the one or more mirrors $M_{0A}, \ldots M_{11A}$ and $M_{0B}, \ldots M_{11B}$ can be placed outside the central FOV of the cameras 5 and 6 and is placed in a peripheral FOV of the cameras outer ring of cameras 0, 1, 2, 3, 7, 11, 10, 9, 8 and 4 which does not overlap with the central FOV of the cameras 5 and 6 such that the reference sources A and B are not imaged by the cameras 5 and 6. In various implementations, the FOV of the central cameras 5 and 6 can be greater than the FOV of the outer ring of cameras 0, 1, 2, 3, 7, 11, 10, 9, 8 and 4. In such implementations, the one or more mirrors $M_{0A}, \ldots M_{11A}$ and $M_{0B}, \ldots M_{11B}$ can be placed in a peripheral FOV of the cameras 5 and 6 which does overlap with the central FOV of the outer ring of cameras 0, 1, 2, 3, 7, 11, 10, 9, 8 and 4 such that the reference sources A and B are imaged by the cameras 5 and 6.

This design is an enhancement to the systems 300 and 400 shown in FIGS. 3A and 4A. In the system 1000 shown in FIG. 10A, an array of two or more imaging elements (curved mirrors, for example) is installed at a distance from the FPAs, for example, in the plane of the reference aperture 160 shown in FIG. 3A. These elements (mirror or imaging elements) are used to image one or more temperature-controlled reference sources A and B onto the detector elements of two or more of the cameras. The primary difference between embodiment 1000 and embodiment 300 or 400 is that now a plurality or most or all of the outer ring of cameras in the array can image both the reference sources A and B instead of imaging one of the two reference source A and B. Accordingly, most or all of the outer ring of cameras image an identical reference source or an identical set of reference sources (e.g., both the reference sources A and B) rather than using different reference sources for different cameras or imaging different portions of the reference sources as shown in FIGS. 3A and 4A. Thus, this approach improves the robustness of the calibration, as it eliminates potential failures and errors due to the having additional thermal sensors estimating each reference source.

The imaging elements in the system 1000 (shown as mirrors in FIGS. 10A and 10B) image one or more controlled-temperature reference sources or a surface of a calibration element (shown as A and B in FIGS. 10A and 10B) into the blocked region of the cameras' fields of view.

Figure 10B:
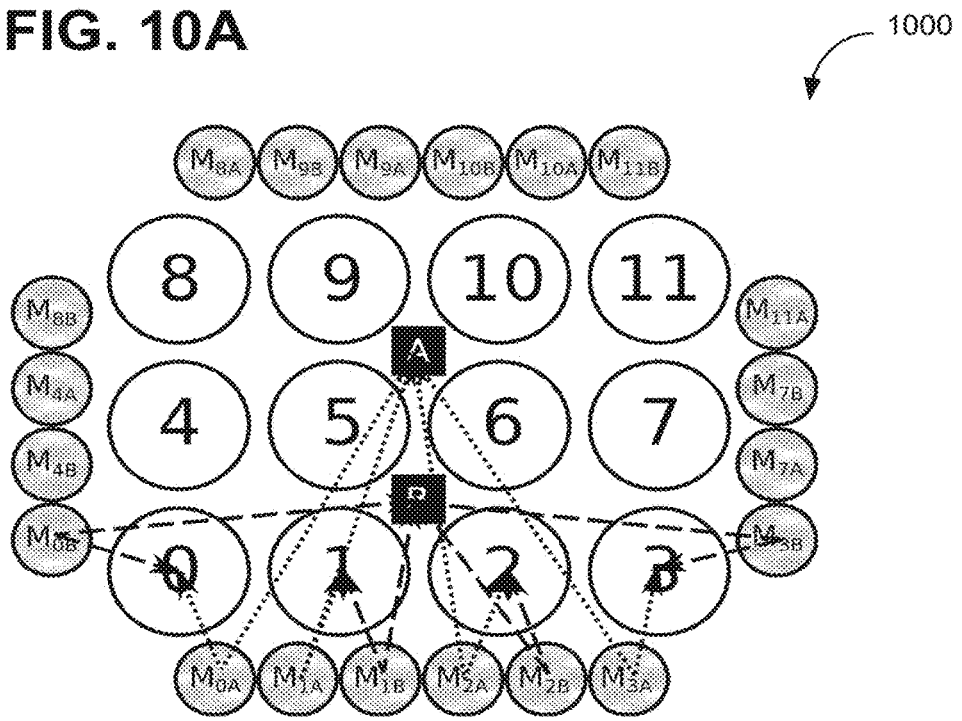

FIG. 10B shows an example in which mirror $M_{0A}$ images reference source/surface A onto camera 0, and mirror $M_{0B}$ images reference source/surface B onto camera 0, and likewise for cameras 1, 2, and 3. This way, each of the mirrors is used to image a reference source/surface onto a detector array of a camera, so that many, most, or every frame within a sequence of images contains one or more regions in the image in which the object image has known thermal and spectral properties. This approach allows most of the camera, if not each camera, within the array of cameras to be calibrated to agree with most or every other camera imaging the same reference source or sources. For example, cameras 0, 1, 2, 3, 7, 11, 10, 9, 8 and 4 can be calibrated to agree with each other. As another example, cameras 0, 1, 2 and 3 can be calibrated to agree with each other. As yet another example, cameras 0, 1, 2, 3, 7, 11, 10, 9, 8, 4, 5 and 6 can be calibrated to agree with each other. Accordingly, in various implementations, two, three, four, five, six, seven, eight, nine, ten, eleven or twelve cameras can be calibrated to agree with each other. In certain embodiments, however, not all the cameras are calibrated to agree with each other. For example, one, two, or more cameras may not be calibrated to agree with each other while others may be calibrated to agree with each other. In various embodiments, these mirrors may be configured to image the reference sources/surfaces A and B onto different respective pixels a given FPA. Without any loss of generality, FIGS. 10A and 10B represent a top view of the embodiment shown in FIG. 9A.

Figure 10C:
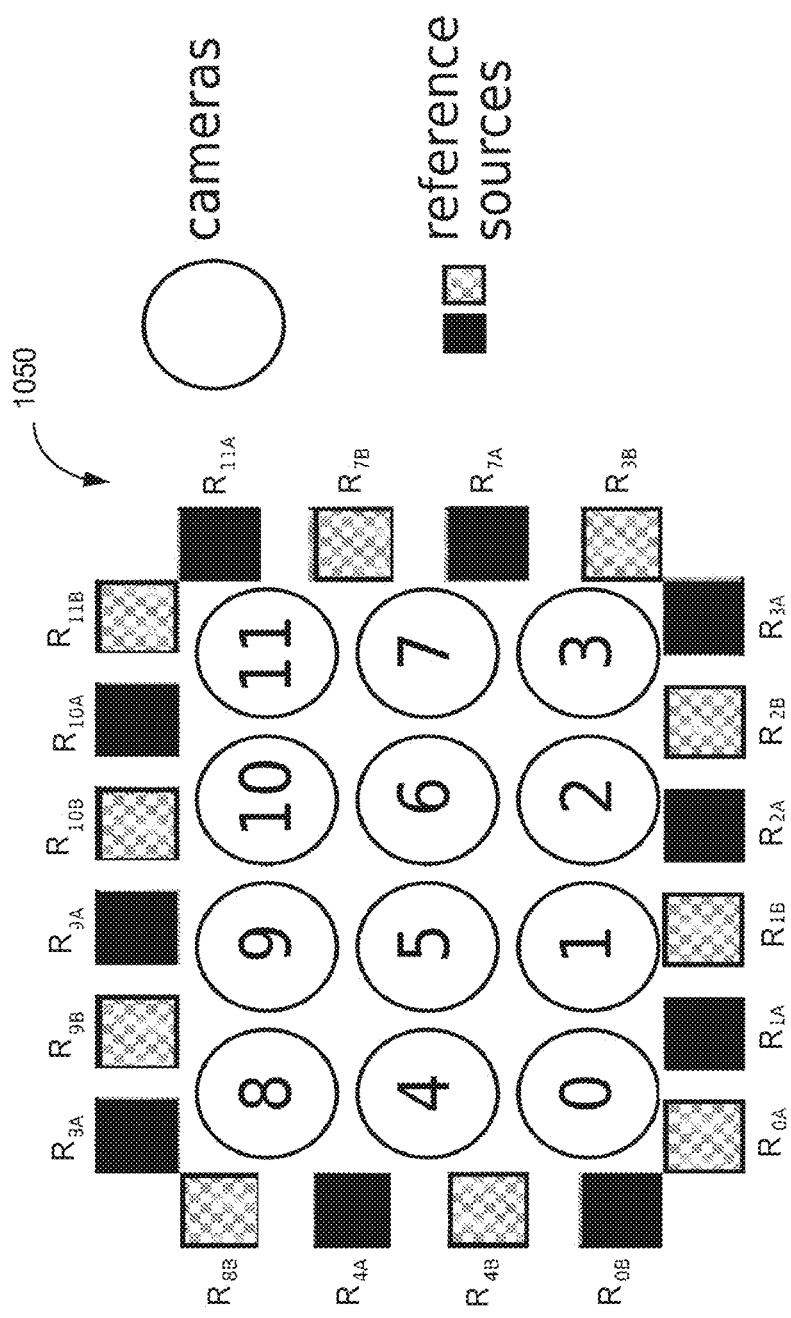

FIG. 10C illustrates schematically a related embodiment 1050 of the imaging system, in which one or more reference sources $R_{0A}, \ldots R_{11A}$ and $R_{0B}, \ldots, R_{11B}$ are disposed around the array of detectors 0, ..., 11. In various implementations, the one or more reference sources $R_{0A}, \ldots, R_{11A}$ and $R_{0B}, \ldots, R_{11A}$ can be a single reference source that is imaged by the detectors 0, ..., 11. In various implementations, central detector arrays 5 and 6 can have a FOV that is equal to or lesser than the FOV of the outer ring of the detectors 0, 1, 2, 3, 7, 11, 10, 9, 8 and 4. In such implementations, the reference sources $R_{0A}, \ldots R_{11A}$ can be disposed away from the central FOV of the detector arrays 5 and 6 such that the radiation from the reference sources $R_{0A}, \ldots R_{11A}$ is imaged only by the outer ring of detectors 0, 1, 2, 3, 7, 11, 10, 9, 8 and 4. In various implementations, central detector arrays 5 and 6 can have a FOV that is greater than the FOV of the outer ring of the detectors 0, 1, 2, 3, 7, 11, 10, 9, 8 and 4. In such implementations, the reference sources $R_{0A}, \ldots, R_{11A}$ can be disposed in the peripheral FOV of the detector arrays 5 and 6 such that the radiation from the reference sources $R_{0A}, \ldots R_{11A}$ is imaged only by the outer ring of detectors 0, 1, 2, 3, 7, 11, 10, 9, 8 and 4. The radiation from the reference sources $R_{0A}, \ldots, R_{11A}$ is therefore imaged by the outer ring of detectors 0, 1, 2, 3, 7, 11, 10, 9, 8 and 4 as well as central cameras 5 and 6. Without any loss of generality, FIG. 10C represents a top view of the embodiment shown in FIG. 9B.

In various implementations, a heater can be provided underneath, adjacent to, or in thermal communication with reference source/surface A to give it a higher temperature $T_A$, and a cooler can be provided underneath, adjacent to, or in thermal communication with reference source B to give it a lower temperature $T_B$. In various implementations, the embodiments illustrated in FIGS. 10A, 10B and 10C can be configured to image a single reference source A instead of two references sources A and B maintained at different temperatures. As discussed above, the embodiments illustrated in FIGS. 10A, 10B and 10C can be configured to image a same surface of a calibration element. In such implementations, the temperature of the surface of the calibration element need not be known. Many, most or each reference source/surface can be coated with a material to make it behave approximately as a blackbody, for which the emission spectrum is known for any given temperature. If many, most, or each camera in the array of cameras images both of references A and B, so that there are known regions in the image of these cameras in which the object has a known temperature (and therefore spectrum), then one can perform a calibration procedure. This procedure can provide that many, most or every camera so operated agrees with various, most, or every other camera, for objects at the temperatures represented by those two sources. For example, two, three, four, five, six, seven, eight, nine, ten, eleven or twelve cameras can be calibrated to agree with each other. In certain embodiments, however, not all the cameras are calibrated to agree with each other. For example, one, two, or more cameras may not be calibrated to agree with each other while others may be calibrated to agree with each other. As discussed above, calibration of infrared cameras using sources at two different temperatures is known as a "two-point" calibration, and assumes that the measured signal at a given pixel is linearly related to the incident irradiance.

The dynamic calibration is used to obtain a corrected temperature T' from the initial temperature T estimated at each pixel in a camera using the following formulae:

$$T'[x,y,c] = (T[x,y,c] - T_A[R])G[c] + T_A[R]$$

where is $T_A[R]$ is a dynamic offset correction factor, and, $$G[c] = \frac{T_B[R] - T_A[R]}{T_B[c] - T_A[c]},$$

is a dynamic gain correction factor. The term c discussed above is a camera index that identifies the camera whose data is being corrected.

III. Examples of a Mobile DAISI System

The DAISI systems disclosed herein can be configured to be installed at a suitable location on a long-term basis, according to some embodiments. For example, the DAISI systems disclosed in Section II above can be affixed to a fixture mounted to the ground at a location to continuously or periodically monitor the presence of gases or chemicals at the location. In some embodiments, for example, the DAISI systems can be attached to a pole, post, or any suitable fixture at the location to be monitored. In such arrangements, the DAISI system can continuously or periodically capture multispectral, multiplexed image data of the scene, and an on-board or remote computing unit can process the captured image data to identify or characterize gases or chemicals at the location. A communications module can communicate data relating to the identified gases or chemicals to any suitable external system, such as a central computing server, etc. For such long-term installations of the DAISI system, the installation site may include a power source (e.g., electrical transmission lines connected to a junction box at the site) and network communications equipment (e.g., network wiring, routers, etc.) to provide network communication between the DAISI system and the external systems.

It can be advantageous to provide a mobile DAISI system configured to be worn or carried by a user. For example, it may be unsuitable or undesirable to install a DAISI system at some locations on a long-term basis. As an example, some oil well sites may not have sufficient infrastructure, such as power sources or network communication equipment, to support the DAISI system. In addition, it can be challenging to move the DAISI system from site to site to monitor different locations. For example, installing and removing the DAISI system from a site for transport may involve substantial effort and time for the user when the system is connected to infrastructure at the site to be monitored. Accordingly, it can be desirable to provide a DAISI system that can be used independently of the facilities or infrastructure at the site to be monitored. Furthermore, it can be advantageous to implement the DAISI system in a form factor and with a weight that can be carried or worn by a user. For example, a mobile DAISI system can enable the user to easily transport the system from site-to-site, while monitoring the presence of gases or chemicals in real-time.

It should be appreciated that each of the systems disclosed herein can be used to monitor potential gas leaks in any suitable installation site, including, without limitation, drilling rigs, refineries, pipelines, transportations systems, ships or other vessels (such as off-shore oil rigs, trains, tanker trucks, petro-chemical plants, chemical plants, etc. In addition, each of the embodiments and aspects disclosed and illustrated herein such as above, e.g., with respect to FIGS. 1-10C, can be used in combination with each of the embodiments disclosed and illustrated herein with respect to FIGS. 11A-14C.

FIG. 11A is a schematic diagram illustrating a mobile infrared imaging system 1000 (e.g., a mobile or portable DAISI system) configured to be carried or worn by a human user 1275. The user 1275 may wear a hat or helmet 1200 when he travels to a site to be monitored, such as an oil well site, a refinery, etc. The system 1000 shown in FIG. 11A is attached to the helmet 1200 by way of a support 1204 that securely mounts the system 1000 to the helmet 1200. For example, the support 1204 can comprise a fastener, a strap, or any other suitable structure. Advantageously, mounting the system 1000 to the helmet 1200 can enable the user 1275 to capture images within the system's field of view (FOV) by turning his head to face a particular location to be monitored. For example, the user 1275 can walk through the site and can capture video images of each portion of the site, e.g., various structures that may be susceptible to gas or chemical leaks, such as valves, fittings, etc. Thus, in the embodiment shown in FIG. 11A, the user 1275 can image each portion of the site by facing the area to be imaged and ensuring that the system 1000 is activated. In addition, by mounting the system 1000 to the user's helmet 1200, the user 1275 may use his hands for other tasks while the system 1000 images the site. Although the system 1000 of FIG. 11A is shown as being mounted to the user's helmet 1200, it should be appreciated that the system 1000 can instead be worn on other parts of the user's clothing or can be carried by the user, e.g., in a bag, case, or other suitable container. Furthermore, in some embodiments, a wind sensor can be provided to the user, e.g., on the user's clothing and/or on or near the system 1000. The wind sensor can be used to estimate wind conditions at the installation site, which can be used to improve the detection of gas leaks. In other embodiments, the system 1000 can be coupled to or formed with a housing that defines a "gun"-like structure which can be aimed or pointed by the user in a particular direction.

As explained herein, a gas cloud 1202 emitted from a structure at the site can be imaged by pointing the system 1000 towards the gas cloud 1202 and capturing an image of the gas cloud 1202 when the cloud 1202 is within the FOV of the system 1000. Unlike other systems, the system 1000 can capture multispectral image data of a single scene over a range of IR wavelengths with a single snapshot, as explained in further detail herein. The single snapshot can be captured in a short timeframe, e.g., less than about 3 seconds, less than about 2 seconds, or less than about 1.5 seconds (for example, in about 1 second, in some embodiments). The single snapshot can be captured in greater than about 5 milliseconds, greater than about 0.2 seconds, or greater than about 0.5 seconds. The captured image data can be processed on board the system 1000 by a processing unit, as explained in further detail herein. For example, the processing unit can process the image data from the different optical channels and can compare the captured spectral information with a database of known chemicals to identify and/or characterize the gases that are included in the gas cloud 1202.

A communications module on board the system 1000 can transmit information relating to the identified gases or chemicals to any suitable external device. For example, the communications module can wirelessly communicate (e.g., by Bluetooth, WiFi, etc.) the information to a suitable mobile computing device, such as an electronic eyewear apparatus 1201, a tablet computing device 1212, a mobile smartphone, a laptop or notebook computer 1203, or any other suitable mobile computing device. In some embodiments, if a gas cloud is detected, the system 1000 can warn the user by way of sending a signal to the mobile device (e.g., tablet computing device 1212 or a mobile smartphone. The mobile device can emit an audible ring and/or can vibrate to notify the user of a potential gas leak. In the embodiment of FIG. 11A, the electronic eyewear apparatus 1201 can include a user interface comprising a display that the user 1275 can view in real-time as he visits the site. In some embodiments, the electronic eyewear apparatus 1201 comprises eyewear that includes a display. The electronics eyewear apparatus 1201 can be further configured to present images from this display to the wearer. The electronics eyewear apparatus 1201 may for example include projection optics that projects the image into the eye. The electronic eyewear apparatus 1201 may comprise heads up display optics the presents the image on the lens portion(s) of the eyewear so that the wearer can view the image and also see through the eyewear and peer at objects in the distance. Other configurations are possible. In some arrangements, the eyewear apparatus 1201 can comprise a Google Glass device, sold by Google, Inc., of Mountain View, Calif.

The processing unit can configure the processed image data such that the types of identified gases are displayed to the user 1275 on the display of the eyewear apparatus 1201. For example, in some embodiments, color-coded data may represent different types of gases or concentrations of a particular gas, and may be overlaid on a visible light image of the scene. For example, the color-coded data and image of the gas cloud can be seen by the user on the electronic eyewear apparatus 1201. In various embodiments, text data and statistics about the composition of the gas cloud 1202 may also be displayed to the user 1275. Thus, the user 1275 can walk the site and can view the different types of gases in the gas cloud 1202 substantially in real-time. Advantageously, such real-time display of the composition of the gas cloud 1202 can enable the user 1275 to quickly report urgent events, such as the leakage of a toxic gas or chemical. In some embodiments, detection of a toxic leak can trigger an alarm, which may cause emergency personnel to help evacuate the site and/or fix the leak.

In some embodiments, the processed image data can be transmitted from the system 1000 to the tablet computing device 1212, laptop computer 1203, and/or smartphone. The user 1275 can interact with the table computing device 1212 or laptop computer 1203 to conduct additional analysis of the imaged and processed gas cloud 1202. Furthermore, information about the gas cloud (including the processed data and/or the raw image data) may also be transmitted to a central server for centralized collection, processing, and analysis. In various arrangements, a global positioning system (GPS) module can also be installed on board the system 1000 and/or on the mobile computing device (such as a tablet computing device, smartphone, etc.). The GPS module can identify the coordinates of the user 1275 when a particular image is captured. The location data for the captured image data can be stored on the central server for further analysis.

Thus, the system 1000 shown in FIG. 11A can enable the user 1275 to image multiple locations of a particular site to be monitored, such as an oil well site. Advantageously, the optical components, the processing components, and the communications components of the system 1000 can be integrated within a relatively small housing that can be carried or worn by the user 1275. For example, in various embodiments, the system 1000 does not include complex mechanical components for movement, such as gimbals, actuators, motors, etc. Without such components, the size of the system 1000 can be reduced relative to other systems.

Unlike other systems, in which the system components are bulky or are assembled over a large form factor, the mobile system 1000 can be sized and shaped in such a manner so as to be easily moved and manipulated when the user 1275 moves about the site. Indeed, it can be very challenging to integrate the various system components in a small form-factor. Advantageously, the systems 1000 can be worn or carried by a human user. For example, the components of the system 1000 can be contained together in a data acquisition and processing module 1020, which may include a housing to support the system components. The components of the system 1000 (including the optical or imaging components, the focal plane array, the on-board processing electronics, and the communications components) may be packaged or assembled in the data acquisition and processing module 1020 and may occupy a volume less than about 300 cubic inches, less than about 200 cubic inches, or less than about 100 cubic inches. In various embodiments, the components of the system 1000 (including the optical or imaging components, the focal plane array, the on-board processing electronics, and the communications components) may be packaged or assembled in the data acquisition and processing module 1020 and may occupy a volume greater than about 2 cubic inches, or greater than about 16 cubic inches.

The data acquisition and processing module 1020 (with the system components mounted therein or thereon) may be sized and shaped to fit within a box-shaped boundary having dimensions X×Y×Z. For example, the data acquisition and processing module 1020, including the imaging optics, focal plane array, and on board processing electronics, may be included in a package that is sized and shaped to fit within the box-shaped boundary having dimensions X×Y×Z. This package may also contain a power supply, such as a battery and/or solar module. In some embodiments, the data acquisition and processing module 1020 (including the imaging optics, focal plane array, and on board processing electronics may) can be sized and shaped to fit within a box-shaped boundary smaller than 8 inches×6 inches×6 inches. In some embodiments, the data acquisition and processing module 1020 (including the imaging optics, focal plane array, and on board processing electronics may) can be sized and shaped to fit within a box-shaped boundary smaller than 7 inches×5 inches×5 inches, e.g., a box-shaped boundary small than 7 inches×3 inches×3 inches. In some embodiments, the data acquisition and processing module 1020 (including the imaging optics, focal plane array, and on board processing electronics may) can be sized and shaped to fit within a box-shaped boundary smaller than 6 inches×4 inches×4 inches. In some embodiments, the data acquisition and processing module 1020 (including the imaging optics, focal plane array, and on board processing electronics may) can be sized and shaped to fit within a box-shaped boundary smaller than 2 inches×2 inches×6 inches. In some embodiments, the data acquisition and processing module 1020 (including the imaging optics, focal plane array, and on board processing electronics may) can be sized and shaped to fit within a box-shaped boundary having dimensions larger than 4 inches×2 inches×2 inches. In some embodiments, the data acquisition and processing module 1020 (including the imaging optics, focal plane array, and on board processing electronics may) can be sized and shaped to fit within a box-shaped boundary having dimensions larger than 3 inches×3 inches×7 inches. In some embodiments, the data acquisition and processing module 1020 (including the imaging optics, focal plane array, and on board processing electronics may) can be sized and shaped to fit within a box-shaped boundary having dimensions larger than 2 inches×1 inches×1 inches. The data acquisition and processing module 1020 (including the imaging optics, focal plane array, and on board processing electronics may) can have dimensions less than 2 inches×2 inches×6 inches. The data acquisition and processing module 1020 (including the imaging optics, focal plane array, and on board processing electronics may) can have dimensions greater than 1 inches×1 inches×3 inches. The data acquisition and processing module 1020 (including the imaging optics, focal plane array, and on board processing electronics may) can have dimensions greater than 2 inches×2 inches×4 inches. said data acquisition and processing module has dimensions less than 6 inches×3 inches×3 inches. The data acquisition and processing module 1020 (including the imaging optics, focal plane array, and on board processing electronics may) can have dimensions less than 4 inches×3 inches×3 inches. The data acquisition and processing module 1020 (including the imaging optics, focal plane array, and on board processing electronics may) can have dimensions less than 3 inches×2 inches×2 inches. The data acquisition and processing module 1020 (including the imaging optics, focal plane array, and on board processing electronics may) can have dimensions greater than 2 inches×1 inches×1 inches. The data acquisition and processing module 1020 (including the imaging optics, focal plane array, and on board processing electronics may) can have dimensions greater than 1 inches×0.5 inch×0.5 inch. The data acquisition and processing module 1020 (including the imaging optics, focal plane array, and on board processing electronics may) can have a volume less than 30 cubic inches. The data acquisition and processing module 1020 (including the imaging optics, focal plane array, and on board processing electronics may) can have a volume less than 20 cubic inches. The data acquisition and processing module 1020 (including the imaging optics, focal plane array, and on board processing electronics may) can have a volume less than 15 cubic inches. The data acquisition and processing module 1020 (including the imaging optics, focal plane array, and on board processing electronics may) can have a volume less than 10 cubic inches. The data acquisition and processing module 1020 (including the imaging optics, focal plane array, and on board processing electronics may) can have a volume more than 1 cubic inches. The data acquisition and processing module 1020 (including the imaging optics, focal plane array, and on board processing electronics may) can have a volume more than 4 cubic inches. The data acquisition and processing module 1020 (including the imaging optics, focal plane array, and on board processing electronics may) can have a volume more 5 cubic inches. The data acquisition and processing module 1020 (including the imaging optics, focal plane array, and on board processing electronics may) can have a volume more 10 cubic inches. This package may also contain a power supply, including a battery and/or solar module, a communications module, or both and fit into the above-referenced dimensions. It should be appreciated that the dimensions disclosed herein may not correspond to the directions shown in FIG. 11A with respect to X, Y, and Z.

Moreover, the system 1000 can have a mass and weight sufficiently small so as to enable the user 1275 to easily carry or wear the data acquisition and processing module 1020 at the site. Thus, the embodiment shown in FIG. 11A can be sized and shaped and configured to have a mass that enables a human user to easily and effectively manipulate the system 1000.

Figure 11B:
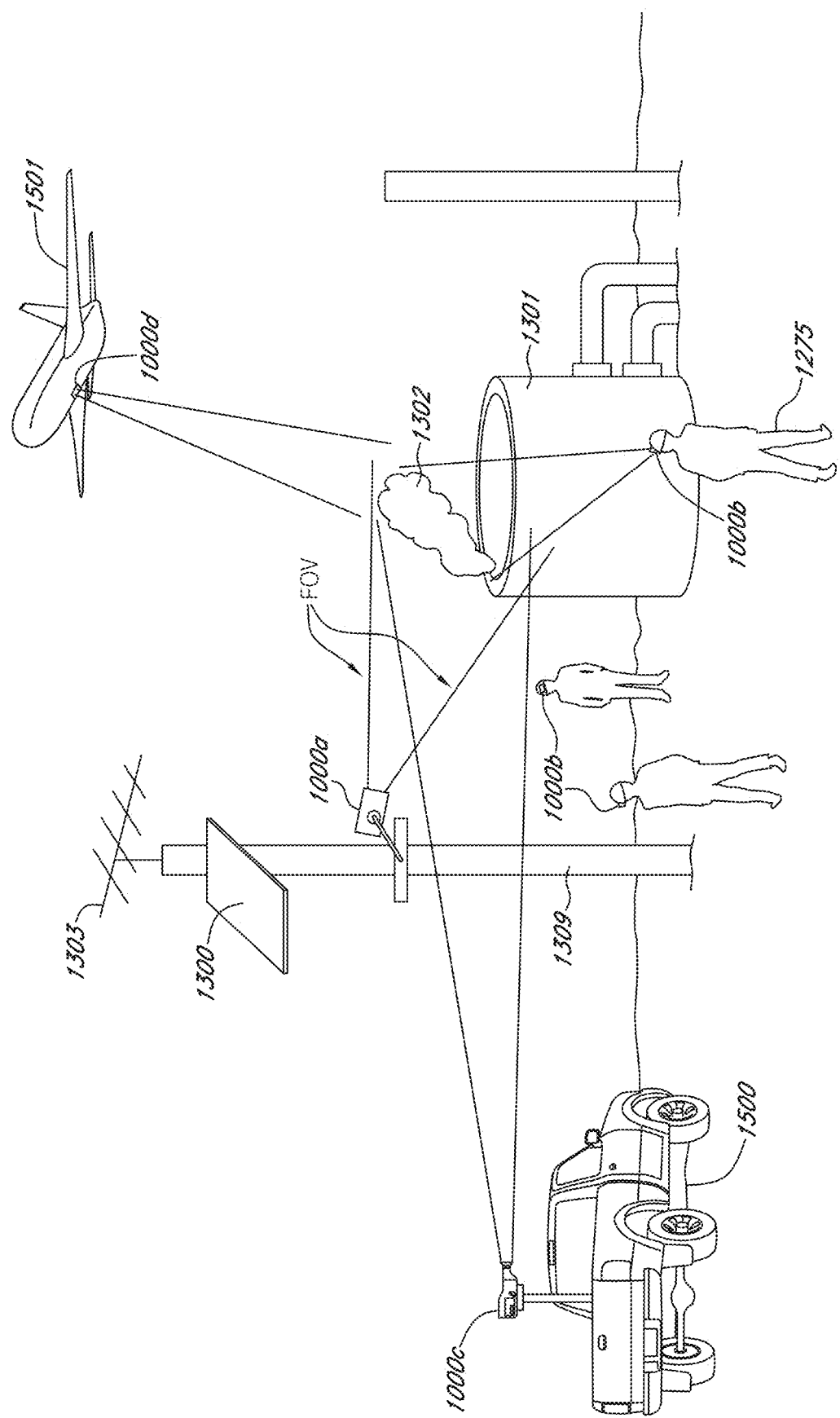
FIG. 11B is a schematic diagram illustrating an installation site that can be monitored by multiple infrared imaging systems.

FIG. 11B is a schematic diagram illustrating an installation site (e.g. an oil well site, etc.) that can be monitored by multiple infrared imaging systems 1000 (e.g., a DAISI system). For example, as shown in FIG. 11B, an imaging system 1000A can be mounted to a pole 1309 or other stationary structure at the site. An imaging system 1000B can be worn or carried by multiple users 1275, an imaging system 1000C can be mounted on a truck 1500, and/or an imaging system 1000D can be mounted on an aerial platform 1501, such as an unmanned aerial vehicle (UAV) or a piloted airplane. In some arrangements, the UAV can comprise an airplane, a helicopter (such as a quad helicopter), etc. The embodiments disclosed herein can utilize the image data captured by any combination of the systems 1000A-1000D at the installation site to image the entire installation site in an efficient manner. Indeed, each installation site can include any suitable number and type of system 1000A-1000D. For example, each installation site can include greater than two systems 1000A-1000D, greater than five systems 1000A-1000D, greater than ten systems 1000A-1000D, greater than twenty systems 1000A-1000D. Each installation site may include less than about 100 systems 1000A-1000D.

For example, the central server can track the real-time locations of each imaging system 1000A-1000D based on the GPS coordinates of the particular system or on predetermined knowledge about the system's stationary location. The distributed nature of the imaging systems 1000A-1000D can provide rich information to the central server about the types and locations of gas leaks or other problems throughout multiple installation sites. Although FIG. 11B illustrates a stationary system 1000A mounted to a fixture, a portable system 1000B to be worn or carried by a human, a truck-based system 1000C, and an aerial-based system 1000D, it should be appreciated that other types of systems may be suitable. For example, in some embodiments, a robotic vehicle or a walking robot can be used as a platform for the systems 1000 disclosed herein. In various embodiments, a floating platform (such as a boat) can be used as a platform for the systems 1000 disclosed herein. It should also be appreciated that the systems disclosed herein can utilize any combination of the platforms (e.g., stationary fixtures such as a pole, human user(s), truck(s) or other vehicle, aerial platform(s), floating platform(s), robotic platform(s), etc.) to support the systems 1000.

The systems 1000 shown in FIG. 11B can comprise a mobile DAISI system, similar to that illustrated in FIG. 11A. In other embodiments, the systems 1000 can comprise a larger DAISI system configured for use on a relatively long-term basis. For example, the stationary imaging system 1000A shown in FIG. 11B can be installed on a pole 1309 or other suitable structure for monitoring a storage tank 1301. A solar panel 1300 can be provided at or near the system 1000 to help provide power to the system 1000. An antenna 1303 can electrically couple to the system and can provide wireless communication between the system 1000 and any other external entity, such as a central server, for storing and/or processing the data captured by the system 1000.

The stationary infrared imaging system 1000A can be programmed to continuously or periodically monitor the site. If a gas cloud 1302 escapes from the storage tank 1301, such as by leaking from a broken valve, then the system 1000A can capture a multispectral, snapshot image or series of images (e.g., a video stream) of the gas cloud 1302. As with the embodiment of FIG. 11A, the imaging system 1000A can include imaging, processing, and communications components on board the system 1000A to identify and characterize the types of gases in the cloud 1302 and to transmit the processed data to the central server, e.g., by way of the antenna 1303.

The imaging systems 1000B worn or carried by the multiple users 1275 can advantageously capture and process multispectral image data of the portions of the installation site that each user 1275 visits. It should be appreciated that the different users 1275 may work in or travel through different portions of the installation site (and also to a number of installation sites) over a period of time. When activated, the imaging systems 1000B worn or carried by the users 1275 can continuously or periodically capture multispectral image data of the different locations at the installation site(s) to which the user 1275 travels. As explained herein, the system 1000B can transmit the image data and the location at which the image was captured to the central server. If the system 1000B or the central server detects a problem (such as a gas leak), then the central server can associate that leak with a particular location and time.

Furthermore, because the central server can receive image data and location data from multiple users at different locations and viewing from different perspectives, the central server can create an organization-wide mapping of gas leaks that include, e.g., the locations of gas leaks in any of multiple installation sites, the type and concentrations and expanse or extent of each gas leaked, the particular user 1275 that captured the image data, and the time at which the image was taken. Thus, each user 1275 that carries or wears a portable imaging system 1000B can contribute information to the central server that, when aggregated by the central server, provides rich details on the status of any gas leaks at any installation sites across the organization.

The truck-mounted imaging system 1000C can be mounted to a truck or other type of vehicle (such as a car, van, all-terrain vehicle, etc.). As shown in FIG. 11B, the imaging system 1000C can be connected to an end of an extendable pole or extension member mounted to the truck 1500. The system 1000C can be raised and lowered by a control system to enable the system 1000C to image a wide area of the installation site. In some embodiments, actuators can be provided to change the angular orientation of the system 1000C, e.g., its pitch and yaw. A vibration isolation or reduction mechanism can also be provided to reduce vibrations, which may disturb the imaging process. The system 1000C can be battery powered and/or can be powered by the truck; in some embodiments, a generator can be used to supply power to the system 1000C. A user can drive the truck 1500 throughout the installation site to image various portions of the site to detect leaks. In addition, the user can drive the truck 1500 to other installation sites to detect gas leaks. As explained herein, the location of the truck 1500 can be communicated to the central server and the location of the truck 1500 can be associated with each captured image. The truck 1500 may include GPS electronics to assist in tracking the location of the truck 1500 and/or system 1000C over time as the user drives from place to place. Similarly, the aerial platform 1501 (such as an unmanned aerial vehicle, or UAV) can support the imaging system 1000D. The aerial platform 1501 can be piloted (either remotely or non-remotely) to numerous installation sites to capture multispectral image data to detect gas clouds.

Thus, the systems 1000A-1000D can provide extensive data regarding the existence of leaks at numerous installations across an organization. Monitoring numerous cameras simultaneously or concurrently across an organization, site, region, or the entire country can be enabled at least in part by providing wireless (or wired) communication between the systems 1000A-1000D and one or more central servers. Advantageously, the collection of image data from multiple sources and multiple platforms can enable the organization to create a real-time mapping of potential gas leaks, the types and amounts of gases being leaks, the locations of the leaks, and the time the image data of the leak was captured. In some arrangements, the aggregation of data about a site can improve the safety of installation sites. For example, if a gas leak is detected at a particular installation, the embodiments disclosed herein can alert the appropriate personnel, who can begin safety and/or evacuation procedures. Moreover, the aggregation of data across an organization (such as an oil service company) can provide site-wide, region-wide, and/or company-wide metrics for performance. For example, a given facility can monitor its total emissions over time and use the resulting data to help determine the facility's overall performance. A given region (such as a metropolitan area, a state, etc.) can monitor trends in emissions over time, providing a value on which to base decisions. Likewise, a company can look at the emissions performance at all of its facilities and can make decisions about whether some facilities should make new investments to improve performance, and/or whether the entire company should make various improvements. The mobile systems 1000 disclosed herein can thus provide a ubiquitous monitoring system for decision making. In addition, the systems 1000 disclosed herein can be used in a feedback control process to improve various manufacturing procedures based on the gases detected by the system(s) 1000. Accordingly, a control module may be provided to adjust the manufacturing procedure and/or parameters according to the gases measured by the system 1000.

The embodiments of the mobile infrared imaging system 1000 disclosed herein provide various advantages over other systems. As explained above, aggregation of data about a site and its potential gas leaks can provide an organization- or system-wide mapping of potential problems. Furthermore, automatic detection of gas leaks (and identification of the gases in the gas cloud) can simplify operation of the system 1000 and can reduce the risk of user errors in attempting to detect or identify gas clouds manually. Moreover, the small size of the systems 1000 disclosed herein are more easily carried or worn by the user than other systems. In addition, the systems 1000 disclosed herein can overlay the identified gas clouds on a visible image of the scene and can color code the gas cloud according to, e.g., type of gas, concentration, etc.

Figure 12:
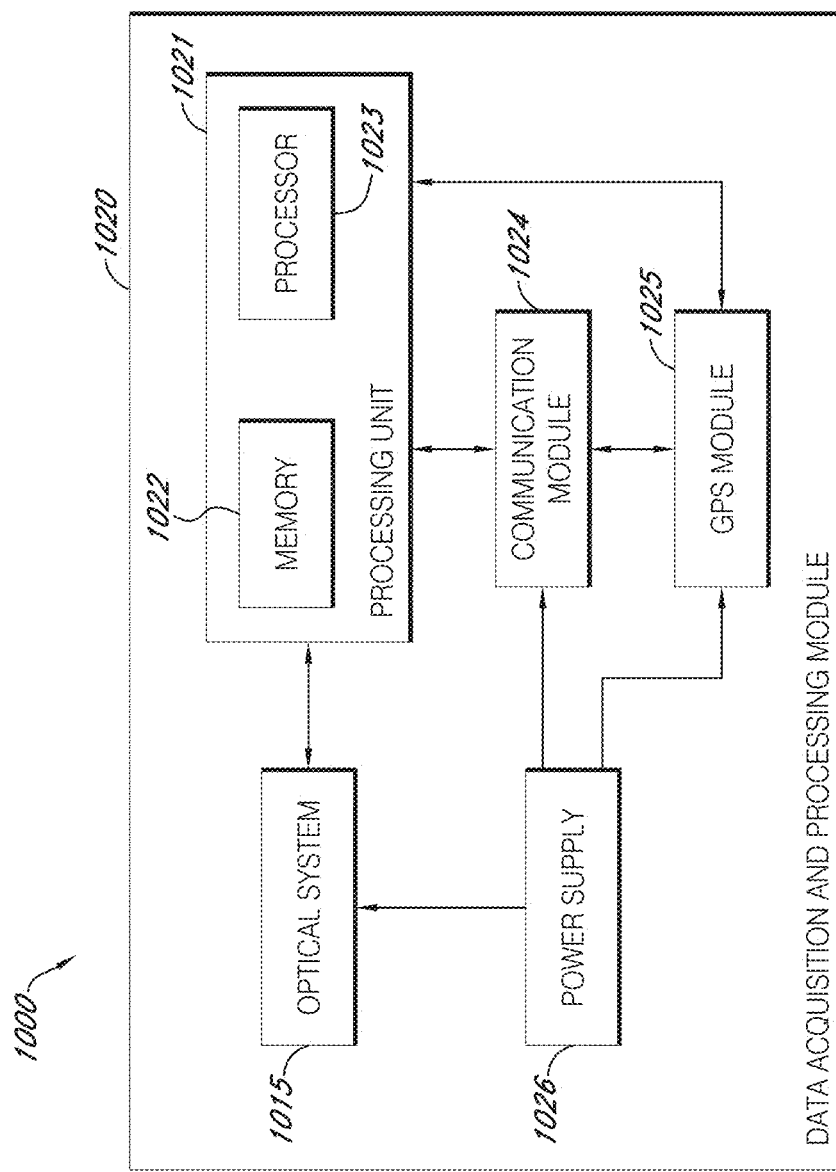
FIG. 12 is a schematic system block diagram showing a mobile infrared imaging system, according to one embodiment.

FIG. 12 is a schematic system block diagram showing a mobile infrared imaging system 1000 (e.g., a mobile DAISI system), according to one embodiment. The imaging system 1000 can include a data acquisition and processing module 1020 configured to be worn or carried by a person. The data acquisition and processing module 1020 can include, contain, or house an optical system 1015, a processing unit 1021, a power supply 1026, a communication module 1025, and GPS module 1025. In other embodiments, the data acquisition and processing module 1020 can be configured to be mounted to a structure at the site to be monitored, such as a post. The power unit 1026 can be provided on board the system 1000. The power unit 1026 can be configured to provide power to the various system components, such as the optical system 1015, the processing unit 1021, the communication module 1024, and/or the GPS module 1025. In some embodiments, the power unit 1026 can comprise one or more batteries (which may be rechargeable) to power the system components. In some embodiments, the power unit 1026 can include a solar power system including one or more solar panels for powering the system by sunlight. In some embodiments, the power unit 1026 can include various power electronics circuits for converting AC power supplied by standard power transmission lines to DC power for powering the system components. Other types of power supply may be suitable for the power unit 1026.

The system 1000 can include an optical system 1015 configured to capture multispectral image data in a single snapshot, as explained herein. The optical system 1015 can correspond to any suitable type of DAISI system, such as, but not limited to, the optical systems and apparatus illustrated in FIGS. 1-10C above and/or in the optical systems 1015 illustrated in FIGS. 13A-13B below. For example, the optical system 1015 can include an optical focal plane array (FPA) unit and components that define at least two optical channels that are spatially and spectrally different from one another. The two optical channels can be positioned to transfer IR radiation incident on the optical system towards the optical FPA. The multiple channels can be used to multiplex different spectral images of the same scene and to image the different spectral images on the FPA unit.

The processing unit 1021 can also be provided on board the data acquisition and processing module 1020. The processing unit 1021 can include a processor 1023 and a memory 1022. The processor 1023 can be in operable cooperation with the memory 1022, which can contain a computer-readable code that, when loaded onto the processor 1023, enables the processor 1023 to acquire multispectral optical data representing a target species of gas or chemical from IR radiation received at the optical FPA unit of the optical system 1015. The memory 1022 can be any suitable type of memory (such as a non-transitory computer-readable medium) that stores data captured by the optical system 1015 and/or processed by the processing unit 1021. The memory 1022 can also store the software that is executed on the processor 1023. The processor 1023 can be configured to execute software instructions that process the multispectral image data captured by the optical system 1015. For example, the processor 1023 can analyze the different images detected by the FPA and can compare the captured data with known signatures of various types of gases or chemicals. Based on the analysis of the captured image data, the processor can be programmed to determine the types and concentrations of gases in a gas cloud. Further, as explained herein, the processor 1023 can analyze calibration data provided by the optical system 1015 to improve the accuracy of the measurements.

Advantageously, the processor 1023 can comprise one or more field-programmable gate arrays (FPGA) configured to execute methods used in the analysis of the images captured by the optical system 1015. For example, the FPGA can include logic gates and read access memory (RAM) blocks that are designed to quickly implement the computations used to detect the types of gases in a gas cloud. The small size/weight, and high performance characteristics of the FPGA can enable on board computation and analysis within the data acquisition and detection unit 1020 worn or carried by the user. The use of FPGA (or similar electronics) on board the system 1000 can reduce costs associated with using an off-site central server or larger computing device to conduct the image analysis computations. In addition, enabling computation with one or more FPGA devices on board the wearable system can also prevent or reduce communication bottlenecks associated with wirelessly transmitting large amounts of raw data from the system 1000 to a remote server or computer, which can be used in some embodiments.

The communication module 1024 can be configured to communicate with at least one device physically separate from the data acquisition and processing module 1020. For example, the communication module 1024 can include a wireless communication module configured to wirelessly communicate with the at least one separate device. The wireless communication module can be configured to provide wireless communication over wireless networks (e.g., WiFi internet networks, Bluetooth networks, etc.) and/or over telecommunications networks (e.g., 3G networks, 4G networks, etc.).

In some embodiments, for example, the wireless communication module can provide data communication between the data acquisition and processing module 1020 and a mobile device such as an electronic eyewear apparatus, a tablet computing device, a mobile smartphone, a laptop or notebook computer, or any other suitable mobile computing device. As explained herein, the mobile device can include a display on which the processed image data can be displayed to the user. For example, the types (and/or concentrations) of gases in a gas cloud can be illustrated on the display, e.g., by color coding or other suitable illustration scheme. The processed data can overlie a visible image of the scene in some arrangements. In some embodiments, the wireless communication module can provide data communication between the system 1000 and an external device remote from the system 1000, such as a central server. For example, the processed image data and/or the raw image data may be transmitted over a telecommunications network to the central server for storage and/or further analysis. In some embodiments, the processed or raw image data can be uploaded to the mobile device (e.g., notebook computer, smartphone, tablet computing device, etc.), which can in turn communicate the image data to the central server.

The GPS module 1025 can be configured to determine the location of the data acquisition and processing module 1020 at a particular time. The processing unit 1021 can store the location data and can associate the location data with a particular image captured by the optical system 1015 in some arrangements. The location data associated with the captured images can be transmitted by the communication module 1024 (or by an external device) to a central server in some arrangements.

The optical system 1015, the processing unit 1021, the power supply 1026, the communication module 1024, and/or the GPS module 1025 may be contained or housed in the data acquisition and processing module 1020, which can be carried or worn by the user. The components of the system 1000 (including the optical components, the processing components, and the communications components) may be packaged or assembled in the data acquisition and processing module 1020 and may occupy a volume less than about 300 cubic inches, less than about 200 cubic inches, or less than about 100 cubic inches. In various embodiments, the components of the system 1000 (including the optical components, the processing components, and the communications components) may be packaged or assembled in the data acquisition and processing module 1020 and may occupy a volume greater than about 2 cubic inches, or greater than about 16 cubic inches. A power supply, including a battery and/or solar module may also be included among the components packaged or assembled in the data acquisition and processing module 1020 and fit into the above-referenced volumetric dimensions.

The data acquisition and processing module 1020 (with the system components mounted therein or thereon, including the imaging optics, focal plane array, and on board processing electronics may) may be sized and shaped to fit within a box-shaped boundary having dimensions X×Y×Z. For example, in some embodiments, the data acquisition and processing module 1020 (including the imaging optics, focal plane array, and on board processing electronics may) can be sized and shaped to fit within a box-shaped boundary smaller than 8 inches×6 inches×6 inches. In some embodiments, the data acquisition and processing module 1020 (including the imaging optics, focal plane array, and on board processing electronics may) can be sized and shaped to fit within a box-shaped boundary smaller than 7 inches×5 inches×5 inches. In some embodiments, the data acquisition and processing module 1020 (including the imaging optics, focal plane array, and on board processing electronics may) can be sized and shaped to fit within a box-shaped boundary smaller than 6 inches×4 inches×4 inches. In some embodiments, the data acquisition and processing module 1020 (including the imaging optics, focal plane array, and on board processing electronics may) can be sized and shaped to fit within a box-shaped boundary having dimensions larger than 4 inches by 2 inches×2 inches. In some embodiments, the data acquisition and processing module 1020 (including the imaging optics, focal plane array, and on board processing electronics may) can be sized and shaped to fit within a box-shaped boundary having dimensions larger than 2 inches by 1 inches×1 inches. A power supply, including a battery and/or solar module, a communications module, or both may be included in the data acquisition and processing module 1020 and fit into the above-referenced dimensions. It should be appreciated that the dimensions disclosed herein may not correspond to the directions shown in FIG. 11A with respect to X, Y, and Z. Moreover, the system 1000 can have a mass and weight sufficiently small so as to enable the user 1275 to easily carry or wear the data acquisition and processing module 1020 at the site.

FIG. 13A is a schematic system diagram of an optical system 1015 configured to be used in the mobile infrared imaging systems 1000 disclosed herein, according to various embodiments. As explained herein, the optical system 1015 shown in FIG. 13A can be provided in the data acquisition and processing module 1020 to be worn or carried by the user. The optical system 1015 can be configured to capture multispectral image data of an object 1007, such as a gas cloud, chemical spill, etc. The components of the optical system 1015 shown in FIG. 13A may be similar to or the same as the components of the optical systems and devices explained herein with respect to FIGS. 1-10C. The optical system 1015 can include a focal plane array (FPA) unit 1008 configured to record infrared image data captured by the system 1000. As shown in FIG. 13A, the FPA unit 1008 may advantageously be uncooled, e.g., devoid of a cooling system.

The optical system 1015 can include a front window 1006 through which light from the object 1007 passes. A first moveable blackbody source 1003 and a second moveable blackbody source 1004 can be provided to enable calibration of the optical system 1015. The moveable sources 1003, 1004 can be moved in front of the field of view such that the optics image these sources for calibration. For example, the first and second blackbody sources 1003, 1004 can be maintained at different known temperatures in a stable manner. For example, a heater and a temperature sensor can be attached to each blackbody source 1003, 1004 to provide feedback to create a stable and known temperature difference (e.g., at least 50 mK in some arrangements) between different spatial regions of the sources.

In addition, the optical system 1000 can include a dynamic calibration apparatus to dynamically calibrate the system 1000. As shown in FIG. 13A, one or more calibration sources 1009, 1010 can be provided. The calibration sources 1009, 1010 can comprise a thermal electrically controlled (TEC) material with a temperature sensor attached thereto. The calibration sources 1009, 1010 can be coated with a spectrally measured coating or paint. Light from the calibration sources 1009, 1010 can be reflected from one or more mirrors 1005 and directed through the lens array 1002 (described below) to be imaged on a portion of the FPA unit 1008 to assist in dynamically calibrating the system 1000 (e.g., while imaging of the target gas cloud is simultaneously being imaged).

The optical system 1000 can include a lens array 1002 to focus the incoming light onto the FPA unit 1008. As shown in FIG. 13A, each lens of the lens array 1002 can at least partially define or be included in an optical channel to be imaged by the FPA unit 1008. To improve the mobility and portability of the mobile imaging system 1000, the lens array 1002 can comprise an integrated unit formed from or assembled into a single unitary body. Such an integrated lens array 1002 can reduce the size of the imaging system 1015, and therefore, the size of the system 1000, to at least partially enable the system 1000 to be worn or carried by the user. The lens array 1002 can be monolithically formed in any suitable manner. For example, in various embodiments, the lens array 1002 can be formed by a diamond milling tool. In some embodiments, the lens array 1002 can comprise a monolithic piece of transparent material which has separate regions shaped into curved refractive surfaces for creating separate lenses. In some embodiments, the lenses can be inserted into an array of openings formed in a plate or substrate to create the lens array 1002.

The optical system 1000 can also include an array of infrared (IR) filters 1001 configured to filter wavelengths of infrared light in an appropriate manner. Examples of IR filters and filtering techniques are disclosed herein, for example, with respect to FIGS. 5A-6D. As shown in FIG. 13A, the IR filters 1001 can be disposed between the lens array 1002 and the FPA unit 1008. The IR filters 1001 can at least partially define the multiple optical channels to be imaged by the FPA unit 1008. In some embodiments, the IR filters 1001 can be positioned between the lens array 1002 and the first and second moveable blackbody sources 1009, 1010.

FIG. 13B is a schematic system diagram of an optical system 1015 configured to be used in the mobile infrared imaging systems 1000 disclosed herein, according to various embodiments. As explained herein, the optical system 1015 shown in FIG. 13B can be provided in the data acquisition and processing module 1020 to be worn or carried by the user. The components of the optical system 1015 shown in FIG. 13B may be similar to or the same as the components of the optical systems and devices explained herein with respect to FIGS. 1-10C and 13A.

The optical system 1015 of FIG. 13B can include an FPA unit 1408 configured to image an object 1409, such as a gas cloud or chemical leak. As with the embodiment illustrated in FIG. 13A, the system 1015 of FIG. 13B can include a front window 1406 through which light from the object 1409 passes, first and second moveable blackbody sources 1403, 1404, an IR filter array 1401, and a lens array 1402. As with the embodiment of FIG. 13A, the lens array 1402 can comprise a unitary or monolithic body. In the embodiment of FIG. 13B, the lens array 1402 may be disposed between the filter array 1401 and the FPA unit 1408. In other arrangements, the filter array 1401 may be disposed between the lens array 1402 and the FPA unit 1408.

The optical system 1015 of FIG. 13B can include a cooling unit 1430 configured to cool the FPA unit 1408. The cooling unit 1430 can comprise a cooling finger configured to cryogenically cool the FPA array 1408 in various arrangements. As shown in FIG. 13B, the filter array 1401, the lens array 1402, and the FPA unit 1408 can be disposed in a cooled region 1440. The blackbody sources 1403, 1404 and front window 1406 can be disposed in an uncooled region 1450. Disposing the blackbody sources 1403, 1404 at uncooled temperatures and the filter array 1401, lens array 1402, and FPA unit 1408 at cooled temperatures can assist in the periodic calibration of the system 1000.

Figure 14A:
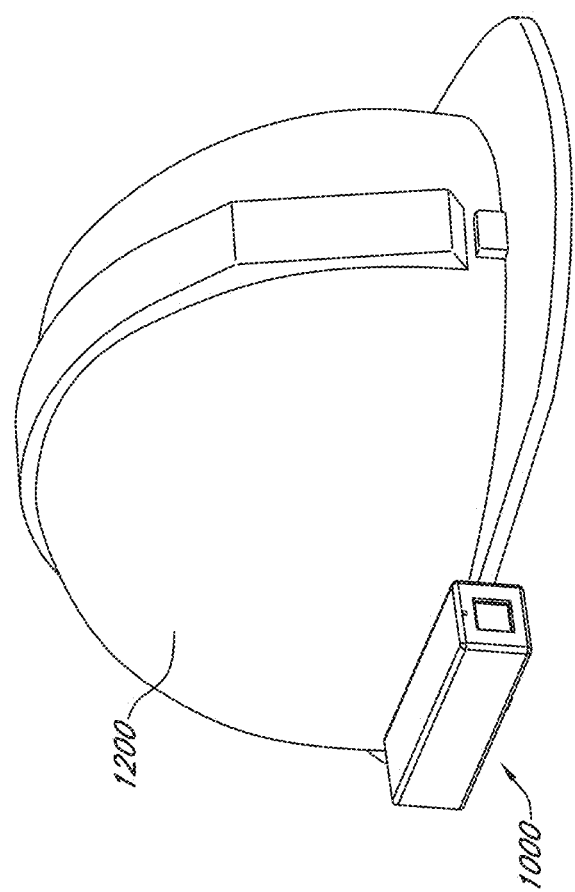
FIG. 14A is a schematic perspective view of a mobile infrared imaging system mounted to a helmet, according to various embodiments.
Figure 14B:
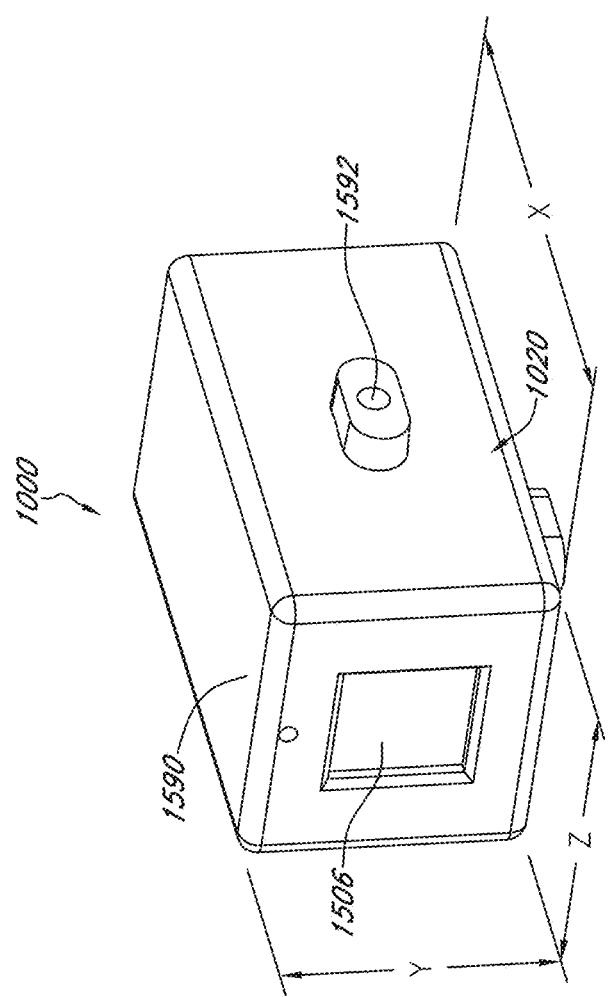
FIG. 14B is an enlarged schematic perspective view of the mobile infrared imaging system shown in FIG. 14A.

FIG. 14A is a schematic perspective view of a mobile infrared imaging system 1000 (e.g., mobile DAISI system) mounted to a helmet 1200, according to various embodiments. FIG. 14B is an enlarged schematic perspective view of the mobile infrared imaging system 1000 shown in FIG. 14A. The helmet 1200 can comprise a portion of a user's personal protective equipment and can also advantageously be used as a platform for the imaging system 1000. As explained above, the helmet 1200 can be worn by a user as the user visits a particular installation site to be monitored, such as an oil well site, a refinery, etc. The system 1000 can be activated to continuously monitor and analyze the sites that the user visits. The system 1000 can thereby continuously and actively search for gas leaks wherever the user visits and can initiate an alarm or other notification if a leak is detected.

In the embodiment illustrated in FIG. 14B, the imaging system 1000 can comprise a housing 1590, within or to which a data acquisition and processing module 1020 (see, e.g., FIG. 12 and associated description) is mounted or coupled. A support 1592 can be coupled to or formed with the housing 1590 and can be configured to attach to the helmet 1200 or to any other suitable platform. For example, in some embodiments, the support 1592 can include one or more mounting holes for attaching to the helmet 1200 by way of, e.g., screws, bolts, or other fasteners. In addition, as shown in FIG. 14B, a front window 1506 can be provided at a front end of the housing 1590. The front window 1506 can be transparent to IR radiation and can at least partially define the aperture of the system 1000. In some embodiments, the window 1506 comprises germanium. A diamond like coating (DLC) or other coating or layer can be disposed over the window 1506 to provide a durable surface.

As explained herein, the system 1000 can be configured to be worn or carried by a human user. Accordingly, the data acquisition and processing module 1020 can be suitably dimensioned such that a user can easily wear or carry the system 1000. For example, the data acquisition and processing module 1020 can be defined at least in part by dimensions X×Y×Z, as shown in FIGS. 14A and 14B.

Unlike other systems, in which the system components are bulky or are assembled over a large form factor, the mobile system 1000 can be sized and shaped in such a manner so as to be easily moved and manipulated when the user moves about the site. Indeed, it can be very challenging to integrate the various system components in a small form-factor. Advantageously, the systems 1000 disclosed herein can be worn or carried by a human user. For example, the components of the system 1000 can be contained together in the data acquisition and processing module 1020, which may include the housing 1590 to support the system components. The components of the system 1000 (including the optical or imaging components, the focal plane array, the on-board processing electronics, and the communications components) may be packaged or assembled in the data acquisition and processing module 1020 and may occupy a volume less than about 300 cubic inches, less than about 200 cubic inches, or less than about 100 cubic inches. In various embodiments, the components of the system 1000 (including the optical or imaging components, the focal plane array, the on-board processing electronics, and the communications components) may be packaged or assembled in the data acquisition and processing module 1020 and may occupy a volume greater than about 2 cubic inches, or greater than about 16 cubic inches. In some embodiments, the components of the system 1000 (including the optical or imaging components, the focal plane array, the on-board processing electronics, and the communications components) may be packaged or assembled in the data acquisition and processing module 1020 and may occupy a volume in a range of about 4 cubic inches to about 15 cubic inches. In some embodiments, the components of the system 1000 (including the optical or imaging components, the focal plane array, the on-board processing electronics, and the communications components) may be packaged or assembled in the data acquisition and processing module 1020 and may occupy a volume in a range of about 5 cubic inches to about 12 cubic inches. In some embodiments, the components of the system 1000 (including the optical or imaging components, the focal plane array, the on-board processing electronics, and the communications components) may be packaged or assembled in the data acquisition and processing module 1020 and may occupy a volume in a range of about 4 cubic inches to about 6.5 cubic inches, e.g., about 5.63 cubic inches in one embodiment. In some embodiments, the components of the system 1000 (including the optical or imaging components, the focal plane array, the on-board processing electronics, and the communications components) may be packaged or assembled in the data acquisition and processing module 1020 and may occupy a volume in a range of about 9 cubic inches to about 13 cubic inches, e.g., about 11.25 cubic inches in one embodiment. In some embodiments, the components of the system 1000 (including the optical or imaging components, the focal plane array, the on-board processing electronics, and the communications components) may be packaged or assembled in the data acquisition and processing module 1020 and may occupy a volume in a range of about 6 cubic inches to about 10 cubic inches.

The data acquisition and processing module 1020 (with the system components mounted therein or thereon) may be sized and shaped to fit within a box-shaped boundary having dimensions X×Y×Z. For example, the data acquisition and processing module 1020, including the imaging optics, focal plane array, and on board processing electronics may be included in a package that is sized and shaped to fit within the box-shaped boundary having dimensions X×Y×Z. This package may also contain a power supply, such as a battery and/or solar module. In some embodiments, the data acquisition and processing module 1020 (including the imaging optics, focal plane array, and on board processing electronics may) can be sized and shaped to fit within a box-shaped boundary smaller than 8 inches×6 inches×6 inches. In some embodiments, the data acquisition and processing module 1020 (including the imaging optics, focal plane array, and on board processing electronics may) can be sized and shaped to fit within a box-shaped boundary smaller than 7 inches×5 inches×5 inches. In some embodiments, the data acquisition and processing module 1020 (including the imaging optics, focal plane array, and on board processing electronics may) can be sized and shaped to fit within a box-shaped boundary smaller than 6 inches×4 inches×4 inches. In some embodiments, the data acquisition and processing module 1020 (including the imaging optics, focal plane array, and on board processing electronics may) can be sized and shaped to fit within a box-shaped boundary smaller than 6 inches×2 inches×2 inches. In some embodiments, the data acquisition and processing module 1020 (including the imaging optics, focal plane array, and on board processing electronics may) can be sized and shaped to fit within a box-shaped boundary having dimensions larger than 4 inches×2 inches×2 inches. In some embodiments, the data acquisition and processing module 1020 (including the imaging optics, focal plane array, and on board processing electronics may) can be sized and shaped to fit within a box-shaped boundary having dimensions larger than 2 inches×1 inches×1 inches. The data acquisition and processing module 1020 (including the imaging optics, focal plane array, and on board processing electronics may) can have dimensions less than 3 inches×2 inches×2 inches. The data acquisition and processing module 1020 (including the imaging optics, focal plane array, and on board processing electronics may) can have dimensions greater than 1 inches×0.5 inch×0.5 inch. The data acquisition and processing module 1020 (including the imaging optics, focal plane array, and on board processing electronics may) can have a volume less than 30 cubic inches. The data acquisition and processing module 1020 (including the imaging optics, focal plane array, and on board processing electronics may) can have a volume less than 20 cubic inches. The data acquisition and processing module 1020 (including the imaging optics, focal plane array, and on board processing electronics may) can have a volume less than 15 cubic inches. The data acquisition and processing module 1020 (including the imaging optics, focal plane array, and on board processing electronics may) can have a volume less than 10 cubic inches. The data acquisition and processing module 1020 (including the imaging optics, focal plane array, and on board processing electronics may) can have a volume more than 1 cubic inches. The data acquisition and processing module 1020 (including the imaging optics, focal plane array, and on board processing electronics may) can have a volume more than 4 cubic inches. The data acquisition and processing module 1020 (including the imaging optics, focal plane array, and on board processing electronics may) can have a volume more 5 cubic inches. The data acquisition and processing module 1020 (including the imaging optics, focal plane array, and on board processing electronics may) can have a volume more 10 cubic inches. This package may also contain a power supply, including a battery and/or solar module, a communications module, or both and fit into the above-referenced dimensions. It should be appreciated that the dimensions disclosed herein may not correspond to the directions shown in FIG. 11A with respect to X, Y, and Z. This package may also contain a power supply, including a battery and/or solar module, a communications module, or both and fit into the above-referenced dimensions. It should be appreciated that the dimensions disclosed herein may not correspond to the directions shown in FIG. 11A with respect to X, Y, and Z.

In some embodiments, the dimension X shown in FIG. 14B can be in a range of about 2 inches to about 7 inches, or more particularly, in a range of about 2 inches to about 4 inches, e.g., about 2.5 inches in one embodiment. In some embodiments, the dimension X shown in FIG. 14B can be in a range of about 4 inches to about 6 inches, e.g., about 5 inches in one embodiment. In some embodiments, the dimension Y shown in FIG. 14B can be in a range of about 1 inch to about 5 inches, or more particularly, in a range of about 1 inch to about 3 inches, e.g., about 1.5 inches in one embodiment. In some embodiments, the dimension Z shown in FIG. 14B can be in a range of about 1 inch to about 5 inches, or more particularly, in a range of about 1 inch to about 3 inches, e.g., about 1.5 inches in one embodiment.

Moreover, the system 1000 can have a mass and weight sufficiently small so as to enable the user 1275 to easily carry or wear the data acquisition and processing module 1020 at the site. For example, the system 1000 can have a weight in a range of about 0.5 pounds to 5 pounds, or more particularly, in a range of about 0.5 pounds to 2 pounds, or more particularly in a range of about 0.25 pounds to about 2 pounds, or more particularly, in a range of about 0.25 pounds to about 1.5 pounds. In one embodiment, for example, the system 1000 can weight about 1 pound. In another embodiment, for example, the system 1000 can weigh about 0.5 pounds. Thus, the embodiment shown in FIG. 11A can be sized and shaped and configured to have a mass that enables a human user to easily and effectively manipulate the system 1000.

Figure 14C:
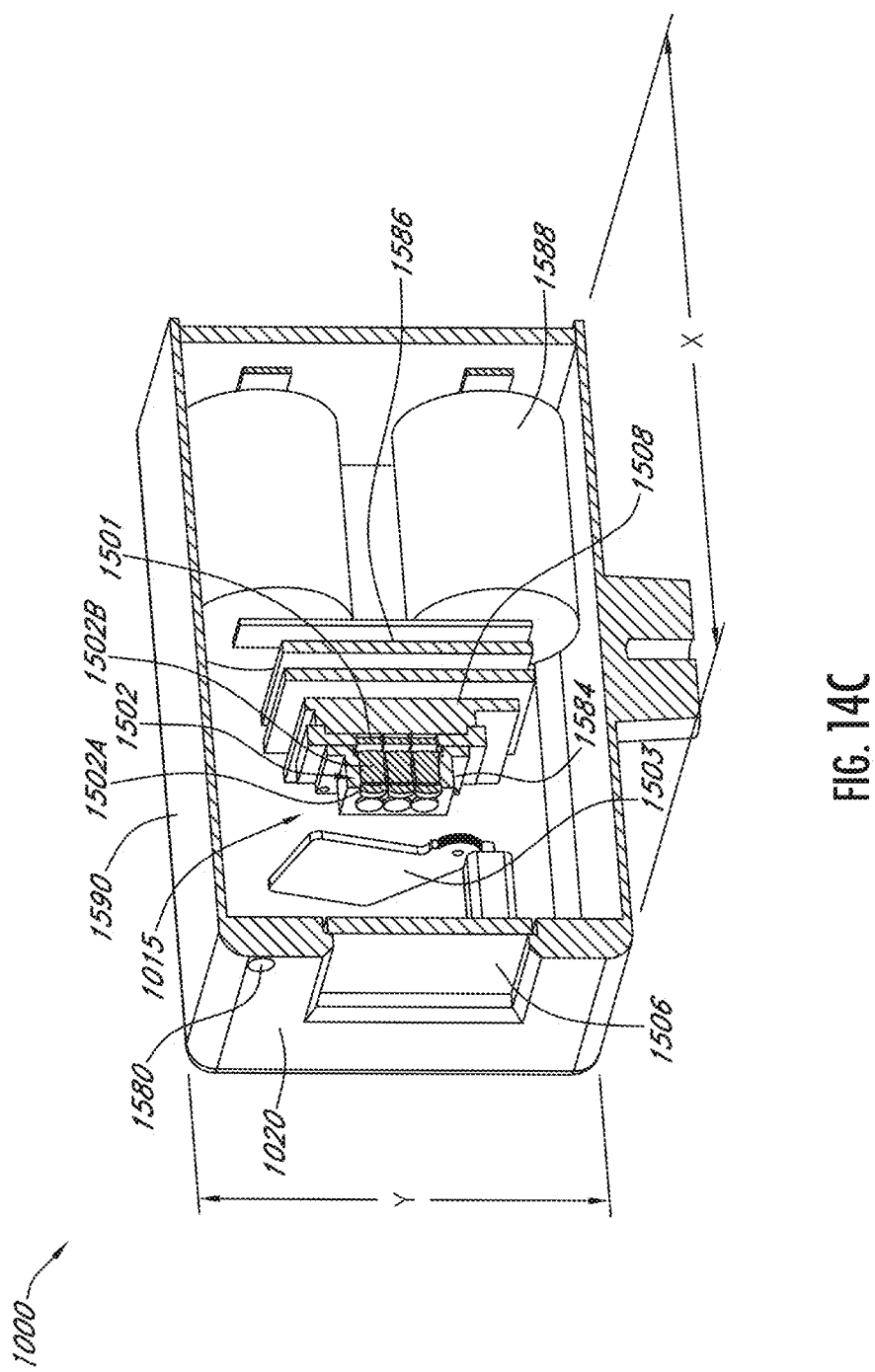
FIG. 14C is a perspective cross-sectional view of the mobile infrared imaging system shown in FIGS. 14A-14B.

FIG. 14C is a perspective cross-sectional view of the mobile infrared imaging system 1000 shown in FIGS. 14A-14B. The mobile infrared imaging system 1000 can include one or more movable shutters 1503 (e.g., two shutters) rear of the window 1506 and a lens assembly 1502 rear of the shutter(s) 1503. A filter array 1501 can be disposed rear (or forward) of the second lens array 1502B, and an optical focal plane array (FPA) unit 1508 can be disposed rear of the filter array 1501. The optical FPA unit 1508 can be mechanically and electrically coupled with one or more substrates 1586, which may comprise printed circuit board or PCB substrates. In various embodiments, the FPA unit 1508 comprises a single FPA or detector array. Additionally, as explained herein, the lens assembly 1502, filter array 1501, and optical FPA unit can at least partially define one or more optical channels that are spatially and spectrally different. A number of the optical channels can be at least 4, at least 5, at least 8, at least 9, at least 12, at least 13, or at least 20. In some embodiments, a number of the optical channels is between 4 and 50.

One or more batteries 1588 can supply power to the system 1000 by way of the substrate(s) 1586. In addition, a visible light imaging sensor 1580 can be disposed in the housing 1590 and can be configured to provide a visible light image of the scene being captured by the system 1000. The processed IR image data can be overlaid upon the visible light image. In various embodiments the visible light imaging sensor 1580 can be used for reduction of scene-motion-induced detection errors, for example, to detect a moving object that enters the field of view (such as an animal or person) and would interfere with the data being collected.

As explained herein, the movable shutter(s) 1503 can be configured to provide spectral-radiometric calibration for the system 1000. The shutter(s) 1503 can be configured to move in and out of the field of view of the lens assembly 1502 periodically, e.g., in a time period in a range of about 1 minute to about 15 minutes, or more particularly, in a range of about 3 minutes to about 7 minutes, e.g., about 5 minutes. Although one shutter 1503 is illustrated in FIG. 14C, it should be appreciated that two or more shutters may be provided. The shutter(s) 1503 can be used in static calibration procedures to provide the system with absolute temperature values. In some embodiments, only static calibration is performed, e.g., no dynamic calibration is performed. In some embodiments, both static and dynamic calibration procedures are performed.

The lens assembly 1502 can include a first lens array 1502A and a second lens array 1502B. In some embodiments, the lens assembly 1502 can comprise an array of two-part lenses denoted by the first and second arrays 1502A, 1502B. In some embodiments, the lens assembly 1502 can comprise an array of two separate lenses denoted by the first and second arrays 1502A, 1502B. Each of the lens arrays 1502A, 1502B can comprise a 4×3 array of lenses, each of which may correspond to a particular detector region in the FPA unit 1508 and can define an optical channel of the system 1000. The lenses used in the first lens array 1502A may be different from the lenses used in the second lens array 1502B. The lenses can be any suitable type of lens, including, e.g., spherical lenses, aspheric lenses, rod lenses, etc. or any combination thereof. For example, the lenses used in the first lens array 1502A can comprise aspheric lenses, and the lenses used in the second lens array 1502B can comprise rod lenses. Although the lens assembly 1502 shown in FIG. 14C includes two lens arrays, it should be appreciated that additional lens arrays may be used, e.g., three lens arrays, four lens arrays, five lens arrays, etc. In addition, to assist in enabling a small system size, the diameter of each lens in the assembly 1502 can be less than about 0.5", e.g., in a range of about 0.1" to about 0.5". The f-number of each lens can be less than about 2, e.g., in a range of about 0.2 to 2, or more particularly, in a range of about 0.5 to 2, or 1.0 to 2 or 1.1 to 2.

The first lens array 1502A and the second lens array 1502B can be coupled to one another by way of a mounting plate 1584 sized and shaped to support or receive each lens array 1502A, 1502B. For example, the first lens array 1502A can be mounted on one side of the mounting plate 1584, and the second lens array 1502B can be mounted on an opposite side of the mounting plate 1584. The mounting plate 1584 can be machined to have diameter tolerances of about +/−25 microns. The lenses of the arrays 1502A, 1502B can be secured to the mounting plate 1584 with a curable epoxy. For example, the lenses may fit into opposite sides of holes formed in the mounting plate 1584.

The optical FPA unit 1508 can comprise any suitable type of detector array that is configured to detect infrared radiation, for example, greater than 1 micron, or greater than 2 microns, or greater than 3 microns or greater than 5 microns, or greater than 6 microns and possibly lower than 20 microns, or 15 microns, or 13 microns, or 12 microns or 10 microns, in wavelength, and may be cooled or uncooled. In some embodiments the optical FPA unit 1508 comprises one or more microbolometer arrays, which may be uncooled. For example, an array of about 1000×1000 microbolometer arrays may be used in the embodiments disclosed herein. Microbolometer arrays such as those manufactured by DRS Technologies of Arlington, Va., and Sofradir EC, Inc., of Fairfield, N.J., may be suitable for the embodiments disclosed herein. For example, the DRS U8000 FPA manufactured by DRS Technologies may be used in some embodiments. In some arrangements, the microbolometer array may have a resolution of 1024×768 with a pixel pitch of 12 microns. The array of lenses can form separate channels having image detection regions that form part of the array. For example, 12 channels can be included in the 1024×768 pixel array with on the detector array (microbolometer array) that are for example 250×250 pixels for each of the 12 channels. Detector arrays having more or less pixels may be employed. Similarly the number of channels be larger or smaller than 12 and the detection are on the detector array for a single channel may be larger or smaller than 250×250 pixels. For example, the detection region may comprise from between 100-200 pixels×100-200 pixels per detection region, For example, the detection region may comprise from between 100-200 pixels×100-200 pixels per detection region, from between 200-300 pixels×200-300 pixels per detection region, or from between 300-400 pixels×300-400 pixels or from between 400-500 pixels×400-500 pixels. Likewise the detection region for a channel may measure 100-200 pixels on a side, 200-300 pixels on a side, 300-400 pixels on a side, 400-500 pixels on side or larger or smaller. In some arrangements, the spectral band of the microbolometer can be about 7.5 microns to 14 microns. The microbolometer array can operate at a frame rate of about 30 Hz and can operate at operating temperatures of about −40° C. to +70° C. In various embodiments, the microbolometer array is an uncooled microbolometer that does not include a cooler. The sensitivity of the microbolometer at F/1 can be < about 40 mK. The systems 1000 disclosed herein can be used to detect wavelengths in a range of about 1 micron to about 20 microns. For example, the systems 1000 disclosed herein can be used to detect wavelengths above about 6 microns, e.g., in a range of about 6 microns to about 18 microns, or more particularly, in a range of about 7 microns to about 14 microns. In various embodiments, the individual detector elements of the microbolometer array can be spaced relatively close together to at least partially enable a small, compact system. For example, adjacent detector elements of the array can be spaced apart by a distance in a range of about 7 microns to about 15 microns, or more particularly in a range of about 9 microns to about 13 microns, e.g., about 11 microns. The individual lenses can be spaced apart by a distance in a range of about 20 mm to about 35 mm, e.g. in a range of about 24 mm to about 30 mm, e.g., about 27.5 mm. Likewise the spatially and spectrally spaced channels may be physically spaced apart by 20 to 35 mm, 24 mm to 30 mm, etc. Although various embodiments of the system are described as including an FPA comprising for example a mircobolometer array, certain embodiments comprise a plurality of FPAs. In some embodiments, a single optical FPA is used. In some embodiments, detectors of the optical FPA are configured to detect radiation in the same band of IR wavelengths.

The on-board processing electronics of the data acquisition and processing module 1020 can process the IR optical data to detect and/or identify a target species from the IR radiation received at the optical FPA. For example, the module 1020 can be configured to acquire multispectral image data and analyze the acquired image data to identify the target species. For example, the mobile imaging systems 1000 disclosed herein can be configured to image a 10 m×10 m object area at a distance of about 17 m at a resolution of about 0.04 m. In this example, any gas leaks that generate a gas cloud of at least about 1.5 inches in size can be detected and/or identified by the system 1000. The detection and identification methods can be performed substantially in real-time such that the user can be alerted if any leaks are identified.

As explained above, the infrared image data captured by the system 1000 can be processed on board the data acquisition and processing module 1020 of the imaging system 1000. One way to provide a smaller system 1000 is to process the image data using one or more field-programmable gate arrays (FPGA) configured to execute methods used in the analysis of the images captured by the optical system 1015. In some embodiments, one or more Application Specific Integrated Circuits (ASICs) may be used instead of, or in addition to, the FPGAs. For example, an ASICs chip may include an FPGA. The FPGA(s) (and/or ASIC(s)) can be mounted to and electrically coupled with the substrate(s) 1586 shown in FIG. 14C and can be physically located proximate the optical system. For example, the FPGA can include logic gates and read access memory (RAM) blocks that are designed to quickly implement the computations used to detect the types of gases in a gas cloud. The small size/weight, and high performance characteristics of the FPGA can enable on board computation and analysis within the data acquisition and detection unit 1020 worn or carried by the user. The use of FPGA (or similar electronics) on board the system 1000 can reduce costs associated with using an off-site central server or larger computing device to conduct the image analysis computations. Advantageously, the embodiments disclosed herein can enable on-board computation even though it can be challenging to implement complex methods on the limited computing platform that FPGAs provide.

In addition, enabling computation with one or more FPGA devices on board the wearable system can also prevent or reduce communication bottlenecks associated with wirelessly transmitting large amounts of raw data from the system 1000 to a remote server or computer. For example, the infrared optical system 1015 disclosed herein may generate up to about 380 Mbps of raw image data at 30 frames per second, and the visible sensor 1580 may generate about 425 Mbps of raw image data at 30 frames per second. The resulting data rate of about 800 Mbps is faster than most conventional wireless technologies. While data compression and/or pre-processing may reduce the raw data rates for the visible and IR images, in some embodiments, the IR image data may only be compressed by a ratio of about 2:1. The resulting overall data rate of about 192 Mbps may not be transmitted effectively by conventional wireless communications devices. Accordingly, performing the image processing calculations on board the system 1000 (e.g., on the data acquisition and processing module 1020) can reduce the occurrence of or avoid bottlenecks generated by wirelessly communicating the raw image data to an off-site central server.

One challenge to implementing a mobile imaging system is the power requirements of each component of the system, including, e.g., the IR optical system 1015, the visible sensor 1580, the processing electronics, the wireless communications modules, etc. Advantageously, the mobile infrared imaging systems 1000 disclosed herein can be configured to operate by battery power for long periods of time without recharging or replacing the batteries 1588. In some arrangements the one or more batteries 1588 can comprise lithium ion batteries, which have relatively high energy densities. In addition, to help reduce power consumption within the system 1000, the FPGAs of the data acquisition and processing module 1020 can be advantageously programmed such that power consumption is lower than that used for other types of processing electronics.

The systems 1000 disclosed herein can advantageously operate for between 8 hours and 36 hours without recharging or replacing the batteries, or more particularly between about 10 hours and 24 hours without recharging or replacing the batteries. In some embodiments, the system 1000 can operate for at least about 12 hours without recharging or replacing the batteries. The components of the data acquisition and processing module 1020 (including the imaging optics, focal plane array, and on board processing electronics may) can be configured to operate at relatively low electrical power levels, e.g., at power levels in a range of about 3 W to about 10 W, or more particularly in a range of about 4 W to about 7 W, or in a range of about 4 W to about 6 W, e.g., about 5 W in some embodiments. The components of the data acquisition and processing module 1020 (including the imaging optics, focal plane array, and on board processing electronics may) can also be configured to operate at relatively low overall energy levels for a single charge of the batteries 1588, e.g., at energy levels in a range of about 60 Watt-hours (Wh) to about 100 Wh, or more particularly in a range of about 80 Wh to about 95 Wh, or in a range of about 85 Wh to about 90 Wh.

In addition, for each of the embodiments disclosed herein, various motion detection and/or compensation techniques can be implemented to account for relatively large-scale motions that are induced by the user moving his or her head during use. For example, when a user is visiting a well site or other installation, the user may be continuously walking and looking in different directions (e.g., by rotating his or her head). Additionally, vibration can be introduced by the user's natural unsteadiness. Such movement can continuously change the system's field of view at a relatively rapid rate, which can affect the accuracy of the methods used to determine the identity of species in a gas cloud or other object. Accordingly, it can be desirable to provide improved motion detection and/or compensation techniques to reduce errors associated with the movements of the user.

Each of the embodiments disclosed herein can be used to estimate various characteristics of gases present in a gas leak imaged by the infrared imaging systems disclosed herein.

IV. Examples of Remote Monitoring Systems and Methods

Various embodiments disclosed herein enable the efficient monitoring of multiple DAISI systems at one or more sites situated at one or multiple installations or facilities, or any combinations thereof. For example, various embodiments disclosed herein relate to the remote monitoring of petrochemical installations. As explained herein, petrochemical installations, such as hydrocarbon well sites (e.g., oil, natural gas, or other drilling sites for petrochemicals), petrochemical processing sites, petrochemical transportation and/or storage sites, may be located in remote areas that are many miles from population centers, and/or that otherwise lack access to high speed communications networks (such as high speed optical networks, or other high speed wired or wireless networks). Although many embodiments disclosed herein relate to the monitoring of petrochemical installations, it should be appreciated that these embodiments could similarly be deployed at any suitable type of installation, including, e.g., chemical plants, manufacturing facilities, etc. For example, petrochemical installations may be located at remote sites without reliable high speed cellular or wireless communications with a central processing facility or server. In some arrangements, the remote petrochemical installations may communicate with the central processing facility or server by way of slower, low frequency, low bandwidth cellular networks. Transmission of large amounts of data over these slower cellular networks may result in excessively long transmission times and the overuse of network resources.

In various embodiments, a system for monitoring a petrochemical installation is disclosed. The system can include any suitable processing electronics, including processors, computer-readable memory readable by the processors, and any other suitable hardware, which may be interconnected by a communications networks. The system can include an optical imaging system comprising an array of optical detectors and processing electronics configured to process image data detected by the optical imaging system. The processing electronics can be configured to detect a target species based at least in part on the processed image data and, based on a detected amount of the target species, transmit an alarm notification to an external computing device over a communications network indicating that the target species has been detected at the petrochemical installation.

In some embodiments, the processing electronics can be configured to detect the target species over multiple frames of the image data and to combine the multiple frames of image data into a summary image that presents the detection of the target species over a period of time. In various embodiments, the summary image comprises a single image. In other embodiments, the summary image comprises a plurality of images. The processing electronics can be configured to create the summary image by calculating an average concentration of the target species over a plurality of successive frames, and/or an average of the image data representative of the concentration, over the period of time, or other calculations based on an accumulation of values (such as concentrations or data for calculating concentrations) over time. In some embodiments, the processing electronics can be configured to create an events log comprising a plurality of events comprising one or a plurality of target species detected by the processing electronics. The processing electronics can be configured to analyze the events log, and based on the analysis, to transmit a priority ranking of events to the external computing device. For example, the processing electronics can be configured to assign a higher priority to more dangerous gases (e.g., hydrogen sulfide) than to other gases. As another example, the processing electronics can be configured to assign a higher priority to a gas leak in which the concentration of leaked gas is greater than another gas leak with a lower concentration of leaked gas. Still other ways of assigning priority may be suitable.

In various embodiments, the processing electronics can be configured to compare the detected amount of the target species to a threshold amount and, based on that comparison, transmit the alarm notification to the external computing device over the communications network indicating that the target species has been detected at the petrochemical installation. In some implementations, the threshold amount can be in a range of 1 ppm-m to 1000 ppm-m of the target species. In some implementations, the threshold amount can be in a range of 25 ppm-m to 1000 ppm-m of the target species. In some implementations, the threshold amount can be in a range of 25 ppm-m to 750 ppm-m of the target species, or in a range of 50 ppm-m to 550 ppm-m.

The target species can be any suitable type of target species, including, e.g., various types of petrochemical species including liquids and/or gases. In some embodiments, the target species comprises methane. In some embodiments, the target species comprises hydrogen sulfide. In various embodiments, the target species comprises a gas. In various embodiments, the target species comprises a liquid, such as oil.

In various embodiments, the processing electronics can be configured to detect an unauthorized intrusion of an animal (including a human) into the petroleum installation and, based on the detection, to transmit a second alarm notification to the external computing device over the communications network indicating the unauthorized intrusion. The processing electronics can be programmed with various thresholds so as to ensure that only various unauthorized events and/or unexpected leaks are detected and transmitted to the external computing device. In various embodiments, for example, the processing electronics can comprise image recognition and/or motion detection techniques to determine if there is an unauthorized intrusion. In various systems, the external computing device may be bombarded with numerous extraneous alarms or notifications if the detection events criteria and/or thresholds are not adequately set. In the embodiments disclosed herein, the detection events can correspond to various predetermined thresholds or detection criteria such as but not limited to those disclosed herein.

In some embodiments, the communications network comprises a wireless communications network. In various embodiments, the wireless communications network comprises a cellular communications network, e.g., conforming to any suitable cellular communications standard, such as 3G, LTE, etc. The processing electronics can be configured to transmit processed image data (such as a summary alarm image) to the external computing device at speeds in a range of 0.1 Mbps to 10 Mbps. In some embodiments, the processing electronics can be configured to transmit processed image data (such as a summary alarm image) to the external computing device at speeds in a range of 0.5 Mbps to 2 Mbps. In various embodiments, the processing electronics can be configured to render a user interface presentable to a user on a display device. The user interface can comprise a visible image window and an infrared image window showing images obtained using primarily visible light and infrared light respectively (e.g., using visible and infrared imaging sensors, respectively).

The optical imaging system can include any of the optical imaging systems disclosed herein, e.g. any of the systems disclosed in FIGS. 1-14C. For example, the optical imaging system can comprise one or more infrared (IR) detector arrays. The optical imaging system can additionally or alternatively comprise a visible light detector array. The optical imaging system can define a plurality of optical channels being spatially and spectrally different from one another, each of the plurality of optical channels positioned to transfer radiation incident on the optical imaging system towards the array of optical detectors. In various embodiments, the optical imaging system and the processing electronics can be contained together in a data acquisition and processing module configured to be worn or carried by a person. The optical imaging system and the processing electronics can be configured to be mounted to a support structure at the petroleum installation. The optical system can comprise a plurality of spectrally distinct infrared optical filters. In other embodiments, the monitoring systems and methods can be used in conjunction with other types of imaging systems (e.g., IR systems), including single channel imaging systems or any other suitable type of imaging systems.

Figure 15A:
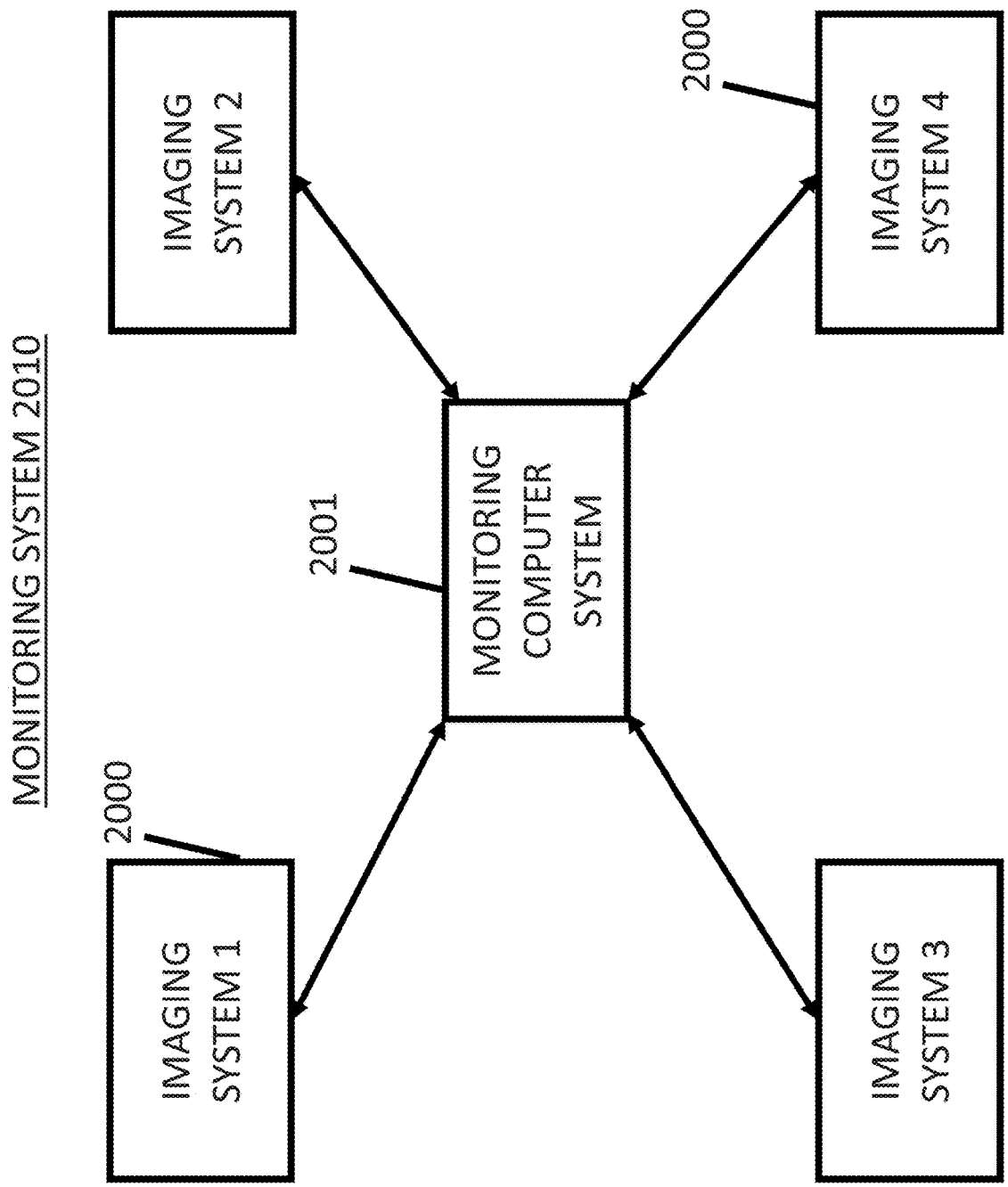
FIG. 15A is a schematic system diagram showing a monitoring system for detecting and/or identifying fluid leaks from a remote installation, according to various embodiments.

FIG. 15A is a schematic system diagram showing a monitoring system 2010 for detecting and/or identifying fluid leaks (e.g., gas or liquid leaks) from one or a plurality of sites situated at one or a plurality of remote installations or facilities (e.g., a petrochemical facility). As shown in FIG. 15A, the system 2010 can comprise a plurality of imaging systems 2000 disposed at a corresponding plurality of locations, installations, or facilities. The imaging systems 2000 can be disposed at different locations within a particular installation or facility, for example, at different locations within a large oil refinery. In other arrangements, the imaging systems 2000 can be disposed at facilities at entirely different geographic locations that may be geographically remote. In FIG. 15A, four imaging systems 2000 (Imaging System 1, Imaging System 2, Imaging System 3, and Imaging System 4) are illustrated, but it should be appreciated that more or fewer imaging systems 2000 may be monitored by the system 2010 shown in FIG. 15A.

The imaging systems 2000 can comprise any of the imaging systems disclosed herein in FIGS. 1-14C, including, e.g., the DAISI systems disclosed herein. The imaging systems 2000 can be configured to be worn or carried by a person, can be fixedly mounted to a tower or pole (or other fixed structure or building), can be mounted to a truck or other moving vehicle, or can be attached to an aerial platform (such as a drone or other aircraft). The imaging systems 2000 can comprise multi-spectral (e.g., multi-channel) infrared imaging systems, similar to the systems disclosed herein. In other embodiments, however, the imaging systems 2000 can comprise other types of imaging systems, e.g., single channel IR imaging systems, or non-IR imaging systems.

As shown in FIG. 15A, each imaging system 2000 can be in network or data communication with a central monitoring computer system 2001 (e.g., one or a plurality of external computing devices) or network of multiple computing devices. The monitoring computer system 2001 can comprise any suitable type of computer system or processing electronics. In some embodiments, the monitoring computer system 2001 can comprise a centralized server with processing electronics and/or one or more communications modules programmed to receive and/or transmit information to and/or from the imaging systems 2000. In some embodiments, the monitoring computer system can comprise a desktop or laptop computer with software stored thereon, or accessed via the Internet (such as over a web browser), that is configured to communicate with the imaging systems 2000. The monitoring computer system 2001 can communicate with the imaging systems 2000 using any suitable communications network, including, e.g., cellular data connections (e.g., 3G, 4G network standards, or any other suitable cellular network standard), wireless network connection (e.g., WiFi connection), wired network connection (e.g., Ethernet connection), etc.

For example, in embodiments in which the central monitoring computer system 2001 is located near the imaging system(s) 2000, a wired or wireless internet connection may be suitable to transfer video and/or other image data over a high bandwidth connection. However, in some embodiments, the imaging system(s) 2000 may be located at facilities that are remote from the monitoring computer system 2001, in which case a cellular network having a relatively low bandwidth may provide wireless data communication between the imaging systems 2000 and the monitoring computer system 2001. In various embodiments, the fluid leak detection and/or identification may be performed at the facility or installation, and the processed image data may be communicated to the monitoring computer system 2001. In other embodiments, the raw image data (e.g., raw IR image data) may be communicated to the monitoring computer system 2001, and the monitoring computer system 2001 may be programmed to detect and/or identify the target species (e.g., target gases or liquids). Still other combinations of detecting and/or identifying the fluid leak are possible.

The monitoring computer system 2001 can be configured with suitable authorization protocols such that only authorized system users can access the computer system 2001 to monitor the selected imaging systems 2000. For example, in some embodiments, monitoring software can comprise computer-readable instructions that when executed, provide the monitoring computer system 2001 (and hence the user) with tools to monitor the imaging systems 2000. As explained herein, the monitoring system software can provide various user interfaces to the user to enable the user to view information about the scene(s) that is/are being imaged by the imaging system 2000, including, e.g., video feeds of the scene(s), alerts or alarms related to fluid leaks, alerts or alarms related to intruders, or any other information detected by the systems 2000. The monitoring systems can further provide tools for the user to interact with the imaging systems 2000, e.g., to select which imaging systems 2000 are to be monitored, to set thresholds for fluid leak detection algorithms, etc.

In various embodiments, the software can be executed on processing electronics associated with each imaging system 2000, and/or with a centralized server associated with the systems 2000, and can be remotely accessed by way of a suitable communications protocol. For example, in some embodiments, each imaging system 2000 can comprise a unique network address (e.g., an internet protocol, or IP, address) that can be accessed over the World Wide Web. When accessed, e.g., over a web browser, a login screen or other authorization mechanism can be presented to the user. The user can enter a suitable username and password combination (or other authentication mechanism) to access the imaging system(s) 2000 associated with the user. The user can view and/or control all the associated imaging systems 2000 through a secure web portal or browser. The embodiments disclosed herein can therefore enable secure, remote access to the monitoring system.

Figure 15B:
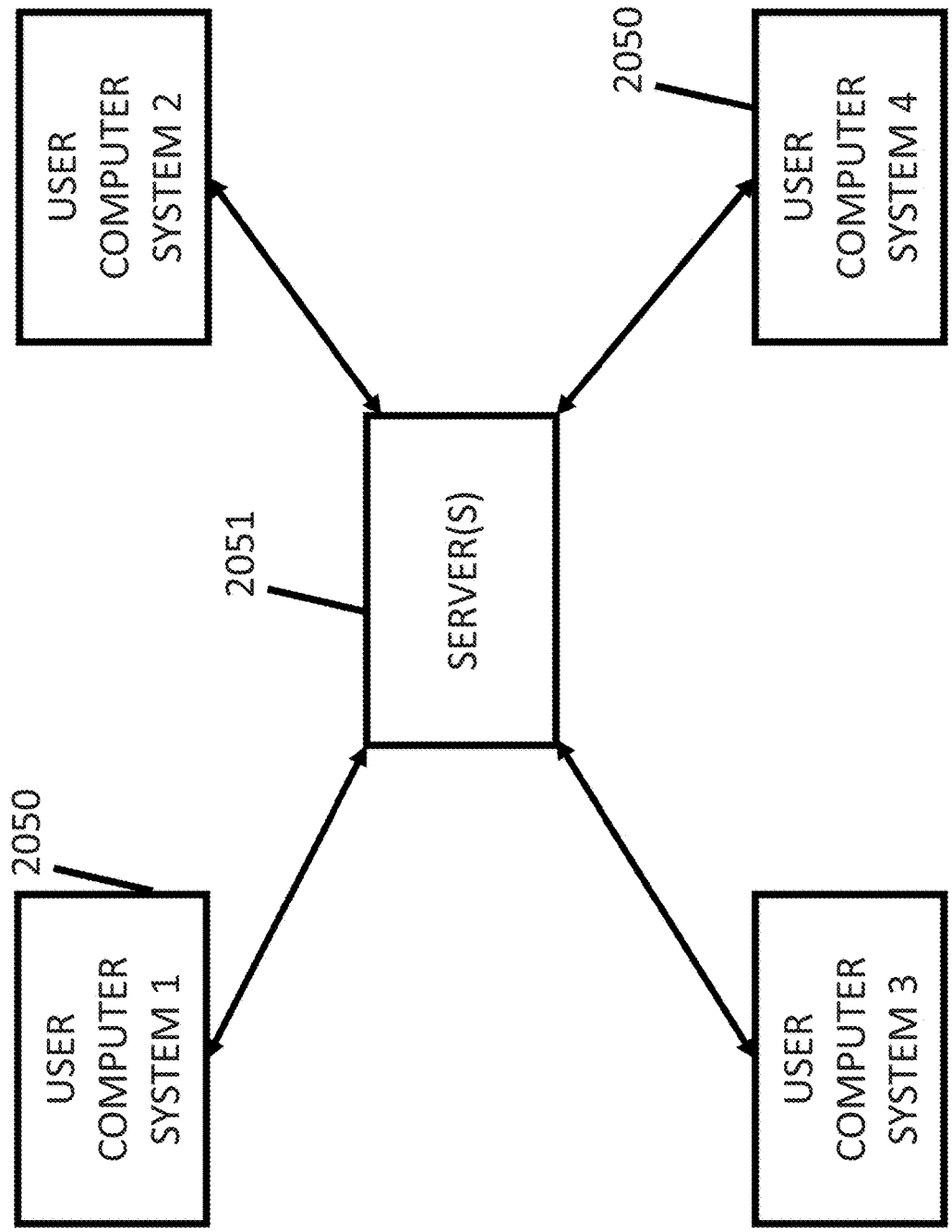
FIG. 15B is a schematic system diagram showing an example of a monitoring computer system, according to various embodiments.

FIG. 15B is a schematic system diagram showing an example of a monitoring computer system 2001, according to various embodiments. As shown in FIG. 15B, the monitoring computer system 2001 can comprise one or a plurality of servers 2051 in network communication with one or a plurality of user computer systems 2050. As explained above, the imaging systems 2000 can communicate with the monitoring computer system 2001 (e.g., the server(s) 2051) over any suitable communications network, such as the Internet by way of a WiFI or Ethernet connection, by a cellular network, etc. In turn, the server(s) 2051 can communicate with the user computer system(s) 2050 by way of any suitable communications network. As explained above, for example, the user computer system(s) 2050 can access information about events (e.g., fluid leaks, etc.) over the Internet by accessing a secure web page hosted by the server(s) 2051. Although the monitoring computer system 2001 utilizes one or more servers to transmit information about events detected at the imaging systems 2000 to the user computer systems 2050, in other embodiments, however, the imaging systems 2000 can communicate directly with the user computer systems 2050 over a communications network, e.g., the Internet, over a cellular communications network, etc.

In various embodiments disclosed herein, the imaging system(s) 2000 can comprise processing electronics that are configured to process captured image data to detect and/or identify a target species, such as a target gas or liquid. The processing electronics of the imaging systems 2000 can be locally connected with the optical components of the system 2000. For example, the processing electronics can be physically located at or near the optical components in some embodiments. In other embodiments, the processing electronics may be remote from the optical components. For example, in other embodiments, the image data can be processed by processing electronics included in and/or associated with the computer monitoring system 2001 such as the server(s) 2051 or user computer system(s) 2050. In various embodiments, and as explained below, processing electronics of the imaging system(s) 2000 can be configured to generate an alarm based on the detection of the target species, and can transmit the alarm to the monitoring computer system 2001 (e.g., the server(s) 2051 in some embodiments). In other embodiments, the processing electronics of the imaging system(s) 2000 or monitoring computer system 2001 can be configured to transmit the alarm to the user computer system(s) 2050. In some embodiments, the processing electronics of the imaging system 2000 can be configured to generate an event log that includes one or more events detected by the imaging system(s) 2000 at the installation being monitored. In other embodiments, the monitoring computer system 2001 can generate the event log. Furthermore, as explained herein, the processing electronics of the imaging system(s) 2000 can be configured to generate the summary alarm image(s) described below, and can transmit the summary alarm image(s) to the monitoring computer system 2001. In various embodiments, the processing electronics of the imaging system(s) 2000 can be configured to generate the time-lapsed image(s) of fluid leaks (such as liquid leaks) described below, and can transmit the time-lapsed image(s) to the monitoring computer system 2001. In various embodiments the server(s) 2051 can transmit the event data at the installation being monitored (including information about fluid leaks, etc.) to the user computer systems 2050, over a communications network. In various embodiments, the user computer systems 2050 can access the information about the event(s) over the network, and can render the information in a user interface to be viewed and/or controlled by the user or operator, who may be remote from the imaging system(s) 2000 and the installations being monitored. In some embodiments, processing electronics of the imaging system(s) 2000 can be configured to generate the progressive mode described below, in which summary alarm image(s) can be generated in a cycle and sent to the user(s), for example, by way of the monitoring computer system 2001. In other embodiments, the monitoring computer system 2001 (e.g., the server(s) 2051) can be configured to generate the progressive mode described herein. In various embodiments disclosed herein, the processing electronics can comprise a first portion of electronics (e.g., one or more processors) at or near the imaging system 2000 and a second portion of electronics (e.g., one or more processors) remote from the imaging system 2000. In some implementations, the processing electronics can be included in whole or in part in the monitoring computer system 2001, e.g. the server(s) 2051 and/or user computer system(s) 2050. Accordingly, in some implementations, the summary alarm image(s), time-lapsed images(s), mosaic images, overview image(s), multi-view or progressive modes, event log, or other images, formats, functions, and/or modes discussed below, may be potentially be produced at least in part by processing electronics in or associated with the monitoring computer system 2001, e.g. the server(s) 2051 and/or user computer system(s). In some implementations, such images, formats, functions, and/or modes may be produced in whole or in part by processing electronics included with the imaging system(s) 2000. In some implementations, processing electronics associated with the imaging system(s) 2000 and processing electronics associated with the monitoring computer system 2001, e.g. the server(s) 2051 and/or user computer system(s) may be used to produce such images, formats, functions, and/or modes.

Figure 15C:
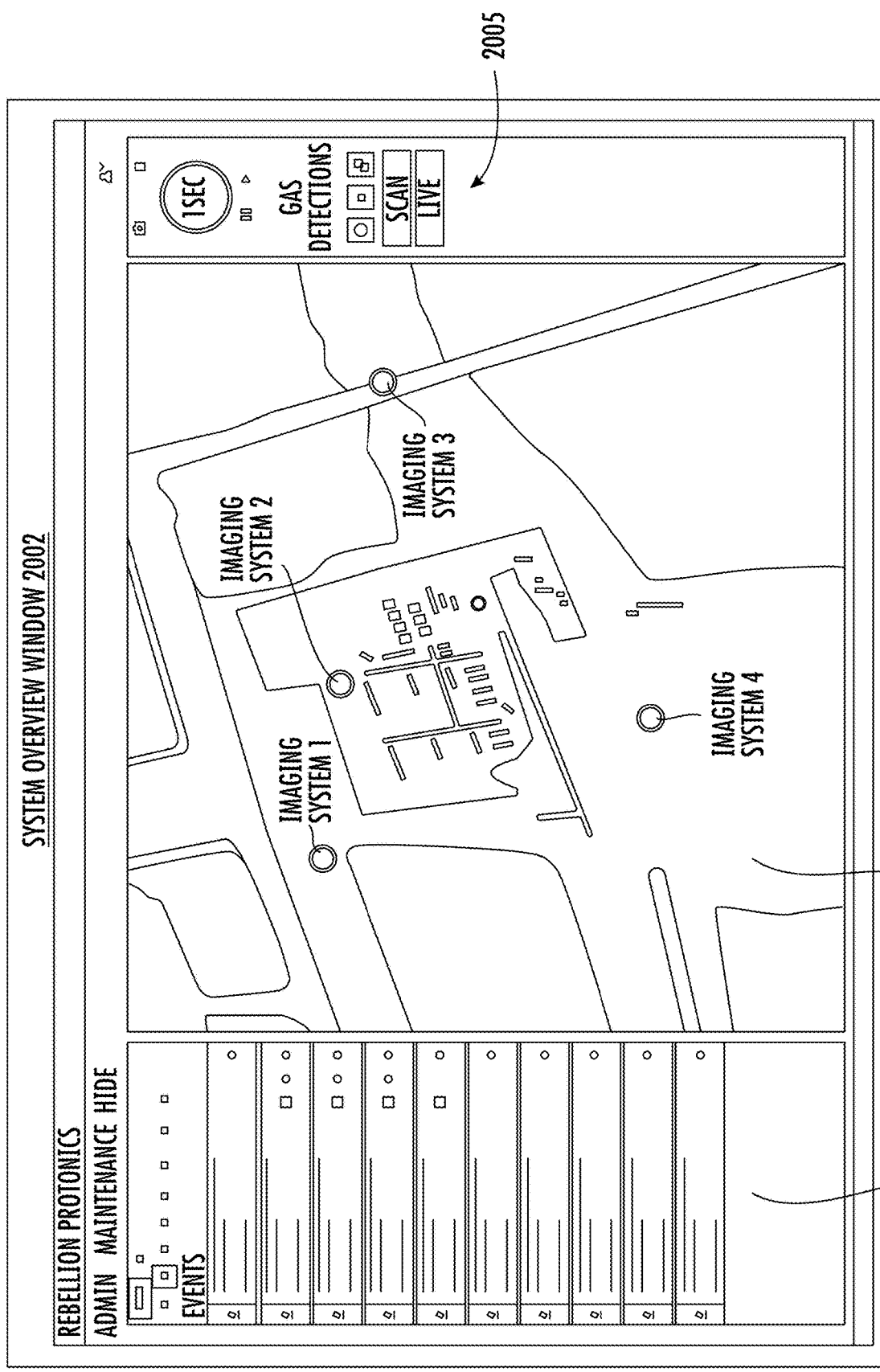
FIG. 15C is a schematic diagram of a system overview window which can be rendered on a display of a central monitoring computer system.

FIG. 15C is a schematic diagram of a system overview window 2002, which can be rendered on a display of the central monitoring computer system 2001. The system overview window 2002 can provide the user or system operator with a system-level overview of the location of each imaging system 2000 (for example, overlaid on a map or image of the locations to be monitored), which may be assigned a unique identifier or name. As shown in FIG. 15C, the system overview window 2002 can comprise an event log panel 2003, an overview image 2004, and a tools panel 2005. As explained in more detail below, the event log panel 2003 can provide the user with information related to events that occur or that are detected by the imaging systems 2000 (e.g., detection of a gas or liquid leak). Also, as explained in more detail herein, the tools panel 2005 can provide the user with an interface to select various modes of operation, select which imaging systems are monitored or displayed in the window, and select other imaging or monitoring parameters, such as alarm thresholds, intrusion detection, etc. The overview image 2004 of the system overview window 2002 can provide a rendering of the locations to be monitored, e.g., overlaid on a map or image of the locations that are to monitored by the imaging systems 2000. In the overview image 2004 of FIG. 15C, for example, Imaging Systems 1 through 4 are schematically overlaid on an image of an installation to be monitored. The imaging systems 2000 can be identified in any suitable manner, for example, by way of a system name or unique identifier. Beneficially, the overview image 2004 can allow the user to determine the physical location of a particular imaging system 2000, for example, if an alarm alerts the user to an event (e.g., fluid leak) at that particular imaging system 2000. Associating an event with a physical location can enable the user or operator to quickly address any urgent events, such as fluid leaks.

Figure 15D:
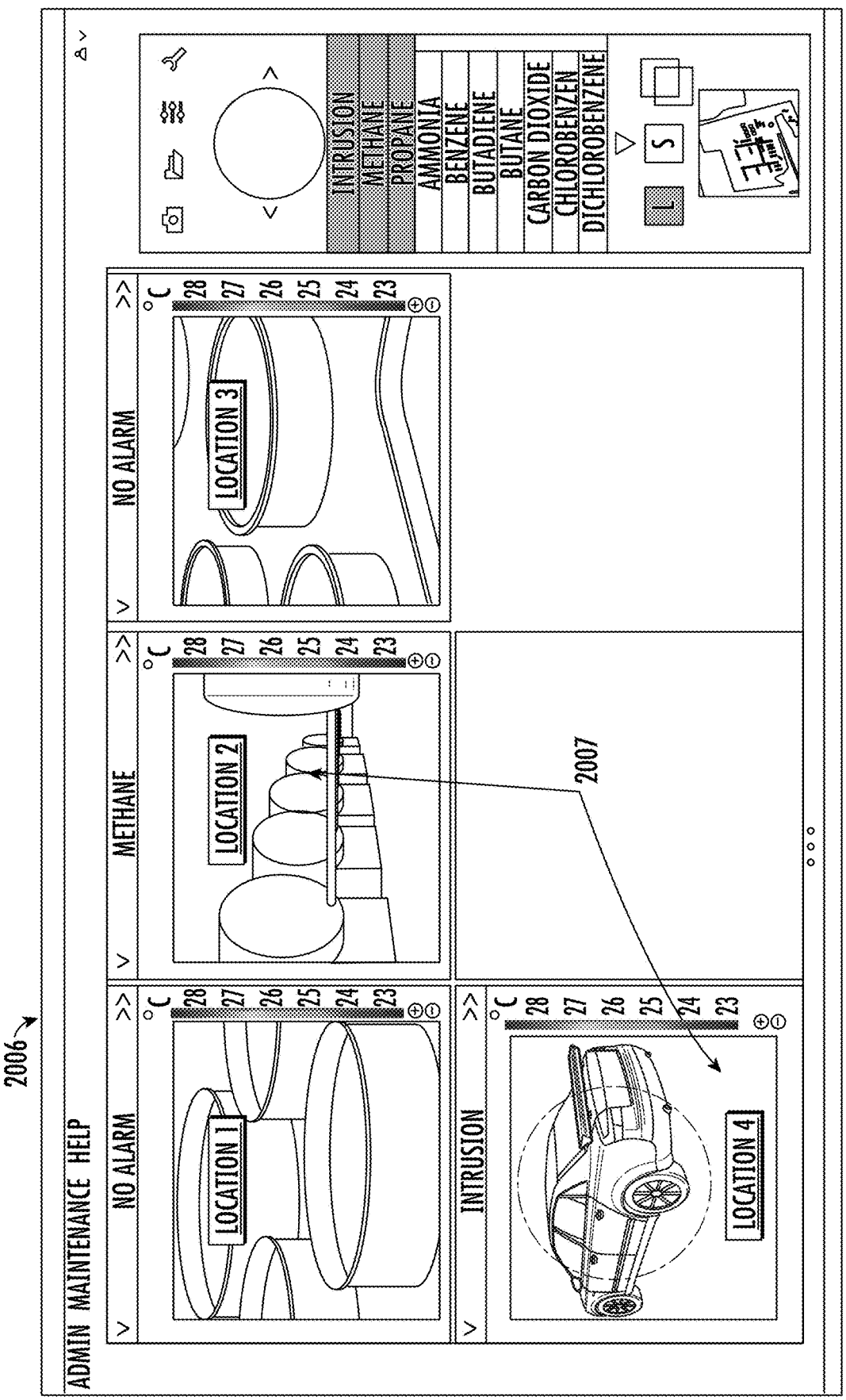
FIG. 15D is a schematic diagram of a multi-view imaging window which can be rendered on the display of a central monitoring computer system, according to various embodiments.

FIG. 15D is a schematic diagram of a multi-view imaging window 2006 which can be rendered on a display of the central monitoring computer system 2001. The multi-view imaging window 2006 can comprise a plurality of images 2007, each of which are associated with a different imaging system 2000. For example, as shown in FIG. 15D, a first image 2007 can comprise an image (e.g., visible or IR image) of a particular field of view (FOV) at a first location that is being monitored by Imaging System 1. Similar, a second image 2007 can comprise an image (e.g., visible or IR image) of a particular FOV at a second location that is being monitored by Imaging System 2; a third image 2007 can comprise an image (e.g., visible or IR image) of a particular FOV at a third location that is being monitored by Imaging System 3; and a fourth image 2007 can comprise an image (e.g., visible or IR image) of a particular FOV at a fourth location that is being monitored by Imaging System 4.

The multi-view window 2006 can beneficially enable the user to view at least one FOV of each location that is being monitored by the imaging systems 2000 of the monitoring system 2010. If an event is detected at a particular location and imaging system 2000, the system 2010 can alert the user to the location at which the event occurs on the multi-view window 2006. The user can select the location at which the event is detected to obtain more information about the event, and/or can view the event in the event log 2003. The images 2007 of the multi-view window 2006 can be viewed in a progressive viewing mode, which is explained in more detail below. As explained below, the progressive viewing mode can give the user a high-level, low resolution overview of each location that is being monitored by the respective imaging systems 2000.

Figure 16A:
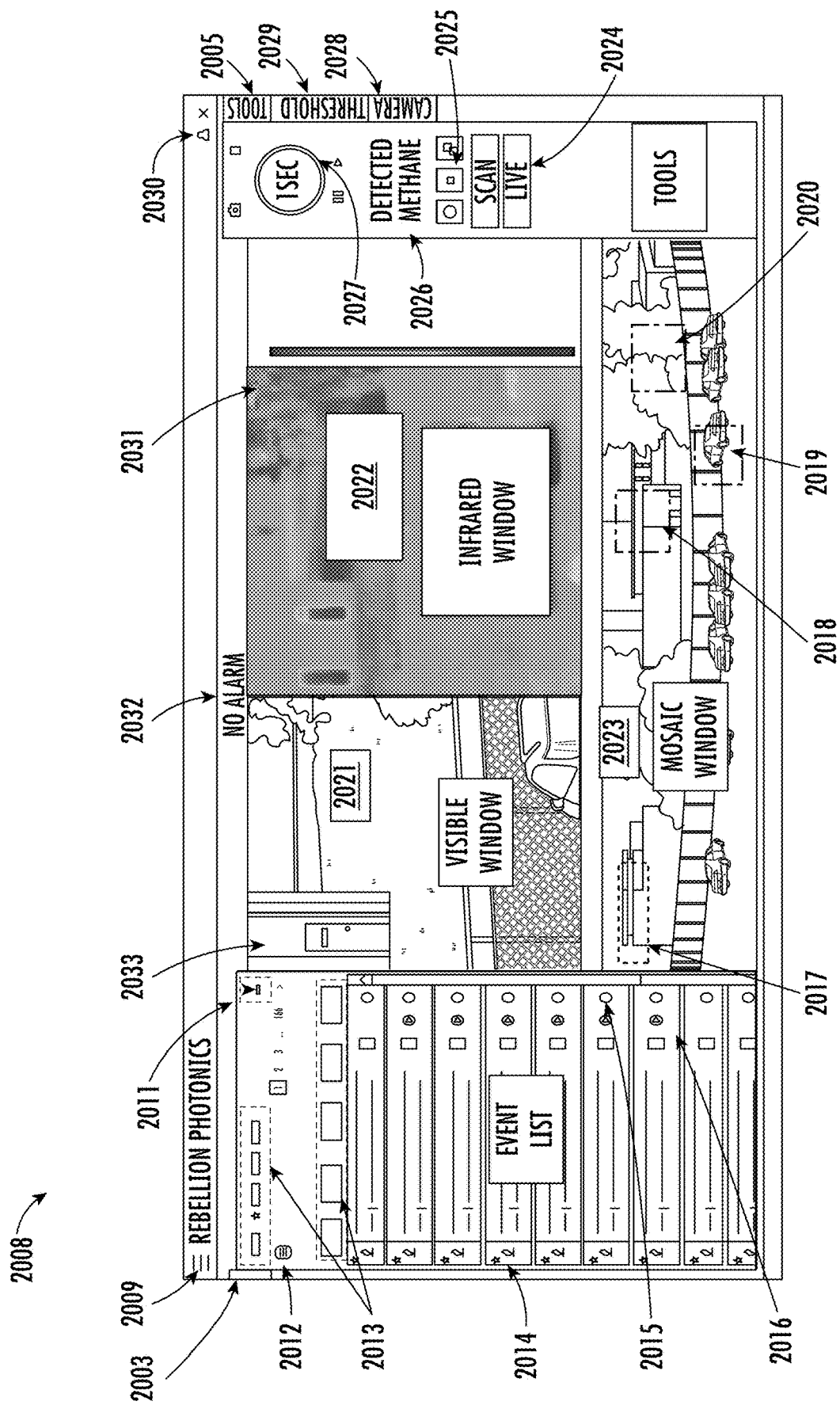
FIG. 16A is a schematic diagram of a single imaging system window, according to various embodiments.

FIG. 16A is a schematic diagram of a imaging system window 2008, according to various embodiments. The imaging system window 2008 can be rendered on the display of the central monitoring computer system 2001. The imaging system window 2008 can render information associated with a particular imaging system 2000, e.g., any one of Imaging Systems 1 to 4. The user can access the imaging system window 2008 associated with a particular imaging system 2000 by engaging with a user interface of the computer system 2001, e.g., by selecting a particular imaging system 2000 from a menu, by selecting an associated image 2007 from the multi-view window 2006, or in any other suitable manner. The imaging system window 2008 can advantageously provide the user with detailed information (including information about various events, etc.) associated with the particular imaging system 2000.

As shown in FIG. 16A, the imaging system window 2008 can comprise an events log panel 2003 (which can log events from one or a plurality of imaging systems 2000 at one or a plurality of locations), a menu 2009 for navigating to various other views or tools, a visible image window 2021, an infrared image window 2022, a mosaic image window 2023, and a tools panel 2005, as discussed below. In various embodiments, the visible image window and the infrared image window, obtained primarily with visible light and infrared light, respectively, can be displayed simultaneously on the user interface, e.g., side-by-side in a split image view. FIG. 16B is a schematic diagram of another example of the mosaic image window 2023. The mosaic image window 2023 can provide the user with a mosaic image of the entire field of view (FOV) that is imaged by the particular imaging system 2000, for example, as the imaging system 2000 is scanned or moved across the scene. As shown in FIGS. 16A-16B, for example, the mosaic image window 2023 can enable the user to view the full scene which can be monitored by the imaging system 2000 of interest.

Within the larger mosaic image are a plurality of detection FOVs, associated with corresponding detection regions which are monitored by the imaging system. For example, as shown in FIGS. 16A-16B, the imaging system 2000 can comprise a plurality of designated or "stored" FOVs 2020 within the mosaic image. It should be appreciated that, as used herein, the designated or "stored" FOVs 2020 can correspond to FOVs that the imaging systems 2000 monitor at various time periods. Thus, the designated or "stored" FOVs 2020 can be regularly monitored by the imaging system(s) 2000 to detect fluid leaks. The imaging system(s) 2000 can monitor one designated FOV 2020 during a first time period (or first dwell time), and after the first time period, can monitor another designated FOV 2020 for a second time period (or second dwell time), and so on until different monitored FOVs 2020 are observed for a desired time period or dwell time. The system 2000 can cycle through the FOVs 2020 repeatedly, e.g., to continually, monitor the petrochemical installation. For example, as shown in FIG. 16A, the user can engage with a path configuration interface 2017 to cause the system 2010 to regularly and repeatedly monitor the stored detection FOVs 2020 to determine if there are any fluid leaks (e.g., gas leaks or oil leaks). The user can cause the path configuration interface 2017 to cycle through the stored FOVs 2020 in any desired order. For example, the mosaic window 2023 can be used to change the FOV and the programmed paths taken by imaging systems 2000. Thus, in the embodiments disclosed herein a path can comprise a series of different FOVs that are looped continuously in a cycle. When a particular FOV is to be monitored in the cycle, the imaging system 2000 can monitor the FOV for events such as fluid leaks, and the particular FOV can be rendered on the visible and/or IR image windows 2021, 2022.

Thus, at a particular time period, a particular active FOV 2019 can be selected (e.g., automatically or manually by the user) within the path cycle (e.g., the order that FOVs are monitored by the system 2000). The selected active FOV 2019 can correspond to the detection FOV that is being monitored during the particular time period. As shown in FIG. 16A, for the particular active FOV 2019, the imaging system window 2008 can render the active FOV 2019 in the visible image window 2021 and in the IR image window 2022. The visible image window 2021 can correspond to visible image data captured from a visible camera, such as a pan-tilt-zoom (PTZ) camera 2033. The IR image window 2022 can render IR image data taken from one or more of the multiple channels of the IR imaging camera (e.g., a DAISI or other IR system). An infrared or temperature bar 2031 can provide the user with an estimate of the temperature in the infrared image window 2022. A status bar 2032 can be provided to indicate the status of the detection process to the user, e.g., whether or not there is an alarm within the particular FOV representative of a fluid leak. In various embodiments, if a fluid leak is detected, the fluid leak can be viewed in real-time video, as a colored schematic representation overlaid on the IR (or visible) image. In some embodiments, if a leak is detected, image data of the FOV in which the leak is observed can automatically pop up as video data and/or as a summary alarm image. In some embodiments, the image data can be manually retrieved by the user, e.g., by way of the event log panel 2003.

The visible and IR image windows 2021, 2022 can beneficially provide the user with enlarged visualizations of the active FOV 2019 while the imaging system 2000 is determining whether there are any fluid leaks within the active FOV 2019. If the system 2000 determines that there are fluid leaks within the active FOV 2019, then the imaging system 2000 can trigger an alert, which can update the status bar 2032 and/or the event log 2003. If no fluid leak is detected, then the status bar 2032 can indicate that no alarm or alert is present. When the monitoring time period (e.g., 15 sec) is over, another stored FOV 2020 is cycled to become the active FOV 2019, and so on until every stored FOV 2020 in the mosaic image window 2023 is monitored. The path cycle repeats so that the sites in the installation can be continually monitored over time. For example, at the end of the monitoring time period, the imaging system 2000 can be moved (e.g., rotated, tilted, translated, etc.) so that another FOV 2020 is monitored by the imaging system 2000. If a fluid leak (e.g., gas or liquid leak) is detected within a particular active FOV, then the FOV in which the leak is detected can be denoted within an alarm FOV 2018. Advantageously, the alarm FOV 2018 can be color coded to easily alert the user to the presence of an event such as a fluid leak.

The tools panel 2005 of the imaging system window 2008 can include various interactive tools that the user can engage to select the FOVs of which imaging systems 2000 are to be rendered in the imaging system window 2008. The tools panel 2005 can also include a fluid threshold tab 2029 in which the user can select threshold values for the fluid detection algorithm, e.g., to make the algorithm more or less sensitive based on the user preferences. For example, the user can modify threshold values for one or more gases or liquids that are being monitored. The system 2000 will alarm when the threshold values are exceeded for that particular gas or liquid The tools panel 2005 can comprise a camera selection 2028 tab in which the user selects which imaging system's FOV is rendered in the imaging system window 2008. Further, the tools panel 2005 can include a timer indicator 2027, which indicates the amount of time that a particular designated or "stored" FOV 2020 is being monitored at a particular period and is rendered on the imaging system window 2008. As explained above, the system 2010 can cycle through the designated or "stored" FOVs 2020 to monitor the particular FOV for fluid leaks during a predetermined period of time, or dwell time (e.g., 15 seconds, 30 seconds, 1 minute, etc.). For example, as explained above, the system 2010 can render image data (e.g., video stream and/or summary alarm image) of a first FOV during a first time period or dwell time. After the first time period or dwell time expires, the system 2010 can render image data (e.g., video stream and/or summary alarm image) of a second FOV during a second time period or dwell time. The system 2010 can cycle through the FOVs to repeatedly (e.g., continually) observe successive FOVs for respective dwell times. The tools panel 2005 can also include a gas list 2026, indicating which gases (or other fluids) are being actively monitored by the systems 2000. The user can select any suitable number of fluids to be monitored. In addition, in some embodiments, the user can elect to also monitor for intrusions by unwanted third parties into the FOV. A view options bar 2025 can be provided to allow the user to view, for example, only the visible image window 2021, only the IR image window 2022, or a split screen (FIG. 16A) that shows the visible image window 2021, the IR image window 2022, and the mosaic window 2023, or any combination thereof. A viewing mode bar 2024 can be provided to allow the user to select a desired viewing mode, e.g., a live-stream video mode, a progressive mode (discussed below), etc. A user bar 2030 can indicate which user is logged onto the system, and/or additional information about the user (e.g., user's authorization status, user's name and location, etc.).

The events log 2003 can provide an indication of the events that have been detected by the system 2010, e.g., events at a particular imaging system 2000 and/or system-wide events for all (or a plurality of) imaging systems 2000. The events log 2003 can comprise a download interface 2011 to enable the user to download one or a plurality of the logged events. The downloaded events can be presented in a spreadsheet-style document. In some embodiments, the user can download video streams and/or summary images (see FIG. 16C) by way of the events log 2003 and download interface 2011. An acknowledge-all interface 2012 can be provided so that the user can acknowledge all listed events. Further, individual acknowledgement interfaces 2015 can be provided so that the user can acknowledge a particular event (or events) to indicate that the user has addressed the event in an appropriate manner. In addition, a sort interface 2013 can be provided such that the user can sort the events in any suitable manner, e.g., sort by type of alarm, date and time of alarm, etc. The user can engage a highlight event interface 2014 to indicate events that should be followed up with at a later date. As explained herein, the user can select a video or summary image link 2016 to view the video feed or summary image (see below) associated with the particular event (such as a gas leak).

Figure 16C:
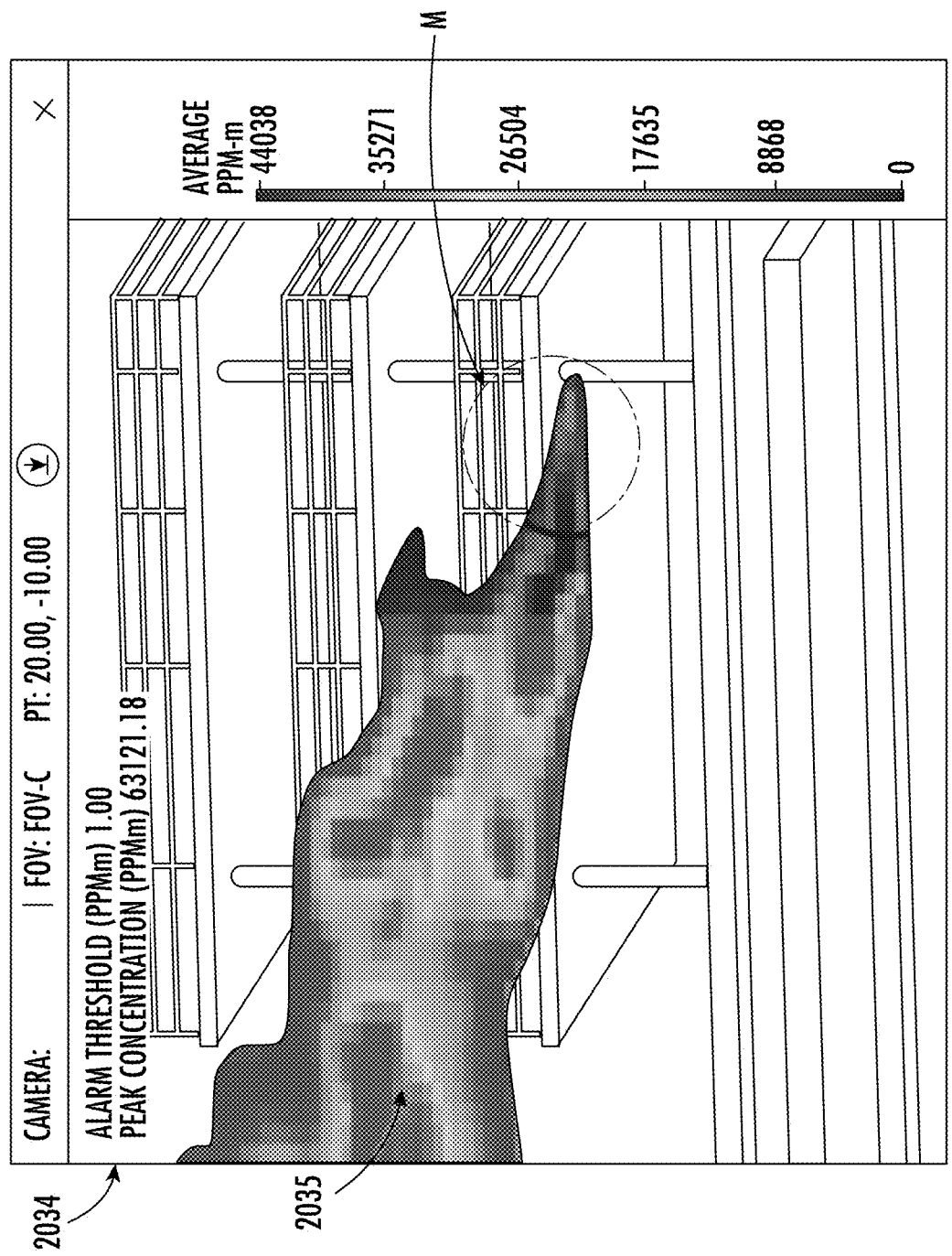
FIG. 16C illustrates an example of a summary alarm image, according to various embodiments.

Turning to FIG. 16C, an example of a summary alarm image 2034 is illustrated, according to various embodiments. In the summary alarm image 2034 shown in FIG. 16C, a detected target species 2035 is overlaid over an image of the scene being monitored by the imaging system 2000. The summary alarm image 2034 can comprise a color map representative of concentrations of the target species (e.g., red for high concentrations and blue for low concentrations, or vice versa). As explained herein, some petrochemical installations may be located in remote physical locations, miles away from any infrastructure or populated areas. In such locations, high speed internet connections (e.g., optical communications networks, or other high speed connections) may be unavailable. In such remote facilities, lower speed (and lower bandwidth) cellular networks may be used to provide wireless communications between remote imaging systems 2000 and the monitoring computer system 2001. Such low speed cellular networks may not provide adequate bandwidth for the transmission of high resolution, high frame rate raw image data. Accordingly, various embodiments disclosed herein utilize summary alarm images 2034 (as opposed to, or in addition to, video feeds) which can be transmitted rapidly over low speed and/or low bandwidth wireless communications networks.

When a particular active FOV 2018 of the designated or stored FOVs 2020 is to be monitored, the imaging system 2000 moves to image the active FOV 2018 and the fluid leak detection methods disclosed herein can be utilized to detect and/or identify fluid leaks (e.g., gas leaks, oil leaks, etc.) for a predetermined period of time T, which may be any suitable time period, for example, 15 s, 30 s, 1 min, etc. Within the time period T, the imaging system 2000 may capture a multispectral image at a cycle time t (e.g., every 1 s, every 5 s, etc.), and the system 2000 may determine whether there are any fluid leaks within the multispectral image. As explained above, it can be challenging to transfer the entire recorded video stream to the monitoring computer system 2001 over low speed networks.

Accordingly, in various embodiments disclosed herein, if an event is detected by the imaging system 2000 (e.g., if a target gas concentration is detected at or above a predetermined threshold), then the system 2000 can create the summary alarm image 2034 by detecting the target species 2035 over multiple frames of the image data and combining the multiple frames of image data into the summary alarm image 2034 that presents the detection of the target species 2035 over a period of time. In various embodiments, for example, the concentration of the detected species 2035 (or image data representative of the concentration of the species 2035) can be averaged or otherwise weighted over the frames captured during the time period T For example, the summary alarm image 2034 can comprises an average of, e.g., 5, 10, 20, 30, 40, 50, 100 frames over a time period equal to the number of frames divided by the frame rate. This period may correspond to the time or dwell period, T, as referenced above. Although time averaging the concentration can be employed, other approaches that involve accumulating data and/or calculating values over an extended period of time, e.g., T, can be used. Also the number of frames can be different. The resulting summary alarm image 2034 can comprise a single alarm image or a plurality of separate alarm images. For example, in some embodiments, a single alarm image can be generated for each time period T or dwell time to provide a time-averaged illustration of an event over multiple frames of video feed. In other embodiments, multiple alarm images can be generated within the time period T, e.g., if the time period T is particularly long, or it is otherwise desirable to present multiple summary images. In some embodiments, the summary alarm image 2034 can be combined or averaged (or otherwise calculated) over the entire time period T or dwell time at which the FOV of interest is being monitored. In other embodiments, the summary alarm image 2034 can be combined or averaged (or otherwise calculated) over a portion of (i.e., less than) the entire time period T or dwell time at which the FOV of interest is being monitored. Beneficially, the summary alarm image 2034 can comprise a relatively low resolution illustration of the fluid leak during the time period T that can provide the user with a snapshot of the event being monitored. Furthermore, since every frame of the raw video data need not be transmitted over the communications network, the summary alarm image 2034 can provide an efficient way to transfer important information about an event over low speed networks from remote locations.

In various embodiments, the time period T or dwell time at which a particular FOV 2022 is being monitored can be in a range of 1 sec to 60 min, in a range of 1 sec to 10 min, in a range of 1 sec to 1 min, in a range of 1 sec to 45 sec, in a range of 1 sec to 30 sec, or in a range of 1 sec to 15 sec (e.g., about 15 s). Any suitable time period T or dwell time may be used. The frame rate of the video feed during a particular period T or dwell time can be any suitable frame rate, e.g., in a range of 0.1 frames per second (fps), to 60 fps, in a range of 0.1 fps to 30 fps, in a range of 0.5 fps to 30 fps, in a range of 0.5 fps to 15 fps, or in a range of 1 fps to 10 fps. For various embodiments disclosed herein, including some embodiments that utilize low bandwidth cellular networks, lower frame rates may be used. In some embodiments, the summary alarm image 2034 can be generated at the end of each time period T or dwell time. In some embodiments, the summary alarm image 2034 can be continuously generated after each frame, or after a plurality of frames, until the time period T expires.

Figure 17A:
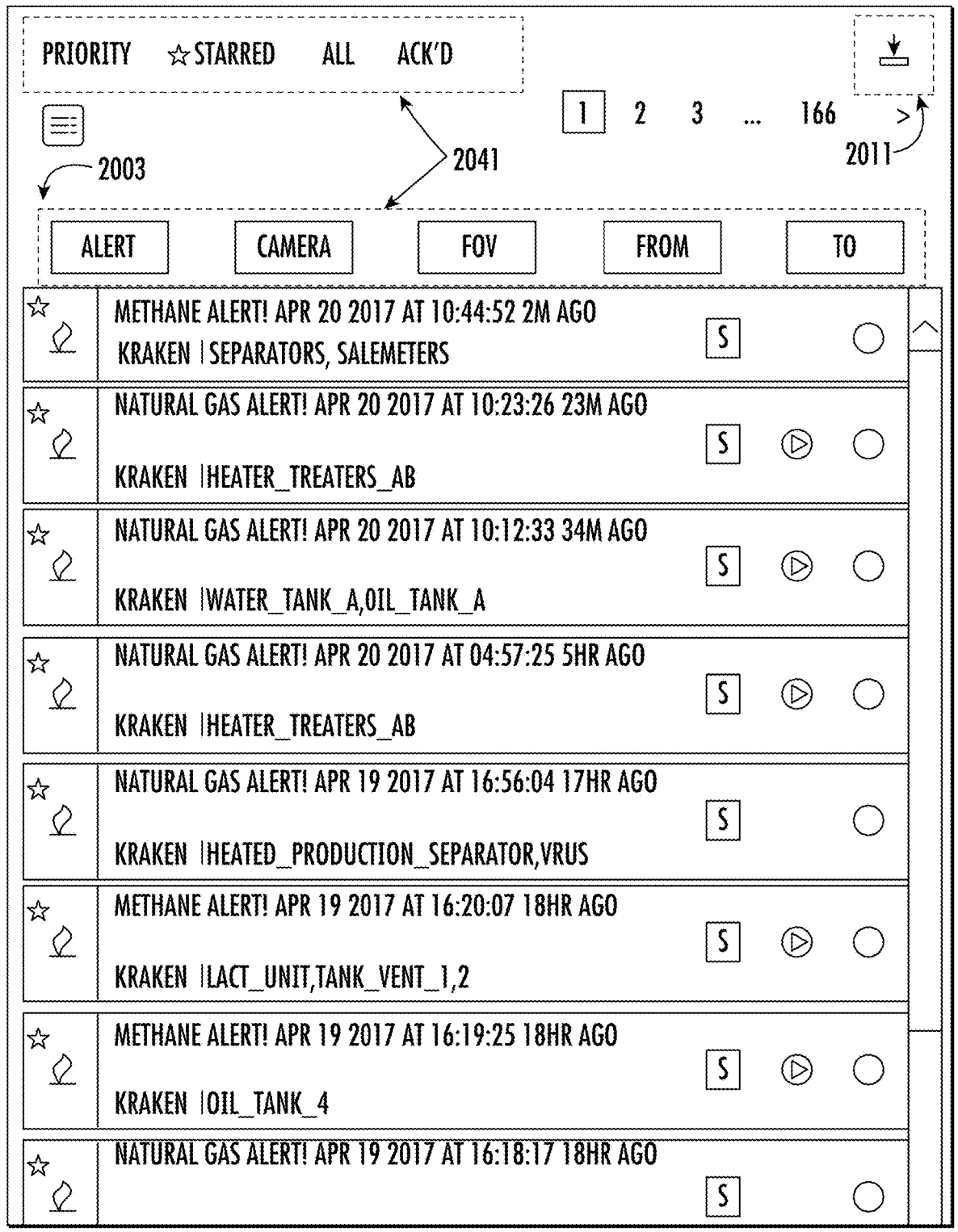
FIG. 17A is a schematic diagram of an events log, according to various embodiments.

The summary alarm image 2034 can also enable the user to quickly and accurately identify the approximate location of the source of the fluid leak, since the leaked fluid concentrations can be represented by a color scale overlaid on the image of the scene. For example, the user may associate areas of maximum concentration M with the source of the fluid leak. As explained above, when an event (such as a fluid leak) is detected and/or identified by imaging system 2000 (e.g., when a concentration of a target species exceeds a threshold), the associated imaging system 2000 can transmit an alert or alarm to the monitoring computer system 2001 indicating the type and concentration of the species detected. In addition, the imaging system 2000 can transmit the summary alarm image 2034 to the monitoring computer system 2001 so that the user can view a time-averaged summary of the concentration of the species over the time period T monitored by the imaging system 2000. The event or alarm can be posted to the event log 2003 with details about the time, location, type, and concentration of the leak, and/or other information about the event, or any combination of these parameters. Furthermore, the user can access the summary alarm image 2034 by way of the event log 2003 (e.g., by way of the "S" button shown in FIG. 17A). In various embodiments, the user can access low resolution video feed of the event by way of the event log 2003 as well (e.g., by way of a triangular "play" button, which is shown in FIG. 17A).

In some embodiments, one or more imaging systems 2000 may produce multiple gas detection and/or quantification maps for a particular FOV at the monitored facility over a period of time (e.g., seconds, minutes, hours, days, etc.). These multiple gas detection and/or quantification maps may be generated at typical video frame rates (e.g., 30 frames per second), but maps or images may also be generated at wider time intervals. A processing device, such as an image processor, may analyze the multiple gas detection and/or quantification maps and generate a representative summary alarm image 2034. In various embodiments, the processing device may be part of, locally connected to, or located near, the imaging system(s) 2000 at the facility where gas leak monitoring is being performed. In some embodiments, the local processing device analyzes the multiple gas detection and/or quantification maps to identify a subset of those images (e.g., one image) which are representative of a detected gas leak over the period of time. For example, the local processing device may analyze each of the multiple gas detection and/or quantification maps to identify one or more gas leaks in those images. The local processing device may then select one image (or a small plurality of images) that is representative of the leak. In other embodiments, the summary image 2034 may be a composite image that includes information from multiple gas detection and/or quantification maps or images detected over multiple frames. For example, as explained above, in such embodiments, the summary alarm image 2034 may comprise a time average of the multiple gas detection and/or quantification maps. This time average summary image can be generated by the local processing device by averaging the multiple maps on a pixel by pixel basis. This type of summary image 2034 can be effective at capturing gas leak activity over time, as gas clouds are ever-changing objects such that the blurring that may occur by averaging multiple images over time does not negatively impact the ability to observe useful information about a gas cloud from such an image. Accordingly, this and other types of summary images may be useful to operators for identifying gas leak activity within a monitored field of view over a period of time in a single image. In other embodiments, other statistical and/or image processing techniques can be used to create a composite image. Summary images 2034 offer a bandwidth- and time-efficient way for operators to quickly assess a site for potential gas leaks. A summary image 2034 can be transmitted to an operator alone, without the source data (e.g., a video) which was collected in order to generate the summary image. Or if enough data bandwidth exists to transmit the source data, such as a video, then the summary image 2034 can be used as a cover image for the recorded video it belongs to and can be viewed by clicking the summary button on the related event in the event log 2003.

Accordingly, the embodiments disclosed herein can provide the user at the monitoring computer system 2001 with accurate and timely information about events (e.g., fluid leaks) that occur at installations being monitored by associated imaging systems 2000. Moreover, the data transmitted to the user at the computer system 2001 can be rapidly and reliably transmitted over a suitable wireless communications network, e.g., having different speeds, including networks that are relatively low speed and low bandwidth networks, such as wireless cellular networks. As explained above, the user can engage the viewing mode bar 2024 to allow the user to select a desired viewing mode, e.g., a live-stream video mode, a progressive mode (discussed below), etc. If the user would like to see a live stream of the monitored FOV (whether visible or IR image data) in real-time, the user can select the live-stream mode. In some embodiments, such as those in which a high speed connection (e.g., Ethernet or WiFi) is available, the user may be able to view relatively high resolution and/or high frame rate videos by selecting the live-stream mode. In other embodiments, such as those in which only a low speed connection (e.g., cellular connection) is available, the user may be able to view relatively low resolution and/or low frame rate videos by selecting the live-stream mode.

In addition, the user can select the progressive mode to sequentially view summary alarm images 2034 for successive stored FOVs 2022. For example, if there are N FOVs 2022 for a particular imaging system 2000, the progressive mode can progressively present summary alarm images 2034 for FOV 1, FOV 2, FOV 3, ... FOV N, so that the user can view events such as fluid leaks at each FOV 2022 of the imaging system 2000. In some embodiments, when the system is in the progressive mode, the system can present summary alarm images 2034 for a particular FOV 2022 only when an alarm is triggered for that particular FOV 2022 during the time period T being monitored. In some embodiments, if no alarm is triggered for the particular FOV 2022 during the time period T being monitored, then the system can present low resolution video image data (e.g., visual and/or IR image data) of the FOV 2022 being monitored. In other embodiments, if no alarm is triggered for the particular FOV 2022, then no image data is presented and/or the imaging system 2000 with no alarm may be skipped in the cycle of the progressive mode.

Thus, as one example, during a cycle of the progressive mode, the imaging system 2000 being monitored detects a fluid leak at FOV 1 and FOV 3, but does not detect any leaks or other events at FOV 2 and FOV 4. In some embodiments utilizing the progressive mode, the cycle can illustrate a low resolution video (e.g., visible and/or IR image data) of FOV 1 for a first period followed by the summary alert image 2034 that illustrates the time averaged leak data for a second period (or vice versa). The progressive mode can alternately illustrate low resolution video of FOV 1 and the summary alert image 2034 of FOV 1 for the time period T that FOV 1 is being monitored. In other embodiments, the system can illustrate only the summary alert image(s) 2034 of FOV 1 during the time period T.

When the time period T for monitoring FOV 1 is complete, the progressive mode can progress to FOV 2. Since no alarm is indicated for FOV 2, the system can present low resolution video streams (e.g., visible and/or IR image data) for the time period T being monitored. When the time period T for monitoring FOV 2 is complete, the progressive mode can progress to FOV 3. Because the system 2000 detects a fluid leak at FOV 3 during the time period T, the progressive mode can alternately present low resolution video of the FOV 3 with the summary alert image 2034 of the FOV 3 over the time period T, as explained above. When the monitoring period for FOV 3 is complete, the system can present low resolution video of FOV 4 for the time period T, since no alarm is indicated at FOV 4 during this period.

Thus, the progressive scanning mode of the systems disclosed herein can beneficially present the user with an accurate and rapid identification of events that occur during the time period T being monitored by a particular imaging system 2000. The use of summary alarm images 2034 for presenting event data to the user can enable the use of low speed communications networks to obtain rich data from even remote petrochemical installations or facilities.

Moreover, in some embodiments, different events can be grouped together based on event type (e.g., gas or liquid leak, intrusion, etc.), type of detected gas or liquid, event time, message, and/or FOV (e.g. which imaging system 2000 detected the event, and/or positions within a scan of the imaging system 2000). The interface can present several algorithm options that can be used to determine the path direction of the fluid leak and/or wind direction at the time of the event. Events can be added to a particular group of events if, for example, a time difference (delta T) between a current event and a most recent event within the group does not exceed a predetermined time limit (e.g., 5 minutes, and/or can be based on the FOVs in path and visit times). In another embodiment, a single event can be shown to generate a single, but longer than default, video clip that does not exceed the video maximum length. In some embodiments, multiple grouped events can comprise parent and child events, which can be caused by or follow after parent events. For example, for multiple generated grouped events, information about the parent event can be replaced with the most recent event in the group (including time stamp). The listed parent event can show a number of child events that occurred after or because of the parent event. In some embodiments, only the parent event can be displayed on the event panel and a "show all child events" button can be engaged to show the depending child events. When the user acknowledges the parent event or a grouped single event (e.g., changes the event status by pressing the "event status" button), all child events in this group may be automatically checked as acknowledged.

Thus, in various embodiments, the processing electronics can be configured to associate multiple events with one another and to form a group of the associated multiple events. The processing electronics can be configured to form the group of the associated multiple events based at least in part on at least one of event type, type of the detected one or more target species, event time, and a field of view (FOV) in which the one or more target species has been detected. For example, in various embodiments, if a particular imaging system 2000 detects a fluid leak in multiple FOVs, then the processing electronics can associate the detections identified in the multiple FOVs in a grouping of events. Additionally, if an imaging system 2000 detects a fluid leak during the same time period, the processing electronics may similarly group those detections into a grouping of events. Similarly, if an imaging system 2000 detects a fluid leak at different times that are grouped closely together, the processing electronics may similarly group those detections into a grouping of events. Further, if other types of events occur at similar times or locations, the processing electronics can likewise groups those events. For example, if a collection of systems 2000 are offline during the same time period, the processing electronics can determine that the systems 2000 are offline due to a related event (e.g., a power outage, etc.). If multiple events are grouped together by the electronics, an event (e.g., the first event detected) may be assigned as the parent event, and the other grouped events (e.g., subsequent event(s)) may be assigned as child events. The events may be grouped for a predetermined time period in some embodiments.

Beneficially, the grouping of events described herein can assist in reducing the occurrence of redundant or otherwise less relevant alarms. For example, if a single fluid leak is detected over multiple FOVs, and an alarm is generated after each detection of the single fluid leak, then the multiple alarms may bombard the user with redundant information and/or create confusion, a distraction, or nuisance if multiple alarms are indicated at once or repeatedly over short intervals. Grouping the single fluid leak into a single event (and, for example, a single alarm or alert) can advantageously simplify the monitoring process for the user, for example, by reducing extraneous alarms.

The imaging systems 2000 disclosed herein can detect fluid leaks that include gas leaks (e.g., methane leaks, hydrogen sulfide leaks, etc.) and/or liquid leaks (e.g., crude oil leaks). Gas leaks occur very rapidly, since the gases can freely escape into the atmosphere at a high rate. For tracking the progression of a gas leak, the imaging systems 2000 disclosed herein can overlay a color map onto the imaged FOV 2022 that relates the color map to an estimated concentration of the leaked gas (see, e.g., the summary image 2034 of FIG. 16C). Utilizing color maps to track gas leaks based on concentration is an effective way of monitoring the progression and/or identifying the source of the gas leak, because gases leak on relatively fast time scales.

By contrast, for liquid leaks (such as oil leaks), the liquid may seep into the ground or other surface at relatively low rates, e.g., over the periods of hours, days, or weeks. Due to the low rate of progression of liquid leaks, it can be challenging to monitor the progression of a liquid leak and/or to identify the source of the liquid leak. Accordingly, various embodiments disclosed herein enable the user to track the liquid leak over relatively long time periods and to identify the source of the leak utilizing the systems 2000 disclosed herein.

Turning to FIG. 16D, a time lapsed leak progression image 2036 that shows the progression of a liquid leak over a time period is illustrated, according to various embodiments. In FIG. 16D a color map of a liquid leak 2039 is overlaid on an image (e.g., a visible or IR image, in this case a visible image) of the FOV 2022 that is monitored. However, instead of the color map representing an estimated concentration of the target species (such as for gas leaks), the progression of the liquid leak 2039 of FIG. 16D is mapped based on an amount of time that the liquid leak 2039 is present at a particular location within the FOV 2022. For example, as shown in FIG. 16D, the liquid leak 2039 can comprise a first region 2037 (e.g., ring or contour) that indicates a long residence time of the liquid leak 2039 and a second region 2038 (e.g., ring or contour) that indicates a short residence time of the liquid leak 2039. Since the first region 2037 has a relatively long residence time in which the liquid (e.g., oil) has been present at that particular location, the user may infer that the source of the liquid leak is at or near the first region 2037. Because the second region 2038 has a relatively short residence time in which the liquid (e.g., oil) has been present at the second region 2038, the user may infer that the liquid leak has only recently progressed to the second region 2038. Although two regions 2037, 2038 are shown in FIG. 16D, it should be appreciated that the system 2000 can identify any suitable number of regions for tracking the progression of the liquid leak 2039. Further in some embodiments, the system 2000 can automatically detect and/or indicate the estimated time periods at which the liquid leak 2039 has been present at each location (e.g., at the regions 2037, 2038). For example, the system 2000 can indicate that the liquid leak 2039 has been present in the first region 2037 for a first time period (e.g., 3 days, 2 hours, 33 minutes), and that the liquid leak 2039 has been present in the second region 2038 for a second, shorter time period (e.g., 2 hours, 15 minutes).

Accordingly, the embodiment of FIG. 16D can advantageously provide the user with rich information, in a relatively small image size, about the progression of a liquid leak 2039 over a long time period (e.g., on the order of hours, days, weeks, etc.). The color coded map of FIG. 16D can be efficiently and rapidly communicated over low speed communications networks and can enable the user to identify the source of the liquid leak, as well as its progression over time. For example, by illustrating leak residence time based on color-coded rings or contours, the user can easily determine at a glance the location of the source of the leak and/or the general spatial extent of the leak over time in a single image.

FIG. 17A is a schematic diagram of the events log 2003, according to various embodiments. FIG. 17B is a schematic diagram of an event guide 2040, according to various embodiments. As explained above, the event log 2003 can be presented on the user interface that is rendered to the user at the central monitoring computer system 2001 (see also FIG. 16A). The event guide 2040 can provide a summary of possible event types and information about those event types. As shown in FIG. 17A, the event log 2003 can present a list of events detected by the imaging systems 2000 being monitored by the computer system 2001. In some embodiments, the events can be automatically prioritized based on the urgency of the event. For example, the system can automatically determine that events such as fluid leaks have higher priority than other types of events, such as a high disk use notification, ping failure, or the other events listed in FIG. 17B. Thus in some embodiments, processing electronics (e.g., of the imaging system 2000) can be configured to analyze the events log 2003, and based on the analysis, to transmit a priority ranking of events to the computing system 2001.

The event log 2003 can be sorted based on filters 2041 selected by the user. For example, the user can sort the events based on those starred by the user, based on priority of the event (which may be automatically generated by the system), based on timing of the event, based on which system 2000 detected the event, based on FOV 2022 of the event, or based on any other suitable filter or parameter. The events log 2003 can include links to the summary alarm image 2034 associated with the event (and or the progression image 2036 of a liquid leak) and/or links to video image data of the event, to provide the user with a convenient interface for accessing information about the events.

As shown in FIG. 17B, high priority events (such as a fluid leak) can be indicated with a high priority icon, medium priority events (such as disk failure) can be indicated with a medium priority icon, low priority events (such as high disk use) can be indicated with a low priority icon, a detection event can be indicated with a detection icon, and other events (such as threshold changes or mode changes) can be indicated with other types of icons or no icons. Beneficially, the priorities can also be illustrated to the user based on color-codes. For example, icons associated with high priority events can be red, icons associated with medium priority events can be orange, icons associated with low priority events can be yellow, detection events can be gray, and other events can be black. Any suitable color codes can be used, however, for the priorities. Further, as shown in FIG. 17B, the system 2000 can provide a brief description as well as a full message associated with the event.

In various embodiments disclosed herein, events (e.g., gas leaks, intrusion detection) can automatically generate a pop-up notification and/or sound that notifies the user of the event. Furthermore, the embodiments disclosed herein can be employed with other devices and sensors, such as other optical cameras, point sensors, temperature sensors, motion sensors, etc. Data from the other devices can be transmitted to and/or from the user computing systems over the communications networks disclosed herein.

References throughout this specification to "one embodiment," "an embodiment," "a related embodiment," or similar language mean that a particular feature, structure, or characteristic described in connection with the referred to "embodiment" is included in at least one embodiment of the present invention. Thus, appearances of the phrases "in one embodiment," "in an embodiment," and similar language throughout this specification may, but do not necessarily, all refer to the same embodiment. It is to be understood that no portion of disclosure, taken on its own and in possible connection with a figure, is intended to provide a complete description of all features of the invention.

In the drawings like numbers are used to represent the same or similar elements wherever possible. The depicted structural elements are generally not to scale, and certain components are enlarged relative to the other components for purposes of emphasis and understanding. It is to be understood that no single drawing is intended to support a complete description of all features of the invention. In other words, a given drawing is generally descriptive of only some, and generally not all, features of the invention. A given drawing and an associated portion of the disclosure containing a description referencing such drawing do not, generally, contain all elements of a particular view or all features that can be presented is this view, for purposes of simplifying the given drawing and discussion, and to direct the discussion to particular elements that are featured in this drawing. A skilled artisan will recognize that the invention may possibly be practiced without one or more of the specific features, elements, components, structures, details, or characteristics, or with the use of other methods, components, materials, and so forth. Therefore, although a particular detail of an embodiment of the invention may not be necessarily shown in each and every drawing describing such embodiment, the presence of this detail in the drawing may be implied unless the context of the description requires otherwise. In other instances, well known structures, details, materials, or operations may be not shown in a given drawing or described in detail to avoid obscuring aspects of an embodiment of the invention that are being discussed. Furthermore, the described single features, structures, or characteristics of the invention may be combined in any suitable manner in one or more further embodiments.

Moreover, if the schematic flow chart diagram is included, it is generally set forth as a logical flow-chart diagram. As such, the depicted order and labeled steps of the logical flow are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow-chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Without loss of generality, the order in which processing steps or particular methods occur may or may not strictly adhere to the order of the corresponding steps shown.

The features recited in claims appended to this disclosure are intended to be assessed in light of the disclosure as a whole.

At least some elements of a device of the invention can be controlled—and at least some steps of a method of the invention can be effectuated, in operation—with a programmable processor governed by instructions stored in a memory. The memory may be random access memory (RAM), read-only memory (ROM), flash memory or any other memory, or combination thereof, suitable for storing control software or other instructions and data. Those skilled in the art should also readily appreciate that instructions or programs defining the functions of the present invention may be delivered to a processor in many forms, including, but not limited to, information permanently stored on non-writable storage media (e.g. read-only memory devices within a computer, such as ROM, or devices readable by a computer I/O attachment, such as CD-ROM or DVD disks), information alterably stored on writable storage media (e.g. floppy disks, removable flash memory and hard drives) or information conveyed to a computer through communication media, including wired or wireless computer networks. In addition, while the invention may be embodied in software, the functions necessary to implement the invention may optionally or alternatively be embodied in part or in whole using firmware and/or hardware components, such as combinatorial logic, Application Specific Integrated Circuits (ASICs), Field-Programmable Gate Arrays (FPGAs) or other hardware or some combination of hardware, software and/or firmware components.

While examples of embodiments of the system and method of the invention have been discussed in reference to the gas-cloud detection, monitoring, and quantification (including but not limited to greenhouse gases such as Carbon Dioxide, Carbon Monoxide, Nitrogen Oxide as well as hydrocarbon gases such as Methane, Ethane, Propane, n-Butane, iso-Butane, n-Pentane, iso-Pentane, neo-Pentane, Hydrogen Sulfide, Sulfur Hexafluoride, Ammonia, Benzene, p- and m-Xylene, Vinyl chloride, Toluene, Propylene oxide, Propylene, Methanol, Hydrazine, Ethanol, 1,2-dichloroethane, 1,1-dichloroethane, Dichlorobenzene, Chlorobenzene, to name just a few), embodiments of the invention can be readily adapted for other chemical detection applications. For example, detection of liquid and solid chemical spills, biological weapons, tracking targets based on their chemical composition, identification of satellites and space debris, ophthalmological imaging, microscopy and cellular imaging, endoscopy, mold detection, fire and flame detection, and pesticide detection are within the scope of the invention.

As used herein, a phrase referring to "at least one of" a list of items refers to any combination of those items, including single members. As an example, "at least one of: a, b, or c" is intended to cover: a, b, c, a-b, a-c, b-c, and a-b-c.

If implemented in software, the functions may be stored on or transmitted over as one or more instructions or code on a computer-readable medium. The steps of a method or algorithm disclosed herein may be implemented in a processor-executable software module which may reside on a computer-readable medium. Computer-readable media includes both computer storage media and communication media including any medium that can be enabled to transfer a computer program from one place to another. A storage media may be any available media that may be accessed by a computer. By way of example, and not limitation, such computer-readable media may include RAM, ROM, EEPROM, CD-ROM or other optical disk storage, magnetic disk storage or other magnetic storage devices, or any other medium that may be used to store desired program code in the form of instructions or data structures and that may be accessed by a computer. Also, any connection can be properly termed a computer-readable medium. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above also may be included within the scope of computer-readable media. Additionally, the operations of a method or algorithm may reside as one or any combination or set of codes and instructions on a machine readable medium and computer-readable medium, which may be incorporated into a computer program product.

Various modifications to the implementations described in this disclosure may be readily apparent to those skilled in the art, and the generic principles defined herein may be applied to other implementations without departing from the spirit or scope of this disclosure. Thus, the claims are not intended to be limited to the implementations shown herein, but are to be accorded the widest scope consistent with this disclosure, the principles and the novel features disclosed herein.

Certain features that are described in this specification in the context of separate implementations also can be implemented in combination in a single implementation. Conversely, various features that are described in the context of a single implementation also can be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

The invention claimed is:

1. A system for monitoring a plurality of installations, the system comprising:
a communications module configured to receive infrared image data from a plurality of optical imaging systems at the plurality of installations, the plurality of optical imaging systems configured to capture the infrared image data at the plurality of installations; and
processing electronics configured to:
detect a plurality of events at the plurality of installations based at least in part on the infrared image data,
form an associated event group based at least in part on one or more types of one or more target species associated with the plurality of events, and
transmit an alarm notification to an external computing device over a communications network indicating the associated event group.

2. The system of claim 1, wherein the processing electronics are configured to detect a target species based at least in part on the infrared image data.

3. The system of claim 2, wherein the processing electronics are configured to:
compare a detected amount of the target species to a threshold amount, and based on determining that the detect amount exceeds the threshold amount, transmit the alarm notification to the external computing device over the communications network indicating that the target species has been detected at the plurality of installations.

4. The system of claim 3, wherein the threshold amount is in a first range of 1 ppm-m to 1000 ppm-m of the target species.

5. The system Of claim 4, wherein the threshold amount is in a second range of 25 ppm-m to 1000 ppm-m of the target species.

6. The system of claim 5, wherein the threshold amount is in a third range of 25 ppm-m to 750 ppm-m of the target species.

7. The system of claim 2, wherein the target species comprises one or more of methane or hydrogen sulfide.

8. The system of claim 2, wherein the target species comprises one or more of a gas or a liquid.

9. The system of claim 1, wherein the processing electronics are configured to combine multiple frames of the infrared image data into a summary alarm image that presents a detection of a target species over a period of time.

10. The system of claim 9, wherein the processing electronics are configured to create the summary alarm image by calculating one or more of an average concentration of the target species over a plurality of successive frames of the infrared image data and/or an average of the infrared image data representative of a concentration of the target species over the period of time.

11. The system of claim 9, wherein the processing electronics are configured to generate a progressive mode to sequentially present summary alarm images for successive fields of view (FOVs) of an optical imaging system of the plurality of optical imaging systems.

12. The system of claim 1, wherein the processing electronics are configured to create an events log comprising the plurality of events based on the one or more target species detected by the processing electronics.

13. The system of claim 12, wherein the processing electronics are configured to analyze the events log, and based on the analysis, to transmit a priority ranking of events to the external computing device.

14. The system of claim 1, wherein the processing electronics are configured to detect an unauthorized intrusion of one or more of an animal or a human into one or more petroleum installations associated with the plurality of installations and, based on the detection, to transmit a second alarm notification to the external computing device over the communications network indicating the unauthorized intrusion.

15. The system of claim 1, wherein the communications network comprises one or more of a wireless communications network or an Ethernet communications network.

16. The system of claim 1, wherein the processing electronics are further configured to transmit information about the plurality of events detected at the plurality of installations to the external computing device, the external computing device being configured to generate a user interface presentable to a user on a display device, wherein the user interface comprises a visible image window and an infrared image window.

17. The system of claim 1, wherein the plurality of optical imaging systems comprise one or more of an infrared (IR) detector array or a visible light detector array.

18. The system of claim 1, wherein the plurality of optical imaging systems define a plurality of optical channels being spatially and spectrally different from one another, each of the plurality of optical channels positioned to transfer radiation incident on an optical imaging system towards an array of optical detectors.

19. The system of claim 1, wherein the processing electronics are further configured to monitor a progression of a liquid leak over a period of time.

20. The system of claim 16, wherein the user interface comprises a multi-view window, wherein the multi-view window comprises a plurality of infrared images based on the infrared image data, wherein each of the plurality of infrared images is associated with one of the plurality of optical imaging systems.

* * * * *